(12) United States Patent
Kanno et al.

(10) Patent No.: US 8,410,273 B2
(45) Date of Patent: Apr. 2, 2013

(54) CYCLIC COMPOUND HAVING SUBSTITUTED PHENYL GROUP

(75) Inventors: Osamu Kanno, Kanagawa (JP); Katsuyoshi Nakajima, Tokyo (JP); Kazumasa Aoki, Tokyo (JP); Ryoichi Tanaka, Tokyo (JP); Shimpei Hirano, Chiba (JP); Kiyoshi Oizumi, Kanagawa (JP); Satoru Naito, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/253,792

(22) Filed: Oct. 5, 2011

(65) Prior Publication Data

US 2012/0040936 A1 Feb. 16, 2012

Related U.S. Application Data

(63) Continuation of application No. PCT/JP2010/055547, filed on Mar. 29, 2010.

(30) Foreign Application Priority Data

Apr. 6, 2009 (JP) ................. 2009-091671

(51) Int. Cl.
*C07D 471/02* (2006.01)
*A61K 31/47* (2006.01)
(52) U.S. Cl. ........................ 546/122; 514/307
(58) Field of Classification Search .................. 546/122; 514/307
See application file for complete search history.

(56) References Cited

U.S. PATENT DOCUMENTS 7,282,506 B2 * 10/2007 Hanson et al. ............... 514/300

FOREIGN PATENT DOCUMENTS

| EP | 0 634 169 A1 | 1/1995 |
| JP | 9188665 A | 7/1997 |
| JP | 2008-509151 A | 3/2008 |
| WO | 2006/017672 A2 | 2/2006 |

OTHER PUBLICATIONS

Silverman, R., "The Organic Chemistry of Drug Design and Drug Action," 2004, Elsevier, pp. 29-32.*
International Search Report mailed May 11, 2010, issued in corresponding International Application No. PCT/JP2010/055547, filed Mar. 29, 2010, 3 pages.
Extended European Search Report mailed Jul. 13, 2012, issued in corresponding European Application No. 10761614.6, filed Mar. 29, 2010, 5 pages.

* cited by examiner

*Primary Examiner* — David K O'Dell
*Assistant Examiner* — Heidi Reese
(74) *Attorney, Agent, or Firm* — Christensen O'Connor Johnson Kindness PLLC

(57) ABSTRACT

Low molecular weight compound exhibiting an osteogenesis-promoting action having the general formula (I) or a pharmacologically acceptable salt thereof:

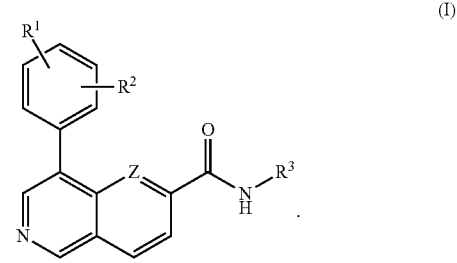

(I)

11 Claims, No Drawings

CYCLIC COMPOUND HAVING SUBSTITUTED PHENYL GROUP

TECHNICAL FIELD

The present invention relates to a cyclic compound having a substituted phenyl group or a pharmacologically acceptable salt thereof useful for the prevention or treatment of diseases associated with bone metabolism, for example, osteoporosis, osteitis fibrosa (hyperparathyroidism), osteomalacia, and Paget's disease.

BACKGROUND ART

Generally in normal bone metabolism, bone resorption by osteoclasts and osteogenesis by osteoblasts are balanced, whereby homeostasis is maintained. It is presumed that diseases associated with bone metabolism develop when the balance between bone resorption and osteogenesis is disrupted. Such diseases include osteoporosis, osteitis fibrosa (hyperparathyroidism), osteomalacia, Paget's disease, and the like. Particularly, osteoporosis often develops in postmenopausal women and elderly people with accompanying symptoms of pain such as low back pain, bone fracture, etc. Particularly, bone fracture in elderly people is serious because it leads to generalized weakness and dementia. For such diseases associated with bone metabolism, hormone replacement therapies with estrogen and therapeutic agents such as bisphosphonates and calcitonins, both of which inhibit the activity of osteoclasts, have been employed.

However, although many of these therapeutic agents are reported to have a bone resorption-inhibiting action, etc., none of them has yet been clearly shown to have an osteogenesis-promoting action. Particularly, impaired osteogenic ability due to reduced bone turnover is reported to be the main cause of senile osteoporosis (Non Patent Reference 1), and thus a medicinal agent promoting osteogenesis is considered to be effective.

In view of the above, development of a highly clinically effective, orally administrable osteogenesis promoter is demanded.

Recently, benzothiepine derivatives having an alkaline phosphatase-inducing activity (Patent References 1 and 2), N-quinolylanthranilic acid derivatives (Patent Reference 3), triazolopyridazine derivatives (Patent Reference 4), and thienopyridine derivatives (Patent Reference 5) are reported to be useful for promotion of osteogenesis and for the treatment of diseases associated with bone metabolism. However, their clinical utility remains unknown.

CITATION LIST

Patent References

Patent Reference 1: U.S. Pat. No. 6,346,521
Patent Reference 2: U.S. Pat. No. 6,632,807
Patent Reference 3: Japanese Patent Laid-Open No. 9-188665
Patent Reference 4: U.S. Pat. No. 7,173,033
Patent Reference 5: Japanese Patent Laid-Open No. 2007-131617

Non Patent Literature

Non Patent Reference 1: New Eng. J. Med. 314, 1976 (1986)

SUMMARY OF INVENTION

Technical Problem

In order to reduce pain and risk of bone fracture in diseases associated with bone metabolism such as osteoporosis, bone mass and bone strength need to be increased. As a means of increasing bone mass and bone strength, it is considered to be important to promote osteogenesis by osteoblasts as this is considered to be definitely effective. Accordingly, an object of the present invention is to provide a highly safe, orally administrable novel low molecular weight compound exhibiting an osteogenesis-promoting action.

Solution to Problem

The present inventors conducted an intensive study in order to develop a therapeutic medication with an osteogenesis-promoting action. As a result, they have found an excellent compound of the present invention that exhibits a potent osteogenesis-promoting action and is potentially capable of serving as a therapeutic medication for the prevention or treatment of diseases associated with bone metabolism, thereby completing the present invention.

That is, the present invention is as follows.

(1) A compound having the general formula (I) or a pharmacologically acceptable salt thereof:

[Chemical formula 1]

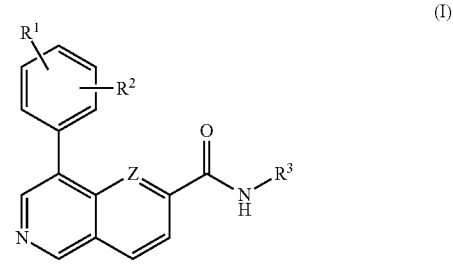

wherein each substituent is defined as follows:
R¹ represents a group selected from a substituent group α,
R² represents a group selected from a substituent group α, (or R¹ and R² together form a 5- to 6-membered heterocyclic group optionally substituted by groups selected from a substituent group β),
R³ represents a hydrogen atom or a C1-C6 alkyl group optionally substituted by a hydroxyl group, and
Z represents —CH= or —N=,
wherein
the substituent group α includes:
a hydrogen atom, a hydroxyl group, a halogen group, a nitro group, a C1-C6 alkylsulfonyl group, a halogeno C1-C6 alkyl group, a halogeno C1-C6 alkoxy group, a C1-C6 alkylcarbonyl group, a di C1-C6 alkylamino group, a di C1-C6 alkylaminocarbonyl group, a di C1-C6 alkylaminocarbonyloxy group, a phenoxy group, a C1-C6 alkoxycarbonyl group, a 4-morpholinyl group,
a C1-C6 alkylamino group optionally substituted by groups selected from a substituent group β, a piperidinyl group optionally substituted by groups selected from a substituent group β,
a piperazinyl group optionally substituted by groups selected from a substituent group β,
a tetrahydropyridinyl group optionally substituted by groups selected from a substituent group β,
a vinyl group optionally substituted by groups selected from a substituent group β,
a C1-C6 alkyl group optionally substituted by groups selected from a substituent group β,
a C1-C6 alkoxy group optionally substituted by groups selected from a substituent group β,
a halogeno C1-C6 alkoxy group optionally substituted by groups selected from a substituent group β, and
a C1-C6 alkoxy C1-C6 alkoxy group optionally substituted by groups selected from a substituent group β, and
the substituent group β includes:
a hydroxyl group, a formyl group, a 2-tetrahydropyranyloxy group, a 3-tetrahydropyranyloxy group, a C1-C6 alkylcarbonyl group, a C1-C6 alkylsulfonyl group, a 4-morpholinyl group, a 4-morpholinylcarbonyl group, a 4-morpholinylcarbonyloxy group, a 4-morpholinylsulfonyl group, a 4-piperidinyl group, a di C1-C6 alkylaminocarbonyl group, a di C1-C6 alkylaminocarbonyloxy group, a C1-C6 alkylphosphonate ester group, a 2-tetrahydrofuranyl group, a 3-tetrahydrofuranyl group, a C1-C6 alkylcarbonylamino group, a C1-C6 alkylsulfonylamino group,
a C1-C6 alkyl group optionally substituted by groups selected from a substituent group γ,
a C1-C6 alkoxy group optionally substituted by groups selected from a substituent group γ,
a 4-tetrahydropyranyloxy group optionally substituted by groups selected from a substituent group γ,
a C3-C6 cycloalkyl group optionally substituted by groups selected from a substituent group γ,
a C3-C6 cycloalkyloxy group optionally substituted by groups selected from a substituent group γ,
a 4-piperidinyloxy group optionally substituted by groups selected from a substituent group γ,
a 1-piperidinylsulfonyl group optionally substituted by groups selected from a substituent group γ,
a piperazinyl group optionally substituted by groups selected from a substituent group γ,
a 3-tetrahydrofuranyloxy group optionally substituted by groups selected from a substituent group γ,
a phenoxy group optionally substituted by groups selected from a substituent group γ, and
a pyridyl group optionally substituted by groups selected from a substituent group γ,
wherein
the substituent group γ includes:
a hydroxyl group, a carboxyl group, a halogen group, a C1-C6 alkyl group, a C1-C6 alkoxy group, a di C1-C6 alkylaminocarbonyl group, a di C1-C6 alkylaminosulfonyl group, a 4-morpholinylcarbonyl group, a C1-C6 alkylsulfonyl group, a C1-C6 alkoxycarbonyl group, a C1-C6 alkylcarbonylamino group, and a C1-C6 alkylsulfonylamino group.

Also, preferred aspects of the present invention are the following.

(2) A compound or a pharmacologically acceptable salt thereof according to (1), wherein $R^1$ is a group selected from the following group of substituents:
a hydroxyl group, a halogen group, a halogeno C1-C6 alkyl group, a halogeno C1-C6 alkoxy group, a di C1-C6 alkylaminocarbonyloxy group, a C1-C6 alkylamino group optionally substituted by groups selected from the substituent group β,
a piperazinyl group optionally substituted by groups selected from the substituent group β,
a tetrahydropyridinyl group optionally substituted by groups selected from the substituent group β,
a vinyl group optionally substituted by groups selected from the substituent group β,
a C1-C6 alkyl group optionally substituted by groups selected from the substituent group β,
a C1-C6 alkoxy group optionally substituted by groups selected from the substituent group β, and
a C1-C6 alkoxy C1-C6 alkoxy group optionally substituted by groups selected from the substituent group β.

(3) A compound or a pharmacologically acceptable salt thereof according to (1), wherein $R^1$ is a group selected from the following group of substituents:
a chlorine group, a fluorine group, a hydroxyl group, 4-morpholin-1-yl, 4-acetylpiperidin-1-yl, propan-2-yloxy, 2-hydroxyethoxy, 4-chloro-2-fluorophenyl, 2,4-difluorophenyl, difluoromethoxy, 2-(tetrahydro-2H-pyran-4-yloxy)ethoxy, and 2-(2-hydroxyethoxy)ethoxy.

(4) A compound or a pharmacologically acceptable salt thereof according to any one of (1) to (3), wherein $R^2$ is a hydrogen atom, a chlorine group, or a fluorine group.

(5) A compound or a pharmacologically acceptable salt thereof according to (1), wherein $R^1$ and $R^2$ together form a pyrrolyl group.

(6) A compound or a pharmacologically acceptable salt thereof according to any one of (1) to (5), wherein $R^3$ is a hydrogen atom, a methyl group, or an ethyl group.

(7) A compound or a pharmacologically acceptable salt thereof according to (1), wherein the general formula (I) is the general formula (I-a).

[Chemical formula 2]

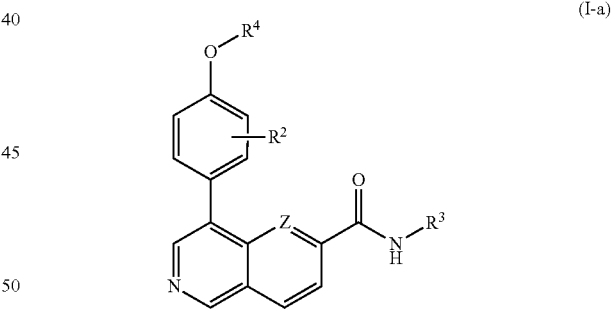

(I-a)

wherein each substituent is defined as follows:
$R^2$ represents a group selected from a substituent group α,
$R^3$ represents a hydrogen atom or a C1-C6 alkyl group optionally substituted by a hydroxyl group,
Z represents —CH= or —N=, and
$R^4$ represents a group selected from a substituent group δ,
wherein
the substituent group α includes:
a hydrogen atom, a hydroxyl group, a halogen group, a nitro group, a C1-C6 alkylsulfonyl group, a halogeno C1-C6 alkyl group, a halogeno C1-C6 alkoxy group, a C1-C6 alkylcarbonyl group, a di C1-C6 alkylamino group, a di C1-C6 alkylaminocarbonyl group, a di C1-C6 alkylaminocarbonyloxy group, a phenoxy group, a C1-C6 alkoxycarbonyl group, a 4-morpholinyl group, a C1-C6 alkylamino group optionally substituted by groups selected from a substituent group β,
a piperidinyl group optionally substituted by groups selected from a substituent group β,
a piperazinyl group optionally substituted by groups selected from a substituent group β,
a tetrahydropyridinyl group optionally substituted by groups selected from a substituent group β,
a vinyl group optionally substituted by groups selected from a substituent group β,
a C1-C6 alkyl group optionally substituted by groups selected from a substituent group β,
a C1-C6 alkoxy group optionally substituted by groups selected from a substituent group β,
a halogeno C1-C6 alkoxy group optionally substituted by groups selected from a substituent group β, and
a C1-C6 alkoxy C1-C6 alkoxy group optionally substituted by groups selected from a substituent group β,
wherein
the substituent group β includes:
a hydroxyl group, a formyl group, a 2-tetrahydropyranyloxy group, a 3-tetrahydropyranyloxy group, a C1-C6 alkylcarbonyl group, a C1-C6 alkylsulfonyl group, a 4-morpholinyl group, a 4-morpholinylcarbonyl group, a 4-morpholinylcarbonyloxy group, a 4-morpholinylsulfonyl group, a 4-piperidinyl group, a di C1-C6 alkylaminocarbonyl group, a di C1-C6 alkylaminocarbonyloxy group, a di C1-C6 alkylphosphonate ester group, a 2-tetrahydrofuranyl group, a 3-tetrahydrofuranyl group, a C1-C6 alkylcarbonylamino group, a C1-C6 alkylsulfonylamino group,
an alkyl group optionally substituted by groups selected from a substituent group γ,
an alkoxy group optionally substituted by groups selected from a substituent group γ,
a 4-tetrahydropyranyloxy group optionally substituted by groups selected from a substituent group γ,
a C3-C6 cycloalkyl group optionally substituted by groups selected from a substituent group γ,
a C3-C6 cycloalkyloxy group optionally substituted by groups selected from a substituent group γ,
a 4-piperidinyloxy group optionally substituted by groups selected from a substituent group γ,
a 1-piperidinylsulfonyl group optionally substituted by groups selected from a substituent group γ,
a piperazinyl group optionally substituted by groups selected from a substituent group γ,
a 3-tetrahydrofuranyloxy group optionally substituted by groups selected from a substituent group γ,
a phenoxy group optionally substituted by groups selected from a substituent group γ, and
a pyridyl group optionally substituted by groups selected from a substituent group γ,
wherein
the substituent group γ includes:
a hydroxyl group, a carboxyl group, a halogen group, a C1-C6 alkyl group, a C1-C6 alkoxy group, a di C1-C6 alkylaminocarbonyl group, a di C1-C6 alkylaminosulfonyl group, a 4-morpholinylcarbonyl group, a C1-C6 alkylsulfonyl group, a C1-C6 alkoxycarbonyl group, a C1-C6 alkylcarbonylamino group, and a C1-C6 alkylsulfonylamino group, and
the substituent group δ includes:
a halogeno C1-C6 alkyl group, a di C1-C6 alkylaminocarbonyl group, a phenyl group,
a C1-C6 alkyl group optionally substituted by groups selected from the substituent group β,
a halogeno C1-C6 alkyl group optionally substituted by groups selected from the substituent group β, and
a C1-C6 alkoxy C1-C6 alkyl group optionally substituted by groups selected from the substituent group β.

(8) A compound or a pharmacologically acceptable salt thereof according to (7), wherein $R^2$ is a hydrogen atom, a chlorine group, or a fluorine group.

(9) A compound or a pharmacologically acceptable salt thereof according to (7) or (8), wherein $R^3$ is a hydrogen atom, a methyl group, or an ethyl group.

(10) A compound or a pharmacologically acceptable salt thereof according to any one of (7) to (9), wherein $R^4$ is a group selected from the following group of substituents:
a di C1-C6 alkylaminocarbonyl group,
a C1-C6 alkyl group optionally substituted by groups selected from the substituent group β, and
a C1-C6 alkoxy C1-C6 alkyl group optionally substituted by groups selected from the substituent group β.

(11) A compound or a pharmacologically acceptable salt thereof according to any one of (7) to (9), wherein $R^4$ is a group selected from the following group of substituents:
a C1-C6 alkyl group, a halogeno C1-C6 alkyl group, a 2-hydroxyethyl group, a 2-(tetrahydro-2H-pyran-4-yloxy)ethyl group, and a 2-(2-hydroxyethoxy)ethyl group.

(12) A compound or a pharmacologically acceptable salt thereof according to (1), wherein the compound having the general formula (I) is a compound selected from the following group of compounds:
8-[4-(morpholin-4-yl)phenyl]-1,6-naphthyridine-2-carboxamide,
4-[4-(4-acetylpiperazin-1-yl)phenyl]isoquinoline-6-carboxamide,
4-[4-(propan-2-yloxy)phenyl]isoquinoline-6-carboxamide,
8-[4-(2-hydroxyethoxy)phenyl]-1,6-naphthyridine-2-carboxamide,
4-[4-(2-hydroxyethoxy)phenyl]isoquinoline-6-carboxamide,
4-(4-chloro-2-fluorophenyl)isoquinoline-6-carboxamide,
4-(2,4-difluorophenyl)isoquinoline-6-carboxamide,
4-[4-(difluoromethoxy)phenyl]isoquinoline-6-carboxamide,
8-{4-[2-(tetrahydro-2H-pyran-4-yloxy)ethoxy]phenyl}-1,6-naphthyridine-2-carboxamide,
4-{4-[2-(tetrahydro-2H-pyran-4-yloxy)ethoxy]phenyl}isoquinoline-6-carboxamide,
N-methyl-8-{4-[2-(tetrahydro-2H-pyran-4-yloxy)ethoxy]phenyl}-1,6-naphthyridine-2-carboxamide,
N-methyl-4-{4-[2-(tetrahydro-2H-pyran-4-yloxy)ethoxy]phenyl}isoquinoline-6-carboxamide,
N-ethyl-8-{4-[2-(tetrahydro-2H-pyran-4-yloxy)ethoxy]phenyl}-1,6-naphthyridine-2-carboxamide,
8-{4-[2-(2-hydroxyethoxy)ethoxy]phenyl}-1,6-naphthyridine-2-carboxamide,
4-{4-[2-(2-hydroxyethoxy)ethoxy]phenyl}isoquinoline-6-carboxamide,
4-(4-chlorophenyl)isoquinoline-6-carboxamide,
4-(4-fluorophenyl)isoquinoline-6-carboxamide,
8-(4-hydroxyphenyl)-1,6-naphthyridine-2-carboxamide,
4-(4-hydroxyphenyl)isoquinoline-6-carboxamide,
8-(3-fluoro-4-hydroxyphenyl)-1,6-naphthyridine-2-carboxamide,
4-(1H-indol-5-yl)isoquinoline-6-carboxamide, and
4-(1-methyl-1H-indol-5-yl)isoquinoline-6-carboxamide.

(13) A compound or a pharmacologically acceptable salt thereof according to (12), wherein the pharmacologically acceptable salt is a hydrochloride.

(14) A pharmaceutical composition comprising a compound or a pharmacologically acceptable salt thereof according to any one of (1) to (13) as an active ingredient.

(15) A pharmaceutical composition according to (14), wherein the pharmaceutical composition is used for promoting osteogenesis.

(16) A pharmaceutical composition according to (14), wherein the pharmaceutical composition is used for improving bone metabolism.

(17) A pharmaceutical composition according to (14), wherein the pharmaceutical composition is used for the prevention or treatment of a disease associated with bone metabolism.

(18) A pharmaceutical composition according to (17), wherein the disease associated with bone metabolism is osteoporosis.

(19) A method for improving bone metabolism, comprising administering an effective amount of a pharmaceutical composition according to (14) to a mammal.

(20) A method for preventing or treating a disease associated with bone metabolism, comprising administering an effective amount of a pharmaceutical composition according to (14) to a mammal.

(21) A method for preventing or treating osteoporosis, comprising administering an effective amount of a pharmaceutical composition according to (14) to a mammal.

Advantageous Effects of Invention

The compound of the present invention has low toxicity and exhibits favorable disposition. Also, it has an osteogenesis-promoting action, and thus is useful for the prevention or treatment of metabolic bone disease associated with reduced osteogenic ability relative to bone resorption ability. Examples of such metabolic bone disease include osteoporosis, osteitis fibrosa (hyperparathyroidism), osteomalacia, and further, Paget's disease, which affects systemic parameters of bone metabolism. In particular, the compound of the present invention is useful for senile osteoporosis associated with impaired osteogenic ability. Further, application of the osteogenesis promoter of the present invention in the field of orthopedics for the promotion of healing of bone fracture, a bone defect, and bone diseases such as osteoarthritis as well as in the field of dentistry for the treatment of periodontal disease, stabilization of artificial tooth root, etc. is anticipated.

DESCRIPTION OF EMBODIMENTS

The present invention will be described in detail hereinbelow.

In the present specification, terms such as substituents used to denote a compound have the following meanings:

A halogen group:
A fluorine group, a chlorine group, or a bromine group

A C1-C6 alkyl group:
A linear or branched alkyl group having a carbon number of 1 to 6. It is preferably a methyl group, an ethyl group, a propyl group, an isopropyl group, or a t-butyl group.

A C1-C6 alkylcarbonyl group:
A group in which a carbonyl group is bound to the aforementioned C1-C6 alkyl group. It is preferably an acetyl group, an ethylcarbonyl group, a propylcarbonyl group, an isopropylcarbonyl group, or a butylcarbonyl group.

A C1-C6 alkylsulfonyl group:
A group in which a sulfonyl group is bound to the aforementioned C1-C6 alkyl group. It is preferably a methylsulfonyl group, an ethylsulfonyl group, a propylsulfonyl group, an isopropylsulfonyl group, or a butylsulfonyl group, of which a methylsulfonyl group or an ethylsulfonyl group is more preferable.

A C1-C6 alkoxy group:
A group in which an oxygen atom is bound to the aforementioned C1-C6 alkyl group. It is preferably a methoxy group, an ethoxy group, a propoxy group, an isopropoxy group, or a t-butoxy group.

A C1-C6 alkoxycarbonyl group:
A group in which a carbonyl group is bound to the aforementioned C1-C6 alkoxy group. It is preferably a methoxycarbonyl group, an ethoxycarbonyl group, a propoxycarbonyl group, an isopropoxycarbonyl group, or a t-butoxycarbonyl group.

A C1-C6 alkylamino group:
A group in which one of the aforementioned C1-C6 alkyl groups is bound to an amino group. It is preferably a methylamino group, an ethylamino group, a propylamino group, an isopropylamino group, or a butylamino group.

A C1-C6 alkoxycarbonylamino group:
A group in which a carbonylamino group is bound to the aforementioned C1-C6 alkoxy group. It is preferably a methoxycarbonylamino group or an ethoxycarbonylamino group.

A C1-C6 alkylsulfonylamino group:
A group in which a sulfonylamino group is bound to the aforementioned C1-C6 alkyl group. It is preferably a methylsulfonylamino group or an ethylsulfonylamino group.

A halogeno C1-C6 alkyl group:
The aforementioned C1-C6 alkyl group that is substituted with a halogen group. Examples thereof include a fluoromethyl group, a difluoromethyl group, a trifluoromethyl group, a fluoroethyl group, a difluoroethyl group, a trifluoroethyl group, a fluoropropyl group, a difluoropropyl group, a trifluoropropyl group, a fluorobutyl group, a difluorobutyl group, a trifluorobutyl group, a fluoropentyl group, a difluoropentyl group, a trifluoropentyl group, a fluorohexyl group, a difluorohexyl group, a trifluorohexyl group, a pentafluoroethyl group, a hexafluoropropyl group, a nonafluorobutyl group, a chloromethyl group, a dichloromethyl group, a trichloromethyl group, a chloroethyl group, a dichloroethyl group, a trichloroethyl group, a chloropropyl group, a dichloropropyl group, or a trichloropropyl group.

A halogeno C1-C6 alkoxy group:
The aforementioned C1-C6 alkoxy group that is substituted with a halogen atom. Examples thereof include a fluoromethoxy group, a difluoromethoxy group, a trifluoromethoxy group, a fluoroethoxy group, a difluoroethoxy group, a trifluoroethoxy group, a fluoropropoxy group, a difluoropropoxy group, a trifluoropropoxy group, a fluorobutoxy group, a difluorobutoxy group, a trifluorobutoxy group, a fluoropentyloxy group, a difluoropentyloxy group, a trifluoropentyloxy group, a fluorohexyloxy group, a difluorohexyloxy group, a trifluorohexyloxy group, a pentafluoroethoxy group, a hexafluoropropoxy group, a nonafluorobutoxy group, a chloromethoxy group, a dichloromethoxy group, a trichloromethoxy group, a chloroethoxy group, a dichloroethoxy group, a trichloroethoxy group, a chloropropoxy group, a dichloropropoxy group, or a trichloropropoxy group.

A C3-C6 cycloalkyl group:
A cyclic alkyl group having a carbon number of 3 to 6. It is preferably a cyclopropyl group, a cyclobutyl group, a cyclopentyl group, or a cyclohexyl group.

A C3-C6 cycloalkoxy group:
A group in which an oxygen atom is bound to the aforementioned C3-C6 cycloalkyl group. It is preferably a cyclopropyloxy group, a cyclobutyloxy group, a cyclopentyloxy group, or a cyclohexyloxy group.

A C1-C6 alkoxy C1-C6 alkyl group:
A group in which the aforementioned C1-C6 alkyl group is bound to the aforementioned C1-C6 alkoxy group. It is preferably a methoxymethyl group, a methoxyethyl group, an ethoxymethyl group, an ethoxyethyl group, a propoxyethyl group, an ethoxypropyl group, or a propoxypropyl group.

A C1-C6 alkoxy C1-C6 alkoxy group:
A group in which the aforementioned C1-C6 alkoxy group is bound to the aforementioned C1-C6 alkoxy group. It is preferably a methoxymethoxy group, a methoxyethoxy group, an ethoxymethoxy group, an ethoxyethoxy group, an ethoxypropoxy group, or a propoxypropoxy group.

A di C1-C6 alkylamino group:
A group in which two of the aforementioned C1-C6 alkyl groups are bound to an amino group. It is preferably a dimethylamino group.

A di C1-C6 alkylaminocarbonyl group:
A group in which two of the aforementioned C1-C6 alkyl groups are bound to an aminocarbonyl group. It is preferably a dimethylaminocarbonyl group.

A di C1-C6 alkylaminocarbonyloxy group:
A group in which an oxygen atom is bound to the aforementioned C1-C6 alkylaminocarbonyl group. It is preferably a dimethylaminocarbonyloxy group.

A di C1-C6 alkylaminosulfonyl group:
A group in which two of the aforementioned C1-C6 alkyl groups are bound to an aminosulfonyl group. It is preferably a dimethylaminosulfonyl group.

A di C1-C6 alkylphosphonate ester group:
A group in which a phosphonic acid is bound to the aforementioned C1-C6 alkyl group. It is preferably diethyl phosphonate.

A 5- to 6-membered heterocyclic group:
An azetidinyl group, a pyrrolidinyl group, a piperidinyl group, a morpholinyl group, a piperazinyl group, an azepanyl group, a 1,4-diazepanyl group, a pyrrolyl group, a thiazolyl group, a pyridyl group, a tetrahydropyridyl group, a tetrahydropyranyl group, a tetrahydrofuranyl group, a tetrahydroisoquinolinyl group, or a decahydroisoquinolinyl group.

Preferable substituents in the compound having the general formula (I) are as follows:
$R^1$: a hydroxyl group, a halogen group, a halogeno C1-C6 alkyl group, a halogeno C1-C6 alkoxy group, a di C1-C6 alkylaminocarbonyloxy group, a C1-C6 alkylamino group optionally substituted by groups selected from the substituent group β,
a piperazinyl group optionally substituted by groups selected from the substituent group β,
a tetrahydropyridinyl group optionally substituted by groups selected from the substituent group β,
a vinyl group optionally substituted by groups selected from the substituent group β,
a C1-C6 alkyl group optionally substituted by groups selected from the substituent group β,
a C1-C6 alkoxy group optionally substituted by groups selected from the substituent group β, or
a C1-C6 alkoxy C1-C6 alkoxy group optionally substituted by groups selected from the substituent group β,
$R^2$: a hydrogen atom or a halogen group,
$R^3$: a hydrogen atom, a methyl group, or an ethyl group, and
Z: —CH═ or —N═.

More preferable substituents are as follows:
$R^1$: a chlorine group, a fluorine group, a hydroxyl group, 4-morpholin-1-yl, 4-acetylpiperidin-1-yl, propan-2-yloxy, 2-hydroxyethoxy, 4-chloro-2-fluorophenyl, 2,4-difluorophenyl, difluoromethoxy, 2-(tetrahydro-2H-pyran-4-yloxy)ethoxy, or 2-(2-hydroxyethoxy)ethoxy,
$R^2$: a hydrogen atom, a chlorine group, or a fluorine group,
$R^3$: a hydrogen atom, and
Z: —CH═ or —N═.

Also, a compound having the general formula (I) is preferably a compound having the general formula (Ia), and preferable examples of the substituents in the compound having the general formula (Ia) are as follows:
$R^2$: a hydrogen atom or a halogen atom,
$R^3$: a hydrogen atom, a methyl group, or an ethyl group,
Z: —CH═ or —N═, and
$R^4$: a di C1-C6 alkylaminocarbonyl group,
a C1-C6 alkyl group optionally substituted by groups selected from the substituent group β, or
a C1-C6 alkoxy C1-C6 alkyl group optionally substituted by groups selected from the substituent group β.

Even more preferable examples of the substituents are as follows:
$R^2$: a hydrogen atom, a chlorine group, or a fluorine group,
$R^3$: a hydrogen atom,
Z: —CH═ or —N═, and
$R^4$: a C1-C6 alkyl group, a halogeno C1-C6 alkyl group, a 2-hydroxyethyl group, a 2-(tetrahydro-2H-pyran-4-yloxy) ethyl group, or a 2-(2-hydroxyethoxy)ethyl group.

Further, preferable compounds having the general formula (I) are the ones described in Examples, and the following compounds are particularly preferable.

8-[4-(morpholin-4-yl)phenyl]-1,6-naphthyridine-2-carboxamide,
4-[4-(4-acetylpiperazin-1-yl)phenyl]isoquinoline-6-carboxamide,
4-[4-(propan-2-yloxy)phenyl]isoquinoline-6-carboxamide,
8-[4-(2-hydroxyethoxy)phenyl]-1,6-naphthyridine-2-carboxamide,
4-[4-(2-hydroxyethoxy)phenyl]isoquinoline-6-carboxamide,
4-(4-chloro-2-fluorophenyl)isoquinoline-6-carboxamide,
4-(2,4-difluorophenyl)isoquinoline-6-carboxamide,
4-[4-(difluoromethoxy)phenyl]isoquinoline-6-carboxamide,
8-{4-[2-(tetrahydro-2H-pyran-4-yloxy)ethoxy]phenyl}-1,6-naphthyridine-2-carboxamide,
4-{4-[2-(tetrahydro-2H-pyran-4-yloxy)ethoxy]phenyl}isoquinoline-6-carboxamide,
N-methyl-8-{4-[2-(tetrahydro-2H-pyran-4-yloxy)ethoxy]phenyl}-1,6-naphthyridine-2-carboxamide,
N-methyl-4-{4-[2-(tetrahydro-2H-pyran-4-yloxy)ethoxy]phenyl}isoquinoline-6-carboxamide,
N-ethyl-8-{4-[2-(tetrahydro-2H-pyran-4-yloxy)ethoxy]phenyl}-1,6-naphthyridine-2-carboxamide,
8-{4-[2-(2-hydroxyethoxy)ethoxy]phenyl}-1,6-naphthyridine-2-carboxamide,
4-{4-[2-(2-hydroxyethoxy)ethoxy]phenyl}isoquinoline-6-carboxamide,
4-(4-chlorophenyl)isoquinoline-6-carboxamide,
4-(4-fluorophenyl)isoquinoline-6-carboxamide,
8-(4-hydroxyphenyl)-1,6-naphthyridine-2-carboxamide,
4-(4-hydroxyphenyl)isoquinoline-6-carboxamide,
8-(3-fluoro-4-hydroxyphenyl)-1,6-naphthyridine-2-carboxamide,
4-(1H-indol-5-yl)isoquinoline-6-carboxamide, and
4-(1-methyl-1H-indol-5-yl)isoquinoline-6-carboxamide.

The phrase "optionally substituted by" refers to either being unsubstituted or being substituted by one to three substituents.

The term "treatment" refers to curing diseases or symptoms.

The term "pharmacologically acceptable salt thereof" refers to a salt that can be used as a medicine. A compound of the present invention having an acidic group or a basic group can be obtained as a basic salt or an acidic salt through reaction with a base or an acid, respectively; therefore, such a salt is referred to as a "pharmacologically acceptable salt thereof."

Preferable examples of a pharmacologically acceptable "basic salt" of a compound of the present invention include an alkali metal salt such as a sodium salt, a potassium salt, and a lithium salt; an alkaline earth metal salt such as a magnesium salt and a calcium salt; an organic basic salt such as an N-methylmorpholine salt, a triethylamine salt, a tributylamine salt, a diisopropylethylamine salt, a dicyclohexylamine salt, an N-methylpiperidine salt, a pyridine salt, a 4-pyrrolidinopyridine salt, and a picoline salt; or an amino acid salt such as a glycine salt, a lysine salt, an arginine salt, an ornithine salt, a glutamic acid salt, and an aspartic acid salt, of which an alkali metal salt is preferable.

Preferable examples of a pharmacologically acceptable "acidic salt" of a compound of the present invention include a hydrohalide such as hydrofluoride, hydrochloride, hydrobromide, and hydroiodide, an inorganic acid salt such as nitrate, perchlorate, sulfate, and phosphate; an organic acid salt such as lower alkanesulfonate such as methanesulfonate, trifluoromethanesulfonate, and ethanesulfonate, arylsulfonate such as benzenesulfonate and p-toluenesulfonate, an organic acid salt such as acetate, malate, fumarate, succinate, citrate, ascorbate, tartrate, oxalate, and maleate; and an amino acid salt such as a glycine salt, a lysine salt, an arginine salt, an ornithine salt, a glutamic acid salt, and an aspartic acid salt, of which a hydrohalide, particularly a hydrochloride, is most preferable.

A compound of the present invention or a pharmacologically acceptable salt thereof may absorb water, contain hygroscopic water, or form a hydrate, when left in the atmosphere or subjected to recrystallization. The present invention also encompasses compounds in such various forms of hydrates, solvates, and crystal polymorphs.

A compound of the present invention, a pharmacologically acceptable salt thereof, or a solvate thereof may be present as various isomers such as geometric isomers including a cis-form, a trans-form, etc., tautomers, or enantiomers such as a D-form and an L-form, depending on the kind or combination of substituents. Unless otherwise specifically restricted, a compound of the present invention encompasses all of these isomers and stereoisomers, and a mixture containing these isomers and stereoisomers in any ratio. A mixture of these isomers can be separated by publicly known means of separation.

A compound of the present invention also encompasses a labeled compound, namely a compound of the present invention in which one or more atoms are substituted with isotopes (for example, $^2$H, $^3$H, $^{13}$C, $^{14}$C, and $^{35}$S).

Further, the present invention also encompasses so-called prodrugs of a compound of the present invention. A prodrug is a compound having a group that can be converted into an amino group, a hydroxyl group, a carboxyl group, and the like of the compound of the invention by hydrolysis or under physiological conditions. Examples of a group forming such a prodrug include ones described in Prog. Med., Vol. 5, pages 2157 to 2161, 1985; and "Iyakuhin no kaihatu" (literal translation: development of pharmaceutical product) (Hirokawa Shoten Ltd.) Vol. 7, Bunshi Sekkei (literal translation: molecular design) pages 163 to 198. More specifically, examples of a prodrug of a compound of the present invention having an amino group include a compound in which the amino group is acylated, alkylated, or phosphorylated (for example, the compound in which the amino group is converted into eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, and tert-butyl). Also, more specifically, examples of a prodrug of a compound of the present invention having a hydroxyl group include a compound in which the hydroxyl group is acylated, alkylated, phosphorylated, or borated (for example, the compound in which the hydroxyl group is converted into acetyl, palmitoyl, propanoyl, pivaloyl, succinyl, fumaryl, alanyl, and dimethylaminomethylcarbonyl). Also, more specifically, examples of a prodrug of a compound of the present invention having a carboxyl group include a compound in which the carboxyl group is esterified or amidated (for example, the compound in which the carboxyl group is ethyl-esterified, phenyl-esterified, carboxymethyl-esterified, dimethylaminomethyl-esterified, pivaloyloxymethyl-esterified, ethoxycarbonyloxyethyl-esterified, amidated, or methylamidated).

(Production Method)

A compound of the present invention can be produced by applying various publicly known production methods, while taking advantage of characteristics based on the basic structure of the compound or the kind of substituent. Examples of publicly known methods include methods described in "ORGANIC FUNCTIONAL GROUP PREPARATIONS", second edition, ACADEMIC PRESS, INC., 1989, and "Comprehensive Organic Transformations", VCH Publishers Inc., 1989, and the like.

Upon production of a compound of the present invention, depending on the kind of functional group, it may be effective, from the production technique point of view, to protect the functional group of a raw material or intermediate compound with an appropriate protective group or replace the functional group by a readily-convertible group in advance.

Examples of the functional group include an amino group, a hydroxyl group, and a carboxyl group, and examples of the protective group thereof include ones described in "Protective Groups in Organic Synthesis (third edition, 1999)" written by T. W. Greene and P. G. Wuts. These protective groups can be appropriately selected in accordance with their reaction conditions. According to these methods, a desired compound can be obtained by introducing the substituent and carrying out the reaction, and then removing the protective group or converting the substituent into a desired group, as needed.

Further, a prodrug of a compound of the present invention can be produced by, similarly to the aforementioned protective groups, introducing a specific group into a raw material or intermediate compound, or carrying out the reactions using the compound of the present invention produced. The reaction can be carried out by applying a method publicly known to those skilled in the art such as methods normally performed, for example, esterification, amidation, dehydration, and hydrogenation.

Hereinbelow, the production method of the compound of the present invention will be described. However, the production method is not limited to the below-described methods in any way.

[Chemical formula 3]

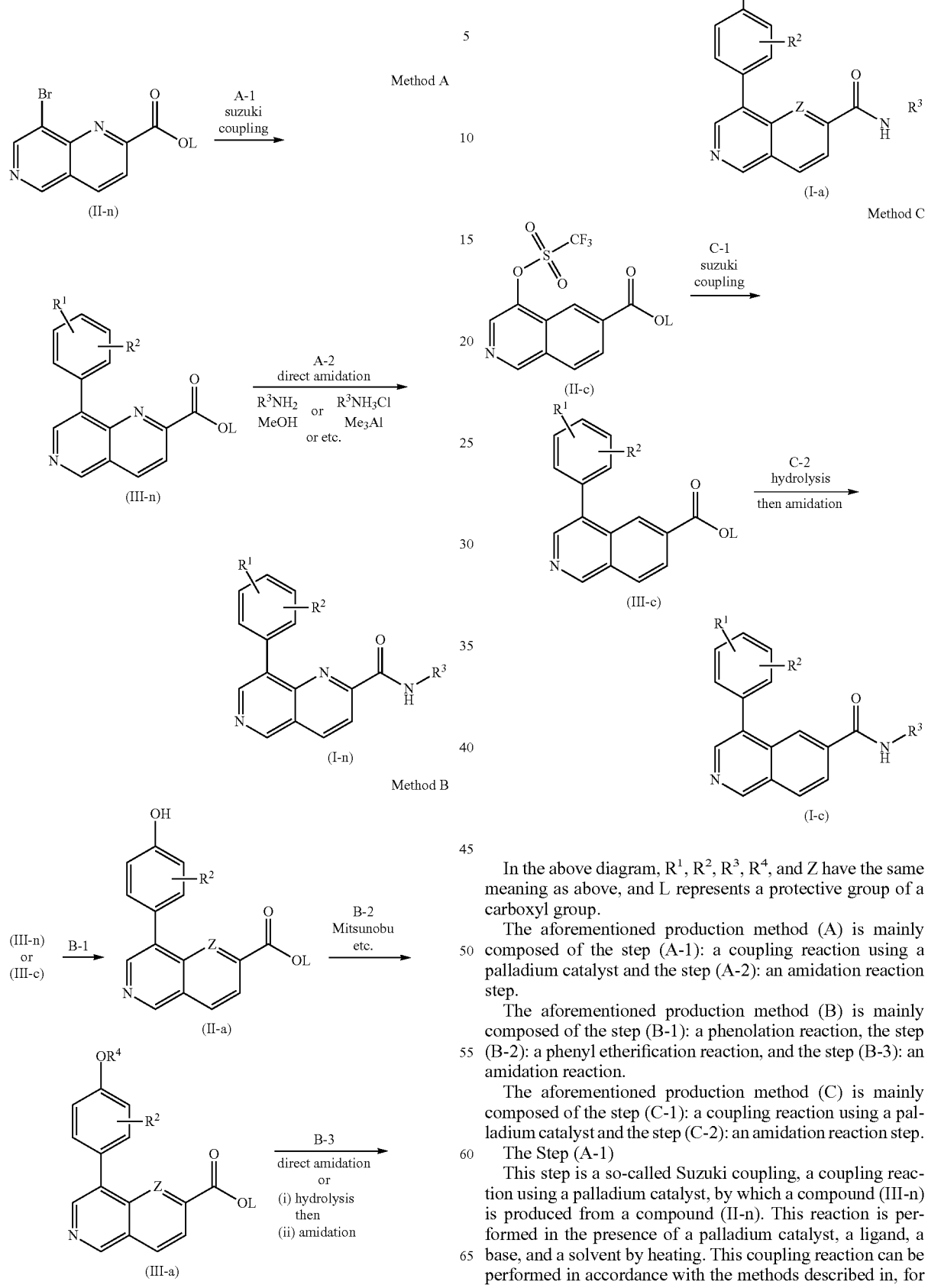

In the above diagram, $R^1$, $R^2$, $R^3$, $R^4$, and Z have the same meaning as above, and L represents a protective group of a carboxyl group.

The aforementioned production method (A) is mainly composed of the step (A-1): a coupling reaction using a palladium catalyst and the step (A-2): an amidation reaction step.

The aforementioned production method (B) is mainly composed of the step (B-1): a phenolation reaction, the step (B-2): a phenyl etherification reaction, and the step (B-3): an amidation reaction.

The aforementioned production method (C) is mainly composed of the step (C-1): a coupling reaction using a palladium catalyst and the step (C-2): an amidation reaction step.

The Step (A-1)

This step is a so-called Suzuki coupling, a coupling reaction using a palladium catalyst, by which a compound (III-n) is produced from a compound (II-n). This reaction is performed in the presence of a palladium catalyst, a ligand, a base, and a solvent by heating. This coupling reaction can be performed in accordance with the methods described in, for example, Tetrahedron Letters, 32, 20, 1991, 2273-2276, Tetrahedron, 49, 43, 1993, 9713-9720, Synthesis, 18, 2007, 2853-2861, Angewandte Chemie, International Edition, 46, 17, 2007, 3135-3138, Journal of the American Chemical Society, 116, 15, 1994, 6985-6986, Heterocycles, 26, 10, 1987, 2711-2716, Synthetic Communications, 30, 19, 2000, 3501-3510, Tetrahedron Letters, 42, 37, 2001, 6523-6526, Tetrahedron Letters, 42, 33, 2001, 5659-5662, Journal of Organic Chemistry, 68, 24, 2003, 9412-9415, Journal of Organic Chemistry, 68, 20, 2003, 7733-7741, Journal of Organic Chemistry, 70, 6, 2005, 2191-2194, Synlett, 13, 2005, 2057-2061, European Journal of Organic Chemistry, 8, 2006, 1917-1925, Organic Letters, 8, 16, 2006, 3605-3608, Journal of Organic Chemistry, 71, 10, 2006, 3816-3821, Chemistry A European Journal, 12, 19, 2006, 5142-5148, Organic Letters, 5, 6, 2003, 815-818, and Journal of Organic Chemistry, 73, 4, 2008, 1429-1434.

The Step (A-2)

This is a step for converting the compound (III-n) into a compound (I-n) by an amidation reaction. This amidation reaction can be performed in accordance with the methods described in, for example, Chem. Rev., 1948, 45, 203, J. Am. Chem. Soc., 1950, 72, 1888, Org. Biol. Chem., 1962, 84, 4457, J. Am. Chem. Soc., 1973, 95, 875, and J. Am. Chem. Soc., 1981, 103, 7090.

The Step (B-1)

This is a step for converting the compound (III-n) or (III-c) produced through the step (A-1) or (C-1) into a compound (II-a). Although a phenolic hydroxyl group is protected with a protective group in the compound (III-n) or (III-c), this step removes the protective group. The deprotection of the phenolic hydroxyl group can be performed in accordance with, for example, the methods described in "Protective Groups in Organic Synthesis (third edition, 1999)" written by T. W. Greene and P. G. Wuts.

The Step (B-2)

This step is a so-called Mitsunobu reaction, a condensation reaction by which the compound (II-a) is converted into a compound (III-a) to form a phenyl ether.

The Step (B-3)

This is a step for converting the compound (III-a) into a compound (I-a) by an amidation reaction. There are two methods for this amidation reaction step; a method of directly converting an ester group into an amide group similarly to the step (A-2) or a method in which an ester group is hydrolyzed and then amidated by a condensation reaction with amine.

The Step (C-1)

This step is a so-called Suzuki coupling, a coupling reaction using a palladium catalyst, by which a compound (III-c) is produced from a compound (II-c). This step can be performed similarly to the step (A-1).

The Step (C-2)

This is a step for converting the compound (III-c) into a compound (I-c) by an amidation reaction. This amidation reaction can be performed similarly to the step (B-3).

A compound of the present invention produced by the aforementioned method can be isolated and purified by a publicly known method, for example, extraction, precipitation, distillation, chromatography, fractional crystallization, and recrystallization.

Also, in the case that the compound having the general formula (I) of the present invention or a production intermediate thereof contains asymmetric carbon, enantiomers exist. Each of these enantiomers can be isolated and purified by standard methods such as fractional crystallization (salt fractionation) in which an enantiomer is recrystallized with an appropriate salt, and column chromatography. Examples of reference literature for a method of separating an enantiomer from racemates include J. Jacques et al., "Enantiomers, Racemates and Resolution, John Wiley And Sons, Inc."

The compound of the present invention has low toxicity and exhibits favorable disposition, and also, has an excellent osteogenesis-promoting action. Hence, the compound of the present invention can be used for the prevention or treatment (particularly, treatment) of diseases associated with bone metabolism such as osteoporosis, Paget's disease of bone, and osteoarthritis, and thus is useful.

When administering the compound of the present invention or a pharmacologically acceptable salt thereof to a mammal (particularly, a human), it can be administered systemically or locally by the oral or parenteral route.

The dosage form of a pharmaceutical composition of the present invention is selected depending on the administration method, and is producible by preparation methods normally employed for various kinds of formulations.

Examples of dosage forms for an oral pharmaceutical composition include a tablet, a pill, a powder, a granule, a capsule, a liquid medicine, a suspension, an emulsion, a syrup, and an elixir. Medicines in these dosage forms can be prepared by standard methods, using any agent appropriately selected as needed from among those normally employed as additives such as an excipient, a binder, a disintegrant, a lubricant, a swelling agent, a swelling aid, a coating agent, a plasticizer, a stabilizer, an antiseptic, an antioxidant, a colorant, a solubilizing aid, a suspending agent, an emulsifier, a sweetener, a preservative, a buffer, a diluent, and a humectant.

Examples of dosage forms for a parenteral pharmaceutical composition include an injection, an ointment, a gel, a cream, a poultice, an aerosol, an inhalant, a spray, an eye drop, a nasal drop, and a suppository. Medicines in these dosage forms can be prepared by standard methods, using any agent appropriately selected as needed from among those normally employed as additives such as a stabilizer, an antiseptic, a solubilizing aid, a humectant, a preservative, an antioxidant, a fragrance, a gelling agent, a neutralizer, a solubilizing aid, a buffer, an isotonic agent, a surfactant, a colorant, a buffer, a viscosity enhancer, a humectant, a filler, an absorption promoter, a suspending agent, and a binder.

The dose of a compound having the general formula (I) or a pharmacologically acceptable salt thereof varies depending on the symptoms, age, body weight, and the kind, dose, etc. of the drug to be administered in combination. However, normally, a compound having the general formula (I) or a pharmacologically acceptable salt thereof is preferably administered in a range of 0.001 mg to 1000 mg, in terms of the amount of the compound having the general formula (I), per adult (presumed to weigh approximately 60 kg) per dose, systemically or locally, once to several times a month, once to several times a week, or once to several times a day, orally or parenterally, or via the intravenous route continuously for one to 24 hours a day.

Other active ingredients can be used in combination with a pharmaceutical composition of the present invention as needed as long as such active ingredient does not impair the efficacy of the present invention.

The present invention also encompasses a method for preventing/treating the aforementioned diseases, comprising administering a compound of the present invention or a pharmacologically acceptable salt thereof.

The present invention further encompasses use of a compound of the present invention or a pharmacologically acceptable salt thereof for the production of the aforementioned pharmaceutical composition.

Formulation Example 1

Powder

Five grams of a compound of the present invention, 895 g of lactose, and 100 g of corn starch are mixed by a blender to give a powder.

Formulation Example 2

Granule

Five grams of a compound of the present invention, 865 g of lactose, and 100 g of low-substituted hydroxypropylcellulose are mixed, followed by addition of 300 g of a 10% aqueous solution of hydroxypropylcellulose. The resulting mixture is kneaded and granulated using extrusion granulation equipment, and then dried to give a granule.

Formulation Example 3

Tablet

Five grams of a compound of the present invention, 90 g of lactose, 34 g of corn starch, 20 g of crystalline cellulose, and 1 g of magnesium stearate are mixed by a blender, followed by tabletting using a tablet machine to give a tablet.

TEST EXAMPLE

Test Example 1

Osteoblast Differentiation Test

ST2 cells, murine bone marrow-derived stromal cells, (obtained from RIKEN) were used.

In this test, α-MEM media (obtained from GIBCO BRL Cat. No. 10370-021) containing 10% (v/v) of inactivated calf serum (obtained from Hyclone Laboratories, Inc.) and 1% (v/v) of Penicillin-Streptomycin Liquid (obtained from GIBCO BRL Cat. No. 15140-122) (hereinbelow, abbreviated as 10%-FBS-αMEM) were used. In this test, all culturing was performed in a $CO_2$ incubator (37° C., 95% humidity, 5% $CO_2$).

The aforementioned cells were detached with 2 mL of a 0.25% trypsin solution (obtained from GIBCO BRL Cat. No. 15050-065) and dispersed in 10 mL of 10%-FBS-αMEM. Subsequently, the cells were collected by centrifugation (25° C., 800 rpm, five minutes). Then, a cell suspension containing 40000 of the cells/mL of 10%-FBS-αMEM was prepared. The cell suspension was then dispensed into 96-well plates (the product of Falcon), 100 μL per well, at a density of 4000 cells/well, followed by culturing for 24 hours. To the wells, except for the below-described well containing a control group, the compound was dispensed at final concentrations of 0.01, 0.03, 0.1, and 0.3 μg/ml. To the well of a control group, DMSO was dispensed at a final concentration of 0.1% (v/v). After four days of culturing, the activity of alkaline phosphatase (ALP) was measured in each group.

The measurement of ALP activity was performed as follows. That is, the medium in each well of the culture plates was completely removed. Each well was then washed by dispensing 100 μL of Dulbecco's phosphate buffer (obtained from GIBCO BRL Cat. No. 14190-144) and then removing it. A cell lysate solution containing 10 mM $MgCl_2$ and 2% (v/v) TritonX-100 (Sigma) was prepared and dispensed at 50 μL/well, followed by stirring at room temperature for five minutes. An ALP substrate solution containing 50 mM diethanolamine (Wako Pure Chemical Industries, Ltd., Cat. No. 099-03112) and 20 mM p-nitrophenyl phosphate (Wako Pure Chemical Industries, Ltd., Cat. No. 147-02343) was prepared and dispensed at 50 μL/well, and the plates were left to stand at room temperature for 10 minutes. Subsequently, absorbance was measured by a microplate reader (Bio-Rad Laboratories, Inc.). Setting the measurement value of the control group of each plate at 100%, the increase (%) in alkaline phosphatase activity in the test compound-addition group was calculated, which was assessed as the degree of osteoblast differentiation.

In this test, the compounds of Examples 1 to 105, 107 to 109, and 111 to 118 exhibited an increase of 200% or more in alkaline phosphatase activity at 0.03 μg/mL.

Test Example 2

Osteoclast Formation-Inhibition Test

Eighteen day-old ICR mice are purchased from Japan SLC, Inc. and used in the following experiment. Mice are sacrificed by cervical dislocation, and the left and right femur and the tibia are excised. After removal of surrounding tissues, the femur and the tibia thus excised are minced with scissors. To the femur and the tibia thus minced, 10 mL of 15%-FBS-αMEM is added, followed by stirring for one minute. Subsequently, the supernatant is collected, which is filtered through a cell strainer (Becton, Dickinson and Company). Then, a suspension of 500 thousand cells/mL of 15%-FBS-αMEM was prepared. The cell suspension is then dispensed into 96-well microplates, 100 μL per well, at a density of 50000 cells/well, followed by culturing for 24 hours. Activated vitamin D3 (Sigma, Cat. No. D1530) is dispensed into each well at a final concentration of 20 nM. To the wells, except for the below-described well containing a control group, the compound is dispensed at final concentrations of 0.01, 0.03, 0.1, and 0.3 μg/ml. To the well of a control group, DMSO is dispensed at a final concentration of 0.1% (v/v). After five days of culturing, the activity of tartrate-resistant acid phosphatase (TRAP) is measured in each group.

The measurement of TRAP activity is performed as follows. That is, the medium in each well of the culture plates is completely removed. Each well is then washed by dispensing 100 μL of Dulbecco's phosphate buffer (obtained from GIBCO BRL Cat. No. 14190-144) and then removing it. An acetone:ethanol mixture (1:1) is added to the wells and left for one minute for fixation. The fixation mixture is then removed and staining is performed using a Leukocyte acid phosphatase kit (Sigma, Cat. No. 387-A) at 37° C. for 30 minutes. After removing the staining liquid, 100 μL of 10% sodium dodecyl sulfate (Wako Pure Chemical Industries, Ltd. Cat. No. 191-07145) is dispensed, followed by stirring for five minutes. Subsequently, absorbance is measured by a microplate reader (Bio-Rad Laboratories, Inc.). Setting the measurement value of the control group of each plate at 100%, the decrease (%) in TRAP activity in the test compound-addition group is calculated, which is assessed as the osteoclast formation-inhibiting activity.

Test Example 3

Effect on Bone Density

Eight to 12 week old female F344 rats were purchased from Charles River Laboratories and used in the following experiment. Rats were anesthetized with an intraperitoneal administration of 40 mg/kg of Somnopentyl (Kyoritsu Seiyaku Corporation), and then oophorectomy or sham surgery was performed. From the day after surgery, a suspension of the test compound in a 0.5% methyl cellulose solution (Wako Pure Chemical Industries, Ltd. Cat. No. 133-14255) was orally administered once a day, six days a week. Six weeks after administration, the rats were euthanized by removal of whole blood from the lower abdominal aorta under Somnopentyl anesthesia, and the left and right femur was excised.

After removal of soft tissues, the bone density of the femur thus excised was measured by a DXA apparatus, DCS-600R (Aloka Co., Ltd.). The bone density was assessed in the whole femur as well as in three equal sections of the whole femur, namely the proximal end, the shaft, and the distal end.

In this test, the compounds of Examples 9, 33, 36, and 118 significantly increased the bone density at 3 mg/kg or less.

Test Example 4

Effect on Healing of Fracture

Twelve week old female F344 rats are purchased from Charles River Laboratories and used in the following experiment. Under anesthesia with Somnopentyl, bone surgery is performed in accordance with the method of Li et al. (J. Bone Miner. Res 1999, 14: 969 to 979). From the day after surgery, a suspension of the test compound in a 0.5% methyl cellulose solution (Wako Pure Chemical Industries, Ltd. Cat. No. 133-14255) was orally administered once a day, six days a week. Six weeks after administration, the rats are euthanized by removal of whole blood from the lower abdominal aorta under Somnopentyl anesthesia, and the femur was excised.

After removal of soft tissues, the bone density of the femur thus excised was measured by a bone strength measuring instrument, MZ-500D (Maruto Instrument Co., Ltd.) A three-point bending test is performed, and the strength is assessed at the maximum load.

EXAMPLES

Example 1

8-(3-Fluoro-4-hydroxyphenyl)-1,6-naphthyridine-2-carboxamide

[Chemical formula 4]

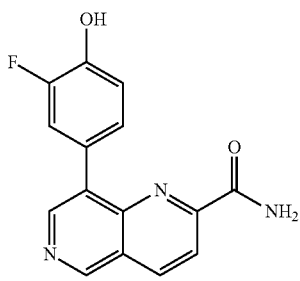

(1a) Ethyl 8-(3-fluoro-4-hydroxyphenyl)-1,6-naphthyridine-2-carboxylate

With respect to ethyl 8-bromo-1,6-naphthyridine-2-carboxylate (9.89 g, 35.2 mmol), bis(triphenylphosphine)palladium chloride (2.47 g, 3.52 mmol), and potassium carbonate (14.6 g, 106 mmol), 2-[4-(methoxymethoxy)-3-methylphenyl]-4,4,5,5-tetramethyl-1,3,2-dioxaborolane (12.9 g, 45.7 mmol) was added to ethanol (300 mL) while dissolving, to which water (2.53 mL) was further added. The resulting reaction liquid was stirred at 90° C. for one hour under a nitrogen atmosphere. After cooling, ethanol (300 mL) and concentrated sulfuric acid (32 mL) were added, followed by stirring at 90° C. for 45 minutes.

After cooling, the reaction liquid was slowly added to a suspension of saturated aqueous sodium bicarbonate and ethyl acetate. A solid precipitated, which was collected by filtration and dried to give the desired title compound (8.42 g, yield 77%).

$^1$H-NMR (DMSO-D$_6$) δ: 1.38 (3H, t, J=7.1 Hz), 4.41 (2H, q, J=7.1 Hz), 7.08-7.13 (1H, m), 7.52-7.55 (1H, m), 7.85 (1H, dd, J=13.1, 2.1 Hz), 8.28 (1H, d, J=8.5 Hz), 8.84 (1H, d, J=8.5 Hz), 8.92 (1H, s), 9.48 (1H, s).

MS(ESI) m/z: 313 (M+H)$^+$ (1b) 8-(3-Fluoro-4-hydroxyphenyl)-1,6-naphthyridine-2-carboxamide Ethyl 8-(3-fluoro-4-hydroxyphenyl)-1,6-naphthyridine-2-carboxylate (100 mg, 0.32 mmol) synthesized in Example 1 (1a) was dissolved in a 7M ammonia-methanol solution (10 mL), followed by stirring while heating at 80° C. for three hours. After cooling the resulting reaction liquid to room temperature, a precipitated solid was collected by filtration to give the desired title compound (51 mg, yield 56%).

$^1$H-NMR (DMSO-D$_6$) δ: 7.12 (1H, t, J=8.9 Hz), 7.48-7.53 (1H, m), 7.65 (1H, br s), 7.69 (1H, dd, J=12.8, 2.1 Hz), 7.99 (1H, br s), 8.29 (1H, d, J=8.5 Hz), 8.82 (1H, d, J=8.5 Hz), 8.87 (1H, s), 9.47 (1H, s).

MS(FAB) m/z: 284 (M+H)$^+$

Example 2

8-(3-Fluoro-4-{2-[2-(2-hydroxyethoxy)ethoxy]ethoxy}phenyl)-1,6-naphthyridine-2-carboxamide

[Chemical formula 5]

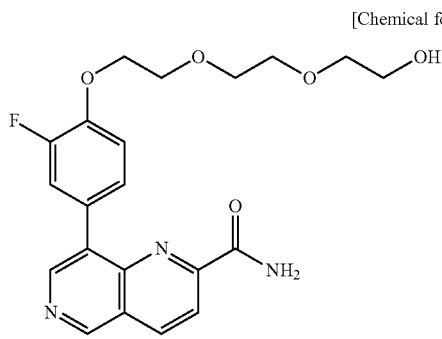

(2a) Ethyl 8-[3-fluoro-4-(2-{2-[2-(tetrahydro-2H-pyran-2-yloxy)ethoxy]ethoxy}ethoxy)phenyl]-1,6-naphthyridine-2-carboxylate Ethyl 8-(3-fluoro-4-hydroxyphenyl)-1,6-naphthyridine-2-carboxylate (300 mg, 0.961 mmol) synthesized in Example 1 (1a) and 2-{2-[2-(tetrahydro-2H-pyran-2-yloxy)ethoxy]ethoxy}ethanol (338 mg, 1.44 mmol) were dissolved in toluene (3.0 mL), to which a solution of cyanomethylenetributylphosphorane (348 mg, 1.44 mmol) in toluene (3.0 mL) was added, followed by stirring at 80° C. for one hour under a nitrogen atmosphere.

The resulting reaction liquid was concentrated under reduced pressure, and the residue thus obtained was purified by silica gel column chromatography (hexane:ethyl acetate, 75:25-30:70, V/V) to give the desired title compound (353 mg, yield 70%).

$^1$H-NMR (CDCl$_3$) δ: 1.48 (3H, t, J=7.1 Hz), 1.49-1.65 (2H, m), 1.69-1.76 (2H, m), 1.79-1.88 (2H, m), 3.47-3.53 (1H, m), 3.60-3.66 (1H, m), 3.70-3.75 (4H, m), 3.77-3.80 (2H, m), 3.85-3.91 (2H, m), 3.94-3.97 (2H, m), 4.29-4.32 (2H, m), 4.49 (2H, q, J=7.1 Hz), 4.63-4.66 (1H, m), 7.15 (1H, t, J=8.7 Hz), 7.60-7.63 (1H, m), 7.88 (1H, dd, J=12.8, 2.3 Hz), 8.31 (1H, d, J=8.3 Hz), 8.50 (1H, d, J=8.3 Hz), 8.93 (1H, s), 9.32 (1H, s).

MS(FAB) m/z: 529 (M+H)$^+$ (2b) 8-[3-Fluoro-4-(2-{2-[2-(tetrahydro-2H-pyran-2-yloxy)ethoxy]ethoxy}ethoxy)phenyl]-1,6-naphthyridine-2-carboxamide Using ethyl 8-[3-fluoro-4-(2-{2-[2-(tetrahydro-2H-pyran-2-yloxy)ethoxy]ethoxy}ethoxy)phenyl]-1,6-naphthyridine-2-carboxylate (353 mg, 0.668 mmol) synthesized in Example 2 (2a), a crude desired title compound was obtained by the same method as in Example 1 (1a), which was directly used in the following reaction without purification.

(2c) 8-(3-Fluoro-4-{2-[2-(2-hydroxyethoxy)ethoxy]ethoxy}phenyl)-1,6-naphthyridine-2-carboxamide Into methanol (7.0 mL), 8-[3-fluoro-4-(2-{2-[2-(tetrahydro-2H-pyran-2-yloxy)ethoxy]ethoxy}ethoxy)phenyl]-1,6-naphthyridine-2-carboxamide synthesized in Example 2 (2b) was dissolved, to which p-toluenesulfonic acid monohydrate was added at 0° C., followed by stirring overnight at room temperature.

To the resulting reaction liquid, saturated aqueous sodium bicarbonate was added for neutralization, and the resulting liquid was directly concentrated under reduced pressure. Chloroform and water were added to the residue thus obtained, followed by extraction with chloroform. The resulting organic layer was dried over sodium sulfate and then filtered, and the filtrate was concentrated under reduced pressure. The residue thus obtained was purified by silica gel column chromatography (hexane:ethyl acetate, 30:70-0:100, V/V, ethyl acetate:methanol, 100:0-90:10, V/V) to give the desired title compound (110 mg, yield 40% (2 steps)).

$^1$H-NMR (DMSO-D$_6$) δ: 3.42-3.46 (2H, m), 3.47-3.52 (2H, m), 3.55-3.59 (2H, m), 3.62-3.66 (2H, m), 3.80-3.84 (2H, m), 4.26-4.30 (2H, m), 4.60 (1H, t, J=5.5 Hz), 7.36 (1H, t, J=8.7 Hz), 7.61-7.64 (1H, m), 7.66 (1H, br s), 7.78 (1H, dd, J=12.8, 1.8 Hz), 8.01 (1H, br s), 8.30 (1H, d, J=8.7 Hz), 8.84 (1H, d, J=8.7 Hz), 8.88 (1H, s), 9.49 (1H, s).

MS(FAB) m/z: 416 (M+H)$^+$

Example 3

4-{2-[4-(2-Carbamoyl-1,6-naphthyridin-8-yl)-2-fluorophenoxy]ethoxy}benzoic acid hydrochloride

[Chemical formula 6]

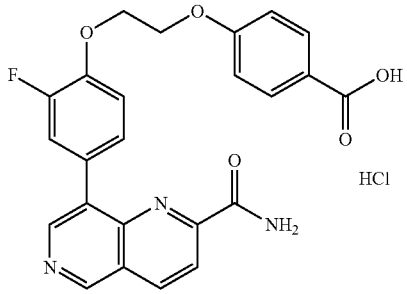

Tert-butyl 4-{2-[4-(2-carbamoyl-1,6-naphthyridin-8-yl)-2-fluorophenoxy]ethoxy}benzoate (174 mg, 0.346 mmol) was synthesized from ethyl 8-(3-fluoro-4-hydroxyphenyl)-1,6-naphthyridine-2-carboxylate synthesized in Example 1 (1a) and tert-butyl 4-(2-hydroxyethoxy)benzoate synthesized in Reference Example 9 by the same methods as in Example 2 (2a) and (2b), and then dissolved in 1,4-dioxane (1.0 mL). To the resulting mixture, a 4M HCl/1,4-dioxane solution (8.0 mL) was added at 0° C., followed by stirring overnight.

The resulting reaction liquid was concentrated under reduced pressure. To the residue thus obtained, methanol was added to produce a suspension, and the residue was collected by filtration. The solid thus obtained was dried to give the desired title compound (116 mg, yield 70%).

$^1$H-NMR (DMSO-D$_6$) δ: 4.47-4.55 (4H, m), 7.11 (2H, d, J=8.8 Hz), 7.44 (1H, t, J=8.5 Hz), 7.64-7.68 (2H, m), 7.69 (1H, br s), 7.81 (1H, dd, J=12.6, 2.1 Hz), 7.92 (2H, d, J=8.8 Hz), 8.03 (1H, br s), 8.33 (1H, d, J=8.6 Hz), 8.87 (1H, d, J=8.6 Hz), 8.91 (1H, s), 9.55 (1H, s).

MS(FAB) m/z: 448 (M+H)$^+$

Example 4

4-{4-[2-(Tetrahydro-2H-pyran-4-yloxy)ethoxy]phenyl}isoquinoline-6-carboxamide

[Chemical formula 7]

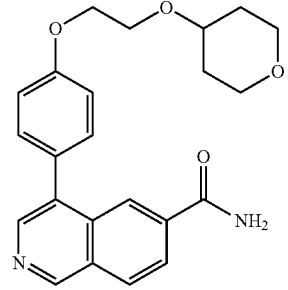

(4a) 2-(Trimethylsilyl)ethyl {4-[2-(tetrahydro-2H-pyran-4-yloxy)ethoxy]phenyl}isoquinoline-6-carboxylate Into toluene (10 ml), 2-(trimethylsilyl)ethyl 4-{[(trifluoromethyl)sulfonyl]oxy}isoquinoline-6-carboxylate (500 mg, 1.2 mmol) was dissolved, to which 4-{2-[4-(4,4,5,5-tetramethyl-1,3,2-dioxaborolan-2-yl)phenoxy]ethoxy}tetrahydro-2H-pyran (630 mg, 1.8 mmol) synthesized in Reference Example 2, 4,5-bis(diphenylphosphino)-9-dimethylxanthene (210 mg, 0.36 mmol), tris(dibenzylideneacetone)palladium (160 mg, 0.17 mmol), and potassium carbonate (500 mg, 3.6 mmol) were added. The resulting mixture was stirred at 100° C. for four hours, to which ethyl acetate was added. The resulting mixture was sequentially washed with water and saturated brine, and then dried over anhydrous sodium sulfate and concentrated under reduced pressure. The residue thus obtained was purified by silica gel column chromatography (hexane:ethyl acetate, 100:0-50:50, V/V) to give the desired title compound (307 mg, yield 52%).

¹H-NMR (CDCl₃) δ: 0.07 (9H, s), 1.13 (2H, t, J=8.4 Hz), 1.63-1.73 (2H, m), 1.90-2.02 (2H, m), 3.44-3.52 (2H, m), 3.61-3.69 (1H, m), 3.91 (2H, t, J=5.0 Hz), 3.96-4.02 (2H, m), 4.24 (2H, t, J=5.0 Hz), 4.46 (2H, t, J=8.4 Hz), 7.11 (3H, d, J=8.8 Hz), 7.44 (2H, d, J=8.8 Hz), 8.09 (1H, d, J=8.5 Hz), 8.21 (1H, d, J=8.5 Hz), 8.55 (1H, s), 8.66 (1H, s), 9.29 (1H, s).

(4b) 4-{4-[2-(Tetrahydro-2H-pyran-4-yloxy)ethoxy]phenyl}isoquinoline-6-carboxamide Into tetrahydrofuran (5 ml), 2-(trimethylsilyl)ethyl [4-(2-2-(tetrahydro-2H-pyran-4-yloxy)ethoxy)phenyl]isoquinoline-6-carboxylate (305 mg, 0.62 mmol) synthesized in Example 4 (4a) was dissolved, to which a solution of 1 M tetrabutylammonium fluoride in tetrahydrofuran (1.2 ml, 1.2 mmol) was added. The resulting mixture was stirred at room temperature for two hours and then concentrated under reduced pressure. The residue thus obtained was dissolved in dimethylformamide (10 ml), to which ammonium chloride (660 mg, 12.3 mmol), 1-ethyl-3-(3-dimethylaminopropyl)-carbodiimide hydrochloride (590 mg, 3.1 mmol), 1-hydroxy-1H-benzotriazole monohydrate (470 mg, 3.1 mmol), and triethylamine (2.1 ml, 15.1 mmol) were added. The resulting mixture was stirred overnight at room temperature, to which water was added, followed by extraction with dichloromethane three times. The resulting organic layer was collected and washed with saturated brine, and then dried over anhydrous sodium sulfate. The solvent was distilled off under reduced pressure. The residue thus obtained was purified by silica gel column chromatography (ethyl acetate:methanol, 100:0-95:5, V/V) and recrystallized from methanol-ethyl acetate-hexane to give the desired title compound (108 mg, yield 45%).

¹H-NMR (DMSO-D₆) δ: 1.37-1.50 (2H, m), 1.85-1.95 (2H, m), 3.34-3.42 (2H, m), 3.56-3.65 (1H, m), 3.79-3.87 (4H, m), 4.18-4.24 (2H, m), 7.17 (2H, d, J=8.4 Hz), 7.50 (2H, d, J=8.4 Hz), 7.62 (1H, br s), 8.11 (1H, d, J=8.5 Hz), 8.23 (1H, br s), 8.28 (1H, d, J=8.5 Hz), 8.38 (1H, s), 8.47 (1H, s), 9.38 (1H, s).

MS(FAB) m/z 393 (M+H)⁺

Example 5

4-(4-Methoxyphenyl)isoquinoline-6-carboxamide

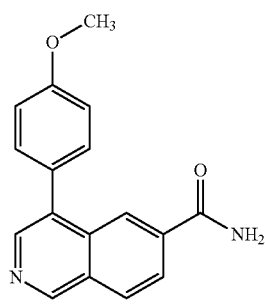

[Chemical formula 8]

Under a nitrogen atmosphere, ammonium chloride (133 mg, 2.49 mmol) was suspended in toluene (2.0 mL), to which trimethylaluminium (a 2.0 M toluene solution, 1.13 mL, 2.26 mmol) was added dropwise at 0° C. The mixture was warmed to room temperature, followed by stirring for one hour. Then, 2-(trimethylsilyl)ethyl 4-(4-methoxyphenyl)isoquinoline-6-carboxylate (172 mg, 0.452 mmol) synthesized from 2-(trimethylsilyl)ethyl 4-{[(trifluoromethyl)sulfonyl]oxy}isoquinoline-6-carboxylate by the same method as in Example 4 (4a) was added to the reaction liquid while dissolving into toluene (2.0 mL), followed by stirring at 50° C. for three and a half hours.

After cooling to 0° C., sodium sulfate decahydrate was added, followed by stirring at room temperature. A solid precipitate was filtered off. The filtrate was concentrated under reduced pressure, and the residue thus obtained was purified by basic silica gel column chromatography (hexane:ethyl acetate, 100:0-90:10, V/V, ethyl acetate:methanol, 100:0-98:2, V/V) to give the desired title compound (51 mg, yield 40%).

¹H-NMR (DMSO-D₆) δ: 3.87 (3H, s), 7.16 (2H, d, J=8.7 Hz), 7.51 (2H, d, J=8.7 Hz), 7.60 (1H, br s), 8.11 (1H, d, J=8.5 Hz), 8.23 (1H, br s), 8.28 (1H, d, J=8.5 Hz), 8.38 (1H, s), 8.47 (1H, s), 9.37 (1H, s).

MS(EI) m/z: 278 (M)⁺

Example 6

4-[4-(1-Acetyl-1,2,3,6-tetrahydropyridin-4-yl)phenyl]isoquinoline-6-carboxamide

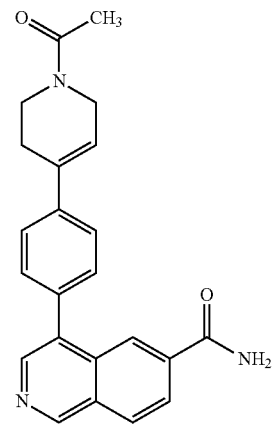

[Chemical formula 9]

(6a) 2-(Trimethylsilyl)ethyl 4-[4-(1-acetyl-4-hydroxypiperidin-4-yl)phenyl]isoquinoline-6-carboxylate Using 2-(trimethylsilyl)ethyl 4-{[(trifluoromethyl)sulfonyl]oxy}isoquinoline-6-carboxylate (800 mg, 1.90 mmol) and 1-acetyl-4-[4-(4,4,5,5-tetramethyl-1,3,2-dioxaborolan-2-yl)phenyl]piperidin-4-ol (983 mg, 2.85 mmol) synthesized in Reference Example 10, the desired title compound (931 mg, yield 100%) was obtained by the same method as in Reference Example 4 (4a).

¹H-NMR (CDCl₃) δ: 0.06 (9H, s), 1.11-1.15 (2H, m), 1.86-1.98 (2H, m), 1.92 (1H, s), 2.03-2.18 (2H, m), 2.18 (3H, s), 3.12-3.20 (1H, m), 3.63-3.72 (1H, m), 3.76-3.83 (1H, m), 4.43-4.48 (2H, m), 4.63-4.70 (1H, m), 7.53 (2H, d, J=8.4 Hz), 7.66 (2H, d, J=8.4 Hz), 8.10 (1H, d, J=8.6 Hz), 8.21 (1H, d, J=8.6 Hz), 8.49 (1H, s), 8.64 (1H, s), 9.32 (1H, s).

(6b) 4-[4-(1-Acetyl-4-hydroxypiperidin-4-yl)phenyl]isoquinoline-6-carboxamide

Using 2-(trimethylsilyl)ethyl 4-[4-(1-acetyl-4-hydroxypiperidin-4-yl)phenyl]isoquinoline-6-carboxylate (600 mg, 1.22 mmol) synthesized in Example 6 (6a), the desired title compound (331 mg, yield 69%) was obtained by the same method as in Reference Example 4 (4b).

$^1$H-NMR (DMSO-D$_6$) δ: 1.65-1.73 (2H, m), 1.77-1.86 (1H, m), 1.95-2.04 (1H, m), 2.02 (1H, s), 2.89-2.97 (1H, m), 3.41-3.48 (1H, m), 3.68-3.74 (1H, m), 4.30-4.36 (1H, m), 5.26 (1H, s), 7.52 (2H, d, J=8.4 Hz), 7.62 (1H, s), 7.67 (2H, d, J=8.4 Hz), 8.08 (1H, d, J=8.6 Hz), 8.22 (1H, br s), 8.26 (1H, d, J=8.6 Hz), 8.34 (1H, s), 8.47 (1H, s), 9.36 (1H, s).

MS(FAB) m/z: 390 (M+H)$^+$ (6c) 4-[4-(1-Acetyl-1,2,3,6-tetrahydropyridin-4-yl)phenyl]isoquinoline-6-carboxamide Trifluoroacetic acid (3.00 mL) was added to ethyl 4-[4-(1-acetyl-4-hydroxypiperidin-4-yl)phenyl]isoquinoline-6-carboxamide (209 mg, 0.537 mmol) produced in Example 6 (6b), followed by stirring at 50° C. for 24 hours.

After cooling, the resulting reaction liquid was concentrated under reduced pressure, and the residue thus obtained was purified by basic silica gel column chromatography (ethyl acetate:methanol, 100:0-95:5, V/V) to give the desired title compound (156 mg, yield 78%).

$^1$H-NMR (CDCl$_3$) δ: 2.07 (1.32H, s), 2.11 (1.68H, s), 2.53-2.58 (0.88H, m), 2.64-2.68 (1.12H, m), 3.66-3.70 (1.12H, m), 3.69-3.73 (0.88H, m), 4.13-4.16 (1.12H, m), 4.19-4.22 (0.88H, m), 6.32-6.36 (1H, m), 7.58 (2H, d, J=8.3 Hz), 7.63 (1H, br s), 7.66 (1.12H, d, J=8.3 Hz), 7.68 (0.88H, d, J=8.3 Hz), 8.13 (1H, d, J=8.7 Hz), 8.25 (1H, br s), 8.30 (1H, d, J=8.7 Hz), 8.38 (1H, s), 8.52 (1H, s), 9.41 (1H, s).

MS(FAB) m/z: 372 (M+H)$^+$

Example 7

4-(4-Chlorophenyl)isoquinoline-6-carboxamide hydrochloride

[Chemical formula 10]

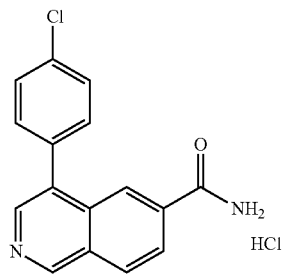

(7a) 4-(4-Chlorophenyl)isoquinoline-6-carboxamide

From 2-(trimethylsilyl)ethyl 4-{[(trifluoromethyl)sulfonyl]oxy}isoquinoline-6-carboxylate (6.00 g, 14.2 mmol) and 4-chlorophenylboronic acid (3.30 g, 30.0 mmol), 2-(trimethylsilyl)ethyl 4-(4-chlorophenyl)isoquinoline-6-carboxylate (3.90 g, yield 71%) was obtained by the same method as in Example 8 (8a). Further, using this compound (3.90 g, 9.9 mmol), the desired title compound (1.96 g, yield 70%) was obtained by the same method as in Example 4 (4b).

$^1$H-NMR (DMSO-D$_6$) δ: 7.62 (2H, d, J=8.5 Hz), 7.63 (1H, br s), 7.66 (2H, d, J=8.5 Hz), 8.13 (1H, d, J=8.6 Hz), 8.25 (1H, br s), 8.31 (1H, d, J=8.6 Hz), 8.31 (1H, s), 8.51 (1H, s), 9.43 (1H, s).

MS(EI) m/z 282 (M$^+$.)

(7b) 4-(4-Chlorophenyl)isoquinoline-6-carboxamide hydrochloride

Into methanol (250 ml), 4-(4-chlorophenyl)isoquinoline-6-carboxamide (1.9 g, 6.7 mmol) synthesized in Example 7 (7a) was dissolved, to which a 4M hydrochloric acid-dioxane solution (5 ml, 20 mmol) was added. After stirring at room temperature for 30 minutes, the resulting mixture was concentrated under reduced pressure. The resulting product was subjected to azeotropic distillation with diethyl ether, followed by recrystallization from methanol-diethyl ether to give the desired title compound (2 g, yield 93%).

$^1$H-NMR (DMSO-D$_6$) δ: 7.66 (2H, d, J=8.5 Hz), 7.70 (2H, d, J=8.5 Hz), 7.75 (1H, br s), 8.26 (1H, d, J=8.6 Hz), 8.37 (1H, s), 8.37 (1H, br s), 8.49 (1H, d, J=8.6 Hz), 8.63 (1H, s), 9.69 (1H, s).

MS(EI) m/z 282 (M$^+$.)

Example 8

4-{4-[formyl(methyl)amino]phenyl}isoquinoline-6-carboxamide

[Chemical formula 11]

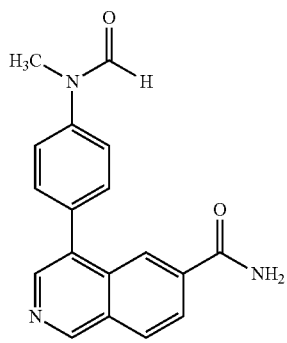

(8a) 2-(Trimethylsilyl)ethyl 4-{4-[(tert-butoxycarbonyl)(methyl)amino]phenyl}isoquinoline-6-carboxylate Into N,N-dimethylformamide (30 mL), 2-(trimethylsilyl)ethyl 4-{[(trifluoromethyl)sulfonyl]oxy}isoquinoline-6-carboxylate (1.50 g, 3.56 mmol), potassium carbonate (2.46 g, 17.8 mmol), tert-butyl methyl-[4-(4,4,5,5-tetramethyl-1,3,2-dioxaborolan-2-yl)phenyl]carbamate (1.78 g, 5.34 mmol), and a [1,1-bis(diphenylphosphino)ferrocene]dichloropalladium-dichloromethane complex (291 mg, 0.356 mmol) were dissolved, followed by stirring at 90° C. for one hour under a nitrogen atmosphere.

After cooling, the resulting reaction liquid was concentrated under reduced pressure and a solid was filtered off, followed by washing with dichloromethane. The resulting organic layer was concentrated under reduced pressure again. The residue thus obtained was purified by basic silica gel column chromatography (hexane:ethyl acetate, 100:0-80:20, V/V) and by neutral silica gel column chromatography (hexane:ethyl acetate, 100:0-50:50, V/V) to give the desired title compound (1.28 g, yield 75%).

$^1$H-NMR (CDCl$_3$) δ: 0.04 (9H, s), 1.09-1.13 (2H, m), 1.50 (9H, s), 3.35 (3H, s), 4.41-4.46 (2H, m), 7.42 (2H, d, J=8.6

Hz), 7.47 (2H, d, J=8.6 Hz), 8.08 (1H, d, J=8.5 Hz), 8.20 (1H, d, J=8.5 Hz), 8.54 (1H, s), 8.66 (1H, s), 9.29 (1H, s).

(8b) Tert-butyl [4-(6-carbamoylisoquinolin-4-yl) phenyl]methylcarbamate

Into tetrahydrofuran (10.0 mL), 2-(trimethylsilyl)ethyl 4-{4-[(tert-butoxycarbonyl)(methyl)amino] phenyl}isoquinoline-6-carboxylate (500 mg, 1.05 mmol) synthesized in Example 8 (8a) was dissolved, to which a tetra n-butylammonium fluoride/1.0 M tetrahydrofuran solution (1.36 mL, 1.36 mmol) was added under a nitrogen atmosphere. After stirring the resulting reaction liquid for one hour, a tetra n-butylammonium fluoride/1.0 M tetrahydrofuran solution (0.523 mL, 0.679 mmol) was further added, followed by stirring for one hour.

The resulting reaction liquid was concentrated under reduced pressure and dissolved in N,N-dimethylformamide (10.0 mL), to which triethylamine (1.75 mL, 12.5 mmol), 1-hydroxybenzotriazole monohydrate (42 mg, 0.314 mmol), ammonium chloride (559 mg, 10.5 mmol), and 1-ethyl-3-(3-dimethylaminopropyl)carbodiimide hydrochloride (1.00 g, 5.23 mmol) were added, followed by stirring at room temperature for four hours under a nitrogen atmosphere.

The reaction liquid was concentrated under reduced pressure, to which chloroform and water were added, followed by extraction with chloroform. The resulting organic layer was dried over sodium sulfate and filtered, and the filtrate was concentrated under reduced pressure. The residue thus obtained was purified by basic silica gel column chromatography (hexane:ethyl acetate, 60:40-0:100, V/V, ethyl acetate:methanol, 100:0-95:5, V/V) to give the desired title compound (202 mg, yield 51%).

$^1$H-NMR (DMSO-D$_6$) δ: 1.49 (9H, s), 3.36 (3H, s), 7.54 (2H, d, J=8.3 Hz), 7.59 (2H, d, J=8.3 Hz), 7.68 (1H, br s), 8.15 (1H, d, J=8.3 Hz), 8.29 (2H, br s), 8.33 (2H, d, J=8.3 Hz), 8.42 (1H, s), 8.54 (1H, s), 9.44 (1H, s).
MS(FAB) m/z: 378 (M+H)$^+$ (8c) 4-[4-(Methylamino)phenyl]isoquinoline-6-carboxamide Tert-butyl [4-(6-carbamoylisoquinolin-4-yl)phenyl]methylcarbamate (151 mg, 0.402 mmol) synthesized in Example 8 (8b) was suspended in dichloromethane (3.5 mL), to which trifluoroacetic acid (0.53 mL) was added at 0° C., followed by stirring at room temperature for three hours.

The resulting reaction liquid was cooled to 0° C., to which saturated aqueous sodium bicarbonate was added, followed by extraction with chloroform. The resulting organic layer was collected and concentrated under reduced pressure, and the residue thus obtained was purified by basic silica gel column chromatography (hexane:ethyl acetate, 50:50-0:100, V/V, ethyl acetate:methanol, 100:0-95:5, V/V) to give the desired title compound (102 mg, yield 92%).

$^1$H-NMR (DMSO-D$_6$) δ: 2.75 (3H, d, J=5.1 Hz), 5.97 (1H, q, J=5.1 Hz), 6.72 (2H, d, J=8.6 Hz), 7.30 (2H, d, J=8.6 Hz), 7.59 (1H, br s), 8.06 (1H, d, J=8.6 Hz), 8.21 (1H, br s), 8.22 (1H, d, J=8.6 Hz), 8.42 (1H, s), 8.45 (1H, s), 9.28 (1H, s).
MS(FAB) m/z: 278 (M+H)$^+$ (8d) 4-{4-[Formyl(methyl)amino] phenyl}isoquinoline-6-carboxamide Formic acid (0.5 mL) was added to 4-[4-(methylamino) phenyl]isoquinoline-6-carboxamide (30 mg, 0.108 mmol) synthesized in Example 8 (8c), to which anhydrous acetic acid (0.15 mL) was added at 0° C., followed by stirring at room temperature for four hours under a nitrogen atmosphere.

The resulting reaction liquid was concentrated under reduced pressure, and the residue thus obtained was purified by basic silica gel column chromatography (hexane:ethyl acetate, 50:50-0:100, V/V, ethyl acetate:methanol, 100:0-98:2, V/V) to give the desired title compound (36 mg, yield 100%).

$^1$H-NMR (DMSO-D$_6$) δ: 3.32 (3H, s), 7.58 (2H, d, J=8.0 Hz), 7.65 (1H, s), 7.65 (2H, d, J=8.0 Hz), 8.13 (1H, d, J=8.7 Hz), 8.27 (1H, br s), 8.31 (1H, d, J=8.7 Hz), 8.38 (1H, s), 8.52 (1H, s), 8.72 (1H, s), 9.42 (1H, s).
MS(FAB) m/z: 306 (M+H)$^+$

Example 9

8-{4-[2-(Tetrahydro-2H-pyran-4-yloxy)ethoxy]phenyl}-1,6-naphthyridine-2-carboxamide

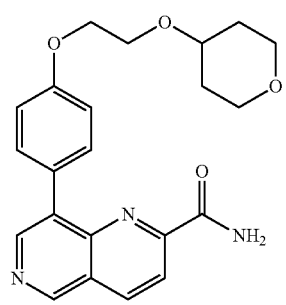

[Chemical formula 12]

(9a) Ethyl 8-{4-[2-(tetrahydro-2H-pyran-4-yloxy) ethoxy]phenyl}-1,6-naphthyridine-2-carboxylate Using 8-bromo-1,6-naphthyridine-2-carboxylic acid (447 mg, 1.77 mmol) and 4-{2-[4-(4,4,5,5-tetramethyl-1,3,2-dioxaborolan-2-yl)phenoxy]ethoxy}tetrahydro-2H-pyran (800 mg, 2.30 mmol) synthesized in Reference Example 2, the desired title compound (450 mg, yield 60%) was obtained by the same method as in Example 1 (1a).

$^1$H-NMR (CDCl$_3$) δ: 1.46 (3H, t, J=7.2 Hz), 1.61-1.72 (2H, m), 1.92-2.01 (2H, m), 3.44-3.50 (2H, m), 3.60-3.68 (1H, m), 3.89 (2H, t, J=5.0 Hz), 3.94-4.02 (2H, m), 4.23 (2H, t, J=5.0 Hz), 4.48 (2H, q, J=7.2 Hz), 7.10 (2H, d, J=8.8 Hz), 7.90 (2H, d, J=8.8 Hz), 8.28 (1H, d, J=8.3 Hz), 8.48 (1H, d, J=8.3 Hz), 8.92 (1H, s), 9.29 (1H, s).
MS(FAB) m/z: 423 (M+H)$^+$.

(9b) 8-{4-[2-(Tetrahydro-2H-pyran-4-yloxy)ethoxy] phenyl}-1,6-naphthyridine-2-carboxamide Using ethyl 8-{4-[2-(tetrahydro-2H-pyran-4-yloxy) ethoxy]phenyl}-1,6-naphthyridine-2-carboxylate (340 mg, 0.81 mmol) synthesized in Example 9 (9a), the desired title compound (318 mg, yield 99%) was obtained by the same method as in Example 1 (1b).

$^1$H-NMR (DMSO-D$_6$) δ: 1.36-1.48 (2H, m), 1.83-1.92 (2H, m), 3.27-3.39 (2H, m), 3.54-3.63 (1H, m), 3.77-3.85 (4H, m), 4.16-4.21 (2H, m), 7.13 (2H, d, J=8.8 Hz), 7.59 (1H, br s), 7.78 (2H, d, J=8.8 Hz), 8.00 (1H, br s), 8.29 (1H, d, J=8.5 Hz), 8.82 (1H, d, J=8.5 Hz), 8.84 (1H, s), 9.45 (1H, s).
MS(FAB) m/z: 394 (M+H)$^+$.

Example 10

N-methyl-8-{4-[2-(tetrahydro-2H-pyran-4-yloxy)ethoxy]phenyl}-1,6-naphthyridine-2-carboxamide

[Chemical formula 13]

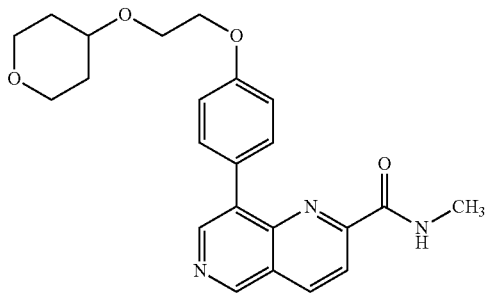

N-methyl-8-{4-[2-(tetrahydro-2H-pyran-4-yloxy)ethoxy]phenyl}-1,6-naphthyridine-2-carboxylic acid (281 mg, 0.71 mmol), an intermediate product of the synthetic process in Example 9 (9a), was dissolved in N,N-dimethylformamide (7 mL), to which methylamine hydrochloride (478 mg, 7.13 mol), triethylamine (1.2 mL, 8.56 mmol), 1-hydroxybenzotriazole (33 mg, 0.21 mmol), and 1-ethyl-3-(3-dimethylaminopropyl)carbodiimide hydrochloride (681 mg, 3.56 mmol) were added, followed by stirring at room temperature for 48 hours. The resulting reaction liquid was filtered and concentrated under reduced pressure. The residue thus obtained was purified by silica gel column chromatography (hexane:ethyl acetate, 40:60-0:100, V/V) to give the desired title compound (30 mg, yield 10%).

$^1$H-NMR (DMSO-D$_6$) δ: 1.39-1.49 (2H, m), 1.85-1.95 (2H, m), 2.90 (3H, d, J=4.9 Hz), 3.32-3.40 (2H, m), 3.56-3.65 (1H, m), 3.79-3.86 (4H, m), 4.18-4.23 (2H, m), 7.14 (2H, d, J=8.5 Hz), 7.80 (2H, d, J=8.5 Hz), 8.14 (1H, br s), 8.29 (1H, d, J=8.5 Hz), 8.82 (1H, d, J=8.5 Hz), 8.84 (1H, s), 9.45 (1H, s).

MS (FAB) m/z: 408 (M+H)$^+$.

Example 11

N-ethyl-8-{4-[2-(tetrahydro-2H-pyran-4-yloxy)ethoxy]phenyl}-1,6-naphthyridine-2-carboxamide

[Chemical formula 14]

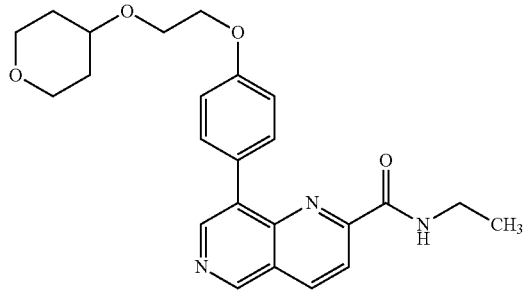

Using N-methyl-8-{4-[2-(tetrahydro-2H-pyran-4-yloxy)ethoxy]phenyl}-1,6-naphthyridine-2-carboxylic acid (300 mg, 0.76 mmol) produced in the synthetic process in Example 9 (9a) and ethylamine hydrochloride (616 mg, 7.61 mmol), the desired title compound (100 mg, yield 31%) was obtained by the same method as in Example 10.

$^1$H-NMR (DMSO-D$_6$) δ: 1.16 (3H, t, J=7.2 Hz), 1.38-1.56 (2H, m), 1.84-1.98 (2H, m), 3.33-3.47 (4H, m), 3.56-3.66 (1H, m), 3.79-3.91 (4H, m), 4.20 (2H, t, J=4.8 Hz), 7.15 (2H, d, J=8.8 Hz), 7.82 (2H, d, J=8.8 Hz), 8.08-8.18 (1H, m), 8.28 (1H, d, J=8.3 Hz), 8.83 (1H, d, J=8.3 Hz), 8.86 (1H, s), 9.46 (1H, s).

MS (FAB) m/z: 422 (M+H)$^+$.

Example 12

4-(6-Carbamoylisoquinolin-4-yl)phenyl dimethylcarbamate

[Chemical formula 15]

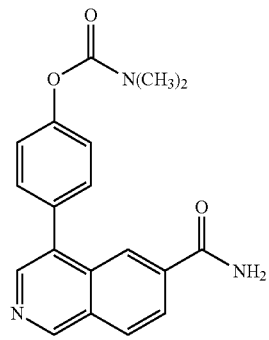

(12a) 2-(Trimethylsilyl)ethyl 4-{4-[(dimethylcarbamoyl)oxy]phenyl}isoquinoline-6-carboxylate Into dichloromethane (6.5 mL), 2-(trimethylsilyl)ethyl 4-(4-hydroxyphenyl)isoquinoline-6-carboxylate (234 mg, 0.64 mmol) synthesized from 2-(trimethylsilyl)ethyl 4-{[(trifluoromethyl)sulfonyl]oxy}isoquinoline-6-carboxylate by the same method as in Example 8 (8a) was dissolved, to which triethylamine (178 μL, 1.28 mmol), 4-dimethylaminopyridine (23 mg, 0.19 mmol) and N,N-dimethylcarbamoyl chloride (88 μL, 0.96 mmol) were added, followed by stirring at room temperature for three hours. The resulting reaction liquid was concentrated under reduced pressure and the residue thus obtained was purified by silica gel column chromatography (hexane:ethyl acetate, 100:0-50:50, V/V) to give the desired title compound (260 mg, yield 93%).

$^1$H-NMR (CDCl$_3$) δ: 0.07 (9H, s), 1.09-1.18 (2H, m), 3.07 (3H, s), 3.17 (3H, s), 4.42-4.51 (2H, m), 7.32 (2H, d, J=6.5 Hz), 7.52 (2H, d, J=6.5 Hz), 8.10 (1H, d, J=8.5 Hz), 8.22 (1H, d, J=8.5 Hz), 8.56 (1H, s), 8.65 (1H, s), 9.31 (1H, s).

MS(FAB) m/z: 437 (M+H)$^+$.

(12b) 4-(6-Carbamoylisoquinolin-4-yl)phenyl dimethylcarbamate

Using 2-(trimethylsilyl)ethyl 4-{4-[(dimethylcarbamoyl)oxy]phenyl}isoquinoline-6-carboxylate (255 mg, 0.59 mmol) produced in Example 12 (12a), the desired title compound (149 mg, yield 76%) was obtained by the same method as in Example 4 (4b).

¹H-NMR (DMSO-D₆) δ: 2.95 (3H, s), 3.09 (3H, s), 7.33 (2H, d, J=8.0 Hz), 7.58 (2H, d, J=8.0 Hz), 7.62 (1H, br s), 8.11 (1H, d, J=8.8 Hz), 8.24 (1H, br s), 8.29 (1H, d, J=8.8 Hz), 8.35 (1H, s), 8.50 (1H, s), 9.40 (1H, s).
MS (FAB) m/z: 336 (M+H)⁺.

Example 13

4-{4-[(1E)-3-(dimethylamino)-3-oxopropen-1-yl]phenyl}isoquinoline-6-carboxamide

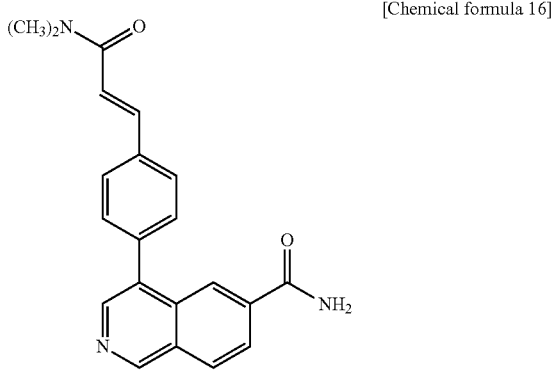

[Chemical formula 16]

(13a) 2-(Trimethylsilyl)ethyl 4-(4-formylphenyl)isoquinoline-6-carboxylate

Using 2-(trimethylsilyl)ethyl 4-{[(trifluoromethyl)sulfonyl]oxy}isoquinoline-6-carboxylate (600 mg, 1.42 mmol) and 4-formylphenylboric acid (320 mg, 2.14 mmol), the desired title compound (427 mg, yield 79%) was obtained by the same method as in Example 8 (8a).
¹H-NMR (CDCl₃) δ: 0.06 (9H, s), 1.08-1.15 (2H, m), 4.43-4.50 (2H, m), 7.72 (2H, d, J=7.8 Hz), 8.09 (2H, d, J=7.8 Hz), 8.14 (1H, d, J=8.5 Hz), 8.25 (1H, d, J=8.5 Hz), 8.57 (1H, s), 8.59 (1H, s), 9.37 (1H, s), 10.16 (1H, s).
MS (FAB) m/z: 378 (M+H)¹.

(13b) 2-(Trimethylsilyl)ethyl 4-{4-[(1E)-3-(dimethylamino)-3-oxopropen-1-yl]phenyl}isoquinoline-6-carboxylate Diethyl[2-(dimethylamino)-2-oxoethyl]phosphonate (133 mg, 0.597 mmol) was dissolved in dichloromethane (4 mL), to which 55% sodium hydride (21 mg, 0.48 mmol) was added at 0° C., followed by stirring for 10 minutes. To this solution, 2-(trimethylsilyl)ethyl 4-(4-formylphenyl)isoquinoline-6-carboxylate (150 mg, 0.40 mmol) synthesized in Example 13 (13a) was added, followed by stirring for one hour. To the resulting reaction liquid, a saturated aqueous solution of ammonium chloride was added, followed by extraction with ethyl acetate. The resulting organic layer was washed with saturated brine and dried over anhydrous sodium sulfate. The solvent was distilled off under reduced pressure. The residue thus obtained was purified by silica gel column chromatography (hexane:ethyl acetate, 100:0-35:65, V/V) to give the desired title compound (168 mg, yield 95%).
¹H-NMR (CDCl₃) δ: 0.05 (9H, s), 1.09-1.16 (2H, m), 3.11 (3H, s), 3.23 (3H, s), 4.40-4.52 (2H, m), 7.01 (1H, d, J=15.4 Hz), 7.55 (2H, d, J=8.3 Hz), 7.72 (2H, d, J=8.3 Hz), 7.78 (1H, d, J=15.4 Hz), 8.11 (1H, d, J=8.5 Hz), 8.22 (1H, d, J=8.5 Hz), 8.58 (1H, s), 8.64 (1H, s), 9.33 (1H, s).
MS (FAB) m/z: 447 (M+H)⁺.

(13c) 4-{4-[(1E)-3-(Dimethylamino)-3-oxopropen-1-yl]phenyl}isoquinoline-6-carboxamide Using 2-(trimethylsilyl)ethyl 4-{4-[(1E)-3-(dimethylamino)-3-oxopropen-1-yl]phenyl}isoquinoline-6-carboxylate (165 mg, 0.37 mmol) produced in Example 13 (13b), the desired title compound (104 mg, yield 81%) was obtained by the same method as in Example 4 (4b).
¹H-NMR (DMSO-D₆) δ: 2.95 (3H, s), 3.19 (3H, s), 7.33 (1H, d, J=15.4 Hz), 7.58 (1H, d, J=15.4 Hz), 7.62 (3H, d, J=8.1 Hz), 7.92 (2H, d, J=8.1 Hz), 8.12 (1H, d, J=8.5 Hz), 8.24 (1H, br s), 8.30 (1H, d, J=8.5 Hz), 8.37 (1H, s), 8.53 (1H, s), 9.41 (1H, s).
MS (FAB) m/z: 346 (M+H)⁺.

Example 14

4-{4-[(1E)-3-(morpholin-4-yl-3-oxopropen-1-yl]phenyl}isoquinoline-6-carboxamide

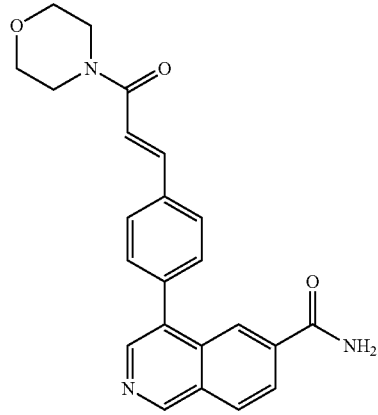

[Chemical formula 17]

(14a) 2-(Trimethylsilyl)ethyl 4-{4[(1E)-3-morpholin-4-yl-3-oxopropen-1-yl]phenyl}isoquinoline-6-carboxylate Using 2-(trimethylsilyl)ethyl 4-(4-formylphenyl)isoquinoline-6-carboxylate (123 mg, 0.33 mmol) produced in Example 13 (13a) and diethyl [2-(morpholin-4-yl-2-oxoethyl)phosphonate (130 mg, 0.49 mmol), the desired title compound (155 mg, yield 99%) was obtained by the same method as in Example 13 (13b).
¹H-NMR (CDCl₃) δ: 0.06 (9H, s), 1.12 (2H, t, J=8.2 Hz), 3.66-3.85 (8H, m), 4.46 (2H, t, J=8.4 Hz), 6.96 (1H, d, J=15.4 Hz), 7.55 (2H, d, J=8.0 Hz), 7.71 (2H, d, J=8.0 Hz), 7.81 (1H, d, J=15.4 Hz), 8.11 (1H, d, J=8.5 Hz), 8.23 (1H, d, J=8.5 Hz), 8.57 (1H, s), 8.63 (1H, s), 9.33 (1H, s).
MS (FAB) m/z: 489 (M+H)⁺.

(14b) 4-{4-[(1E)-3-(Morpholin-4-yl-3-oxopropen-1-yl]phenyl}isoquinoline-6-carboxamide Using 2-(trimethylsilyl)ethyl 4-{4[(1E)-3-morpholin-4-yl-3-oxopropen-1-yl]phenyl}isoquinoline-6-carboxylate (155 mg, 0.32 mmol) produced in Example 14 (14a), the desired title compound (94 mg, yield 76%) was obtained by the same method as in Example 4 (4b).

¹H-NMR (DMSO-D₆) δ: 3.30-3.46 (2H, m), 3.55-3.68 (4H, m), 3.70-3.84 (2H, m), 7.37 (1H, d, J=15.1 Hz), 7.57-7.69 (4H, m), 7.93 (2H, d, J=7.3 Hz), 8.12 (1H, d, J=8.5 Hz), 8.23 (1H, br s), 8.29 (1H, d, J=8.5 Hz), 8.36 (1H, s), 8.53 (1H, s), 9.41 (1H, s).

MS (FAB) m/z: 388 (M+H)⁺.

Example 15

4-[4-(3-Morpholin-4-yl-3-oxopropyl)phenyl]isoquinoline-6-carboxamide

[Chemical formula 18]

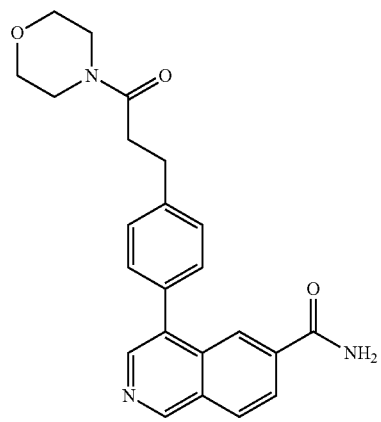

(15a) 2-(Trimethylsilyl)ethyl 4-[4-(3-morpholin-4-yl-3-oxopropyl)phenyl]isoquinoline-6-carboxylate Using 2-(trimethylsilyl)ethyl 4-{[(trifluoromethyl)sulfonyl]oxy}isoquinoline-6-carboxylate (300 mg, 0.71 mmol) and 4-(2-carboxyethyl)phenylboronic acid (207 mg, 1.07 mmol), a carboxylic acid intermediate was obtained by the same method as in Example 8 (8a), and the desired title compound (199 mg, yield 57%) was obtained by the same method as in Example 10 without isolating this intermediate.

¹H-NMR (CDCl₃) δ: 0.07 (9H, s), 1.10-1.16 (2H, m), 2.71-2.74 (2H, m), 3.11 (2H, t, J=7.9 Hz), 3.47 (2H, t, J=4.8 Hz), 3.62 (2H, t, J=4.8 Hz), 3.66-3.69 (4H, m), 4.44-4.48 (2H, m), 7.40 (2H, d, J=8.3 Hz), 7.43-7.48 (2H, m), 8.09 (1H, d, J=8.1 Hz), 8.20 (1H, dd, J=8.1, 1.5 Hz), 8.54 (1H, s), 8.66 (1H, s), 9.31 (1H, s).

MS (FAB) m/z: 491 (M+H)⁺.

(15b) 4-[4-(3-Morpholin-4-yl-3-oxopropyl)phenyl]isoquinoline-6-carboxamide

Using 2-(trimethylsilyl)ethyl 4-[4-(3-morpholin-4-yl-3-oxopropyl)phenyl]isoquinoline-6-carboxylate (195 mg, 0.39 mmol) produced in Example 15 (15a), the desired title compound (50 mg, yield 33%) was obtained by the same method as in Example 4 (4b).

¹H-NMR (DMSO-D₆) δ: 2.74 (2H, t, J=7.7 Hz), 2.95 (2H, t, J=7.7 Hz), 3.43-3.49 (4H, m), 3.49-3.59 (4H, m), 7.47 (2H, d, J=8.3 Hz), 7.50 (2H, d, J=8.3 Hz), 7.61 (1H, br s), 8.10 (1H, d, J=8.5 Hz), 8.22 (1H, br s), 8.28 (1H, d, J=8.5 Hz), 8.36 (1H, s), 8.46 (1H, s), 9.38 (1H, s).

MS (FAB) m/z: 438 (M+H)⁺.

Example 16

4-{4-[4-Acetylpiperazin-1-yl)phenyl]isoquinoline-6-carboxamide

[Chemical formula 19]

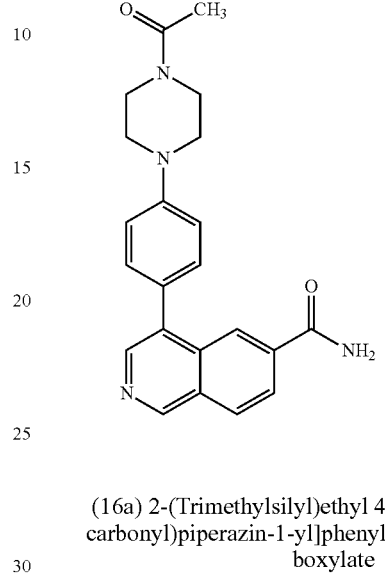

(16a) 2-(Trimethylsilyl)ethyl 4-{4-[4-(tert-butoxycarbonyl)piperazin-1-yl]phenyl}isoquinoline-6-carboxylate Using 2-(trimethylsilyl)ethyl 4-{[(trifluoromethyl)sulfonyl]oxy}isoquinoline-6-carboxylate (1.00 g, 2.38 mmol) and tert-butyl-4-[4-(4,4,5,5-tetramethyl-1,3,2-dioxaborolan-2-yl)phenyl]piperazine-1-carboxylate (998 mg, 2.57 mmol), the desired title compound (1.01 g, yield 79%) was obtained by the same method as in Example 4 (4a).

¹H-NMR (CDCl₃) δ: 0.05 (9H, s), 1.12 (2H, t, J=8.4 Hz), 1.49 (9H, s), 3.20-3.29 (4H, m), 3.59-3.66 (4H, m), 4.44 (2H, t, J=8.4 Hz), 7.08 (2H, d, J=8.2 Hz), 7.25 (1H, s), 7.43 (2H, d, J=8.2 Hz), 8.06 (1H, d, J=8.6 Hz), 8.18 (1H, d, J=8.6 Hz), 8.53 (1H, s), 8.69 (1H, s), 9.26 (1H, s).

(16b) 2-(Trimethylsilyl)ethyl 4-[4-(4-acetylpiperazin-1-yl)phenyl]isoquinoline-6-carboxylate Into dichloromethane (5 mL), 2-(trimethylsilyl)ethyl 4-{4-[4-(tert-butoxycarbonyl)piperazin-1-yl]phenyl}isoquinoline-6-carboxylate (103 mg, 0.193 mmol) synthesized in Example 16 (16a) was dissolved, to which trifluoroacetic acid (0.5 mL) was added, followed by stirring at room temperature for three hours. After concentration, the resulting mixture was diluted with dichloromethane (20 mL) and neutralized with a saturated aqueous solution of sodium bicarbonate (15 mL). The resulting organic layer was dried over sodium sulfate and filtered. The solvent was distilled off under reduced pressure. The residue thus obtained was dissolved in pyridine (5 mL), to which anhydrous acetic acid (0.5 mL) was added, followed by stirring at room temperature overnight. After concentration, the resulting mixture was diluted with dichloromethane (20 mL) and neutralized with a saturated aqueous solution of sodium bicarbonate (15 mL). The solution thus obtained was extracted with dichloromethane (20 mL), and the resulting organic layer was dried over sodium sulfate and filtered. The solvent was distilled off under reduced pressure and the resulting product was purified by thin layer chromatography (dichloromethane:methanol=97:3) to give the desired title compound (54 mg, yield 58%).

$^1$H-NMR (CDCl$_3$) δ: 0.10 (9H, s), 1.17 (2H, t, J=8.3 Hz), 2.21 (3H, s), 3.30-3.38 (4H, m), 3.70-3.74 (2H, m), 3.86-3.89 (2H, m), 4.49 (2H, t, J=8.3 Hz), 7.12 (2H, d, J=8.8 Hz), 7.49 (2H, d, J=8.8 Hz), 8.11 (1H, d, J=8.8 Hz), 8.22 (1H, d, J=8.8 Hz), 8.58 (1H, s), 8.74 (1H, s), 9.31 (1H, s).

(16c) 4-[4-(4-acetylpiperazin-1-yl)phenyl]isoquinoline-6-carboxamide

Using 2-(trimethylsilyl)ethyl 4-[4-(4-acetylpiperazin-1-yl)phenyl]isoquinoline-6-carboxylate (54 mg, 0.11 mmol) synthesized in Example 16 (16b), the desired title compound (38 mg, yield 90%) was obtained by the same method as in Example 4 (4b).

$^1$H-NMR (CDCl$_3$, 400MHz) δ: 2.16 (3H, s), 3.23-3.34 (4H, m), 3.64-3.70 (2H, m), 3.78-3.85 (2H, m), 5.70 (1H, br s), 6.12 (1H, br s), 7.09 (2H, d, J=8.6 Hz), 7.45 (2H, d, J=8.6 Hz), 8.03 (1H, d, J=8.6 Hz), 8.10 (1H, d, J=8.6 Hz), 8.39 (1H, s), 8.53 (1H, s), 9.26 (1H, s).

Reference Example 1

2-[3-Fluoro-4-(methoxymethoxy)phenyl]-4,4,5,5-tetramethyl-1,3,2-dioxaborolane

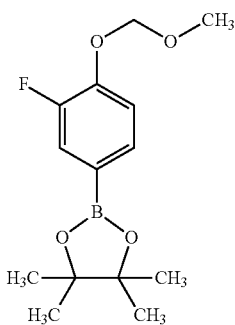

[Chemical formula 20]

(1a) 4-Bromo-2-fluoro-1-(methoxymethoxy)benzene

Into acetone (300 ml), 4-bromo-2-fluorophenol (30 g, 157 mmol) was dissolved, to which chloromethyl methyl ether (18 ml, 237 mmol) and potassium carbonate (43 g, 235 mmol) were added, followed by stirring at room temperature for two hours. Impurities were filtered off and the filtered solution was washed with acetone. The filtrate was concentrated under reduced pressure and the residue thus obtained was purified by silica gel column chromatography (hexane:ethyl acetate, 100:0-85:15, V/V) to give the desired title compound (36.5 g, yield 82%).

$^1$H-NMR (CDCl$_3$) δ: 3.51 (3H, s), 5.19 (2H, s), 7.05-7.10 (1H, m), 7.16-7.20 (1H, m), 7.22-7.28 (1H, m).

(1b) 2-[3-Fluoro-4-(methoxymethoxy)phenyl]-4,4,5,5-tetramethyl-1,3,2-dioxaborolane Into dimethyl sulfoxide (200 ml), 4-bromo-2-fluoro-1-(methoxymethoxy)benzene (20 g, 85 mmol) synthesized in Example (8a) was dissolved, to which bis(pinacolato)diboron (28 g, 110 mmol), a [1,1'-bis(diphenylphosphino)-ferrocene] dichloropalladium-dichloromethane complex (7.0 g, 8.5 mmol), and potassium acetate (25 g, 255 mmol) were added, followed by stirring at 80° C. for one hour. The mixture was brought down to room temperature, to which water and ethyl acetate were added, and impurities were removed using Celite. The filtered solution was washed with ethyl acetate. The filtrate was separated and the organic layer was sequentially washed with water and saturated brine, and dried over anhydrous sodium sulfate. The solvent was distilled off under reduced pressure. The residue thus obtained was purified by silica gel column chromatography (hexane:ethyl acetate, 100:0-80:20, V/V) to give the desired title compound (15.8 g, yield 66%).

$^1$H-NMR (CDCl$_3$) δ: 1.33 (12H, s), 3.51 (3H, s), 5.24 (2H, s), 7.15-7.20 (1H, m), 7.49-7.50 (1H, m), 7.51-7.53 (1H, m).

Reference Example 2

4-{2-[4-(4,4,5,5-Tetramethyl-1,3,2-dioxaborolan-2-yl)phenoxy]ethoxy)tetrahydro-2H-pyran

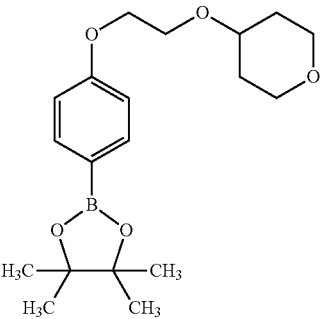

[Chemical formula 21]

(2a) 2-{2-[4-(4,4,5,5-Tetramethyl-1,3,2-dioxaborolan-2-yl)phenoxy]ethoxy}tetrahydro-2H-pyran Into dimethylformamide (250 mL), 4-(4,4,5,5-tetramethyl-1,3,2-dioxaborolan-2-yl)phenol (10.0 g, 45.5 mmol) and 2-(2-bromoethoxy)tetrahydro-2H-pyran (10.0 g, 45.5 mmol) were dissolved, to which 60% sodium hydride in oil (2.98 g, 68.3 mmol) was added while cooling with ice, followed by stirring for three hours while cooling with ice, and further for 17 hours at room temperature. Ethyl acetate was then added, and excess hydrated sodium was neutralized with 1M hydrochloric acid. Further, water was added and the resulting solution was separated. The resulting organic layer was washed with saturated brine, and dried over anhydrous sodium sulfate. The solvent was distilled off under reduced pressure. The residue thus obtained was purified by silica gel column chromatography (hexane:ethyl acetate, 100:0-70:30, V/V) to give the desired title compound (13.3 g, yield 84%).

$^1$H-NMR (CDCl$_3$) δ: 1.33 (12H, s), 1.47-1.68 (2H, m), 1.69-1.79 (2H, m), 1.79-1.91 (2H, m), 3.48-3.57 (1H, m), 3.79-3.85 (1H, m), 3.87-3.93 (1H, m), 4.01-4.10 (1H, m), 4.15-4.22 (2H, m), 4.71 (1H, t, J=3.5 Hz), 6.92 (2H, dt, J=9.0, 2.1 Hz), 7.74 (2H, dt, J=8.8, 2.1 Hz).

(2b) 2-[4-(4,4,5,5-Tetramethyl-1,3,2-dioxaborolan-2-yl)phenoxy]ethanol

Using 2-{2-[4-(4,4,5,5-tetramethyl-1,3,2-dioxaborolan-2-yl)phenoxy]ethoxy}tetrahydro-2H-pyran (13.0 g, 37.3 mmol) synthesized in Reference Example 2 (2a), the desired title compound (9.45 g, yield 96%) was obtained by the same method as in Example 2 (2c).

$^1$H-NMR (CDCl$_3$) δ: 1.33 (12H, s), 3.97 (2H, t, J=4.5 Hz), 4.11 (2H, t, J=4.5 Hz), 6.91 (2H, dt, J=8.8, 2.1 Hz), 7.75 (2H, dt, J=8.8, 2.1 Hz).

(2c) 2-[4-(4,4,5,5-Tetramethyl-1,3,2-dioxaborolan-2-yl)phenoxy]ethyl benzenesulfonate Into dichloromethane 100 ml, 2-[4-(4,4,5,5-tetramethyl-1,3,2-dioxaborolan-2-yl)phenoxy]ethanol (4.4 g, 16.7 mmol) synthesized in Example 2 (2b) was dissolved, to which triethylamine (4.6 ml, 33.2 mmol), 4-dimethylaminopyridine (400 mg, 3.3 mmol), tosyl chloride (4.8 g, 25.2 mmol) were sequentially added while cooling with ice. The resulting mixture was warmed back to room temperature, followed by further stirring for two hours. The resulting reaction liquid was sequentially washed with water and saturated brine, and dried over anhydrous sodium sulfate. The solvent was distilled off under reduced pressure. The residue thus obtained was purified by silica gel column chromatography (hexane:ethyl acetate, 100:0-70:30, V/V) to give the desired title compound (6.1 g, yield 88%).

$^1$H-NMR (CDCl$_3$) δ: 1.33 (12H, s), 2.44 (3H, s), 4.16 (2H, t, J=4.7 Hz), 4.37 (2H, t, J=4.7 Hz), 6.75 (2H, d, J=8.4 Hz), 7.33 (2H, d, J=8.4 Hz), 7.70 (2H, d, J=8.4 Hz), 7.81 (2H, d, J=8.4 Hz).

(2d) 4-{2-[4-(4,4,5,5-Tetramethyl-1,3,2-dioxaborolan-2-yl)phenoxy]ethoxy}tetrahydro-2H-pyran Using tetrahydropyran-4-ol (3.7 g, 36.2 mmol) and 2-[4-(4,4,5,5-tetramethyl-1,3,2-dioxaborolan-2-yl)phenoxy]ethyl benzenesulfonate (6 g, 14.3 mmol) synthesized in Reference Example 2 (2c), the desired title compound (3.4 g, yield 68%) was obtained by the same method as in Reference Example 2 (2a).

$^1$H-NMR (CDCl$_3$) δ: 1.33 (12H, s), 1.57-1.68 (2H, m), 1.88-1.97 (2H, m), 3.40-3.48 (2H, m), 3.55-3.63 (1H, m), 3.83 (2H, t, J=5.0 Hz), 3.92-3.99 (2H, m), 4.15 (2H, t, J=5.0 Hz), 6.91 (2H, d, J=8.7 Hz), 7.74 (2H, d, J=8.7 Hz).

Reference Example 3

Diethyl{[4-(4,4,5,5-tetramethyl-1,3,2-dioxaborolan-2-yl)phenoxy]methyl}phosphonate

[Chemical formula 22]

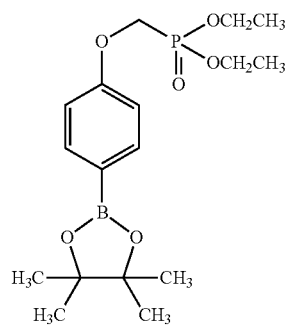

(3a) (Diethoxyphosphoryl)methyl 4-methylbenzenesulfonate

Paraformaldehyde (137 mg) was dissolved in toluene (79.5 μL), to which triethylamine (52 μL, 0.369 mmol) and diethylphosphite (466 μL, 3.62 mmol) were added. The resulting solution was stirred at approximately 90° C. for four hours, and then at 125° C. for one hour under a nitrogen atmosphere. The solution was cooled to 0° C., to which triethylamine (707 μL, 5.07 mmol) and p-toluenesulfonyl chloride (625 mg, 3.28 mmol) were slowly added. The resulting reaction liquid was stirred at room temperature overnight and then impurities were filtered off.

The organic layer thus obtained was washed with water and saturated brine, and dried over sodium sulfate, and then filtered. The solvent was distilled off under reduced pressure to give the desired title compound (551 mg, yield 47%).

$^1$H-NMR (CDCl$_3$) δ: 1.32 (6H, t, J=7.1 Hz), 2.46 (3H, s), 4.11-4.19 (4H, m), 4.18 (2H, d, J=10.1 Hz), 7.37 (2H, d, J=8.5 Hz), 7.81 (2H, d, J=8.5 Hz).

(3b) Diethyl{[4-(4,4,5,5-tetramethyl-1,3,2-dioxaborolan-2-yl)phenoxy]methyl}phosphonate Using 4-(4,4,5,5-tetramethyl-1,3,2-dioxaborolan-2-yl)phenol (313 mg, 1.42 mmol) and (diethoxyphosphoryl)methyl 4-methylbenzenesulfonate (550 mg, 1.71 mmol), the desired title compound (121 mg, yield 23%) was obtained by the same method as in Reference Example 2 (2a).

$^1$H-NMR (CDCl$_3$) δ: 1.33 (12H, s), 1.36 (6H, t, J=7.1 Hz), 4.20-4.27 (4H, m), 4.30 (2H, d, J=10.5 Hz), 6.95 (2H, d, J=8.3 Hz), 7.76 (2H, d, J=8.3 Hz).

Reference Example 4

1-[4-(4,4,5,5-Tetramethyl-1,3,2-dioxaborolan-2-yl)phenoxy]propan-2-ol

[Chemical formula 23]

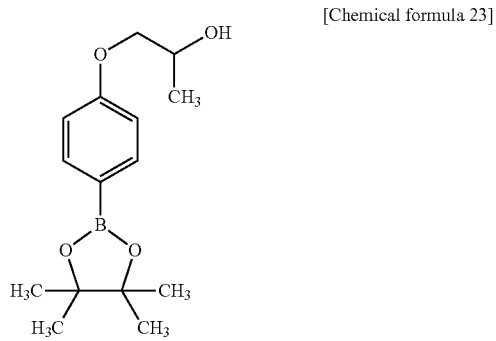 [SMILES: CC(O)COc1ccc(B2OC(C)(C)C(C)(C)O2)cc1]

(4a) 1-[4-(4,4,5,5-Tetramethyl-1,3,2-dioxaborolan-2-yl)phenoxy]acetone 4-(4,4,5,5-Tetramethyl-1,3,2-dioxaborolan-2-yl)phenol (770 mg, 3.50 mmol) and potassium carbonate (725 mg, 5.25 mmol) were dissolved in acetone (8.0 mL), to which chloroacetone (0.344 mL, 4.20 mmol) was added, followed by stirring at 65° C. overnight under a nitrogen atmosphere.

The resulting reaction liquid was cooled to room temperature and then concentrated under reduced pressure. To the residue thus obtained, dichloromethane and water were added, followed by extraction with dichloromethane. The organic layer thus obtained was dried over sodium sulfate.

After filtration, the organic layer was concentrated under reduced pressure and then purified by silica gel column chromatography (hexane:ethyl acetate, 100:0-70:30, V/V) to give the desired title compound (530 mg, yield 55%).

¹H-NMR (CDCl₃) δ: 1.33 (12H, s), 2.28 (3H, s), 4.56 (2H, s), 6.88 (2H, d, J=8.7 Hz), 7.76 (2H, d, J=8.7 Hz).

MS(ESI) m/z: 277 (M+H)⁺

(4b) 1-[4-(4,4,5,5-Tetramethyl-1,3,2-dioxaborolan-2-yl)phenoxy]propan-2-ol

Into ethanol (5.3 mL), 1-[4-(4,4,5,5-tetramethyl-1,3,2-dioxaborolan-2-yl)phenoxy]acetone (530 mg, 1.92 mmol) synthesized in Reference Example 4 (4a) was dissolved, to which sodium borohydride (94 mg, 2.50 mmol) was added at 0° C., followed by stirring at room temperature for 30 minutes. To this reaction liquid, water was added, followed by extraction with dichloromethane. The resulting organic layer was dried over sodium sulfate and filtered, and then concentrated under reduced pressure. The residue thus obtained was purified by silica gel column chromatography (hexane:ethyl acetate, 100:0-70:30, V/V) to give the desired title compound (483 mg, yield 91%).

¹H-NMR (CDCl₃) δ: 1.29 (3H, d, J=6.4 Hz), 1.33 (12H, s), 2.33 (1H, d, J=3.7 Hz), 3.82 (1H, dd, J=9.2, 7.8 Hz), 3.97 (1H, dd, J=9.2, 3.2 Hz), 4.16-4.25 (1H, m), 6.90 (2H, d, J=8.7 Hz), 7.75 (2H, d, J=8.7 Hz).

Reference Example 5

3-(Tetrahydro-2H-pyran-4-yloxy)propan-1-ol

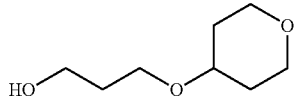

[Chemical formula 24]

(5a) 4-[3-(Benzyloxy)propoxy]tetrahydro-2H-pyran

Using tetrahydro-4-pyranol (0.693 mL, 7.27 mmol) and [(3-bromopropoxy)methyl]benzene (1.93 mL, 10.9 mmol), the desired title compound (437 mg, yield 24%) was obtained by the same method as in Reference Example 2 (2a).

¹H-NMR (CDCl₃) δ: 1.51-1.60 (2H, m), 1.85-1.91 (4H, m), 3.39-3.47 (3H, m), 3.55-3.60 (4H, m), 3.90-3.95 (2H, m), 4.51 (2H, s), 7.26-7.37 (5H, m).

MS(ESI) m/z: 251 (M+H)⁺

(5b) 3-(Tetrahydro-2H-pyran-4-yloxy)propan-1-ol

Into ethanol (1.7 mL), 4-[3-(benzyloxy)propoxy]tetrahydro-2H-pyran (436 mg, 1.74 mmol) synthesized in Reference Example 5 (5a) was dissolved, and under a nitrogen atmosphere, 10% palladium hydroxide-carbon (44 mg) was added. Hydrogen substitution was performed, followed by stirring at 45° C. for one hour.

After cooling, the resulting reaction liquid was filtered through Celite, and the organic layer thus obtained was concentrated under reduced pressure to give the desired title compound (279 mg, yield 100%).

¹H-NMR (CDCl₃) δ: 1.54-1.63 (2H, m), 1.82-1.94 (4H, m), 2.43 (1H, t, J=5.5 Hz), 3.42-3.54 (3H, m), 3.67 (2H, t, J=5.5 Hz), 3.79 (2H, q, J=5.5 Hz), 3.90-3.96 (2H, m).

Reference Example 6

3-(Tetrahydro-2H-pyran-4-yloxy)propan-1-ol

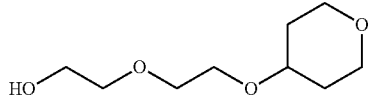

[Chemical formula 25]

(6a) 2-[2-(Benzyloxy)ethoxy]ethyl 4-methylbenzenesulfonate

Using 2-[2-(benzyloxy)ethoxy]ethanol (10.0 mL, 55.2 mmol), the desired title compound (18.7 g, yield 97%) was obtained by the same method as in Reference Example 2 (2c).

¹H-NMR (CDCl₃) δ: 2.43 (3H, s), 3.54-3.58 (2H, m), 3.59-3.63 (2H, m), 3.70 (2H, t, J=4.8 Hz), 4.17 (2H, t, J=4.8 Hz), 4.53 (2H, s), 7.26-7.36 (7H, m), 7.79 (2H, d, J=7.8 Hz).

(6b) 4-{2-[2-(Benzyloxy)ethoxy]ethoxy}tetrahydro-2H-pyran

Using tetrahydro-4-pyranol (0.784 mL, 8.23 mmol) and 2-[2-(benzyloxy)ethoxy]ethyl 4-methylbenzenesulfonate (1.92 g, 5.48 mmol) synthesized in Reference Example 6 (6a), the desired title compound (1.31 g, yield 85%) was obtained by the same method as in Reference Example 2 (2a).

¹H-NMR (CDCl₃) δ: 1.55-1.64 (2H, m), 1.87-1.93 (2H, m), 3.38-3.45 (2H, m), 3.48-3.55 (1H, m), 3.62-3.71 (8H, m), 3.91-3.96 (2H, m), 4.57 (2H, s), 7.26-7.36 (5H, m).

(6c) 2-[2-(Tetrahydro-2H-pyran-4-yloxy)ethoxy]ethanol

Using 4-{2-[2-(benzyloxy)ethoxy]ethoxy}tetrahydro-2H-pyran (1.31 g, 4.67 mmol) synthesized in Reference Example 6 (6b), the desired title compound (889 mg, yield 100%) was obtained by the same method as in Reference Example 5 (5b).

¹H-NMR (CDCl₃) δ: 1.56-1.66 (2H, m), 1.89-1.95 (2H, m), 2.50 (1H, br s), 3.40-3.47 (2H, m), 3.50-3.57 (1H, m), 3.62-3.67 (4H, m), 3.68-3.72 (2H, m), 3.72-3.76 (2H, m), 3.92-3.98 (2H, m).

MS(FAB) m/z: 191 (M+H)⁺

Reference Example 7

Tert-butyl 4-(2-hydroxyethoxy)benzoate

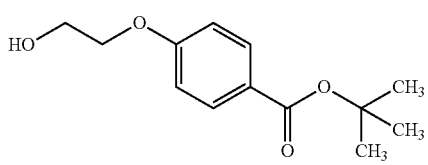

[Chemical formula 26]

(7a) Tert-butyl 4-hydroxybenzoate

Into tert-butyl alcohol (200 mL), 4-hydroxybenzoic acid (10.0 g, 72.4 mmol) and 4-dimethylaminopyridine (354 mg, 2.90 mmol) were dissolved, to which 1-ethyl-3-(3-dimethylaminopropyl)carbodiimide hydrochloride (15.3 g, 79.6 mmol) was added, followed by stirring overnight under a nitrogen atmosphere.

The resulting reaction liquid was concentrated under reduced pressure, to which ethyl acetate and hexane were added, followed by decantation. The resulting liquid was concentrated under reduced pressure again, and the residue thus obtained was purified by silica gel column chromatography (hexane:ethyl acetate, 100:0-70:30, V/V) to give the desired title compound (5.48 g, yield 39%).

$^1$H-NMR (CDCl$_3$) δ: 1.59 (9H, s), 6.18 (1H, s), 6.85 (2H, d, J=8.3 Hz), 7.90 (2H, d, J=8.3 Hz).

MS(ESI) m/z: 193 (M−H)$^-$

(7b) Tert-butyl 4-[2-(benzyloxy)ethoxy]benzoate

Using tert-butyl 4-hydroxybenzoate (2.00 g, 10.3 mmol) synthesized in Reference Example 7 (7a) and [(3-bromoethoxy)methyl]benzene (2.44 mL, 15.5 mmol), the desired title compound (2.49 g, yield 74%) was obtained by the same method as in Reference Example 2 (2a).

$^1$H-NMR (CDCl$_3$) δ: 1.58 (9H, s), 3.84 (2H, t, J=4.8 Hz), 4.19 (2H, t, J=4.8 Hz), 4.64 (2H, s), 6.91 (2H, d, J=8.7 Hz), 7.27-7.38 (5H, m), 7.93 (2H, d, J=8.7 Hz).

MS(ESI) m/z: 351 (M+Na)$^+$

(7c) Tert-butyl 4-(2-hydroxyethoxy)benzoate

Using tert-butyl 4-[2-(benzyloxy)ethoxy]benzoate (2.49 g, 7.58 mmol) synthesized in reference Example 7 (7b), the desired title compound (1.81 g, yield 100%) was obtained by the same method as in Reference Example 5 (5b).

$^1$H-NMR (CDCl$_3$) δ: 1.58 (9H, s), 2.00 (1H, t, J=6.2 Hz), 3.97-4.02 (2H, m), 4.13 (2H, t, J=4.4 Hz), 6.92 (2H, d, J=9.2 Hz), 7.94 (2H, d, J=9.2 Hz).

MS(FAB) m/z: 239 (M+H)$^+$

Reference Example 8

4-(2-Hydroxyethoxy)-N,N-dimethylbenzamide

[Chemical formula 27]

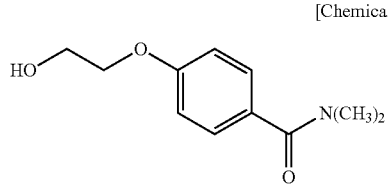

Dimethylamine hydrochloride (1.14 g, 14.0 mmol) was suspended in toluene (20.0 mL), to which a 2.0 M trimethylaluminium/heptane solution (6.25 mL, 12.5 mmol) was added dropwise at 0° C. under a nitrogen atmosphere. The resulting solution was warmed to room temperature, followed by stirring at room temperature for 30 minutes. Then, methyl 4-(2-hydroxyethoxy)benzoate (981 mg, 5.00 mmol) was added, followed by stirring at 55° C. for two hours.

To the resulting reaction liquid, sodium sulfate decahydrate was added, followed by stirring. A solid precipitate was filtered off. The resulting organic layer was concentrated under reduced pressure, and the residue thus obtained was purified by silica gel column chromatography (hexane:ethyl acetate, 100:0-0:100, V/V) to give the desired title compound (835 mg, yield 80%).

$^1$H-NMR (CDCl$_3$) δ: 2.12 (1H, t, J=6.2 Hz), 3.06 (6H, br s), 3.96-4.00 (2H, m), 4.10 (2H, t, J=4.6 Hz), 6.92 (2H, d, J=8.7 Hz), 7.40 (2H, d, J=8.7 Hz).

MS(FAB) m/z: 210 (M+H)$^+$

Reference Example 9

2-[4-(Morpholin-4-ylcarbonyl)phenoxy]ethanol

[Chemical formula 28]

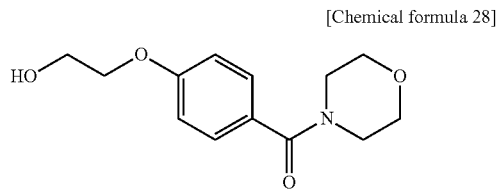 [SMILES: O=C(c1ccc(OCCO)cc1)N1CCOCC1]

Using morpholine (1.25 mL, 14.3 mmol) and methyl 4-(2-hydroxyethoxy)benzoate (1.00 g, 5.10 mmol), the desired title compound (345 mg, yield 27%) was obtained by the same method as in Reference Example 8.

$^1$H-NMR (CDCl$_3$) δ: 2.00 (1H, t, J=6.2 Hz), 3.54-3.77 (8H, m), 3.96-4.01 (2H, m), 4.11 (2H, t, J=4.6 Hz), 6.94 (2H, d, J=8.3 Hz), 7.39 (2H, d, J=8.3 Hz).

MS(ESI) m/z: 252 (M+H)$^+$

Reference Example 10

1-Acetyl-4-[4-(4,4,5,5-tetramethyl-1,3,2-dioxaborolan-2-yl)phenyl]piperidin-4-ol

[Chemical formula 29]

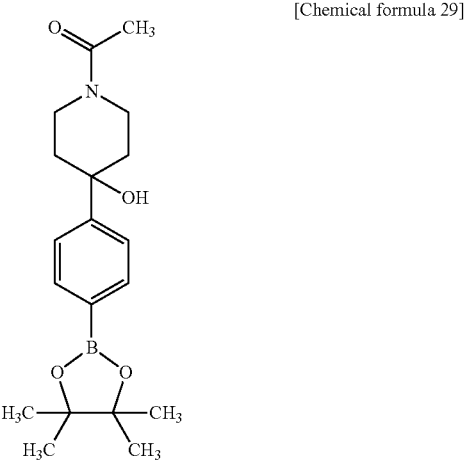

(10a) 1-Acetyl-4-(4-bromophenyl)piperidin-4-ol

Into dichloromethane (40.0 mL), 4-(4-bromophenyl)piperidin-4-ol (2.00 g, 7.81 mmol) was dissolved, to which triethylamine (2.72 mL, 19.5 mmol) was added. Acetyl chloride (0.833 mL, 11.7 mmol) was further added at 0° C., followed by stirring at room temperature overnight under a nitrogen atmosphere.

To the resulting reaction liquid, water was added, followed by extraction with dichloromethane. The resulting organic layer was concentrated under reduced pressure. The residue thus obtained was purified by basic silica gel column chromatography (hexane:ethyl acetate, 50:50-0:100, V/V) to give the desired title compound (1.85 g, yield 80%).

$^1$H-NMR (CDCl$_3$) δ: 1.59 (1H, s), 1.68-1.79 (2H, m), 1.84-2.01 (2H, m), 2.10 (3H, s), 2.99-3.07 (1H, m), 3.51-3.59 (1H, m), 3.66-3.72 (1H, m), 4.53-4.59 (1H, m), 7.30 (2H, d, J=8.6 Hz), 7.46 (2H, d, J=8.6 Hz).

(10b) 1-Acetyl-4-[4-(4,4,5,5-tetramethyl-1,3,2-dioxaborolan-2-yl)phenyl]piperidin-4-ol Using 1-acetyl-4-(4-bromophenyl)piperidin-4-ol (1.74 g, 5.82 mmol), the desired title compound (1.80 g, yield 89%) was obtained by the same method as in Reference Example 1 (1b).

$^1$H-NMR (CDCl$_3$) δ: 1.31 (12H), 1.58 (1H, s), 1.70-1.80 (2H, m), 1.90-2.04 (2H, m), 2.10 (3H, s), 3.01-3.09 (1H, m), 3.53-3.61 (1H, m), 3.65-3.72 (1H, m), 4.52-4.58 (1H, m), 7.43 (2H, d, J=8.4 Hz), 7.78 (2H, d, J=8.4 Hz).

Reference Example 11

2-[4-(2-Isopropoxyethoxy)phenyl]-4,4,5,5-tetramethyl-1,3,2-dioxaborolane

[Chemical formula 30]

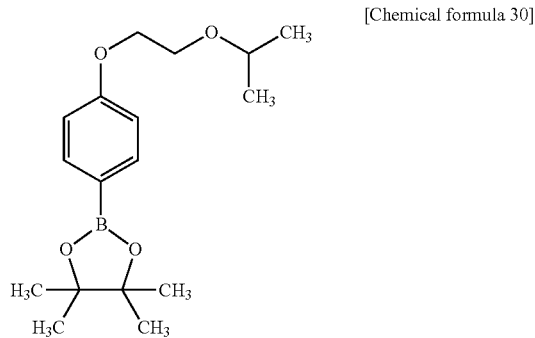 [SMILES: CC(C)OCCOc1ccc(B2OC(C)(C)C(C)(C)O2)cc1]

Using 4-(4,4,5,5-tetramethyl-1,3,2-dioxaborolan-2-yl)phenol (609 mg, 2.76 mmol) and ethylene glycol monoisopropyl ether (432 mg, 4.15 mmol), the desired title compound (100 mg, yield 31%) was obtained by the same method as in Example 2 (2a).

$^1$H-NMR (CDCl$_3$) δ: 1.19 (3H, s), 1.20 (3H, s), 1.33 (12H, s), 3.65-3.71 (1H, m), 3.78 (2H, t, J=5.1 Hz), 4.13 (2H, t, J=5.1 Hz), 6.91 (2H, d, J=8.8 Hz), 7.73 (2H, d, J=8.8 Hz).
MS (FAB) m/z: 307 (M+H)$^+$.

Reference Example 12

2-{2-[3-Fluoro-4-(4,4,5,5-tetramethyl-1,3,2-dioxaborolan-2-2-yl)phenoxy]ethoxy}tetrahydro-2H-pyran

[Chemical formula 31]

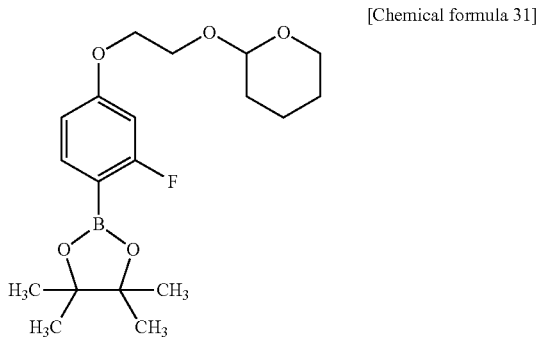 [SMILES: CC1(C)OB(c2ccc(OCCOC3CCCCO3)cc2F)OC1(C)C]

(12a) 2-[2-{4-Bromo-3-fluorophenoxy}ethoxy]tetrahydro-2H-pyran

Using 4-bromo-3-fluorophenol (5.00 g, 26.2 mmol), the desired title compound (7.10 g, yield 85%) was obtained by the same method as in Example 2 (2a).

$^1$H-NMR (CDCl$_3$) δ: 1.47-1.92 (6H, m), 3.48-3.59 (1H, m), 3.76-3.95 (2H, m), 4.01-4.18 (3H, m), 4.69 (1H, t, J=3.5 Hz), 6.61-6.79 (2H, m), 1.46 (1H, t, J=8.4 Hz).
MS (FAB) m/z: 320 (M+H)$^+$.

(12b) 2-{2-[3-Fluoro-4-(4,4,5,5-tetramethyl-1,3,2-dioxaborolan-2-2-yl)phenoxy]ethoxy}tetrahydro-2H-pyran Using 2-[2-{4-bromo-3-fluorophenoxy}ethoxy]tetrahydro-2H-pyran (1.59 g, 5.00 mmol) produced in Reference Example 12 (12a), the desired title compound (1.18 mg, yield 64%) was obtained by the same method as in Reference Example 1 (1b).

$^1$H-NMR (CDCl$_3$) δ: 1.33 (12H, s), 1.49-1.67 (4H, m), 1.69-1.89 (2H, m), 3.49 (1H, s), 3.77-3.85 (1H, m), 3.85-3.92 (1H, m), 4.02-4.07 (1H, m), 4.11-4.21 (2H, m), 4.70 (1H, t, J=3.5 Hz), 6.60 (1H, dd, J=11.2, 2.2 Hz), 6.71 (1H, dd, J=8.4, 2.3 Hz), 7.64 (1H, t, J=7.8 Hz).
MS (FAB) m/z: 367 (M+H)$^+$.

Reference Example 13

2-{[4-(Morpholin-4-ylcarbonyl)cyclohexyl]oxy}ethanol

[Chemical formula 32]

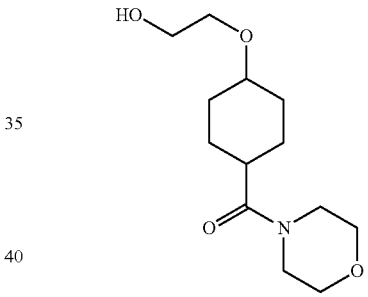

(13a) 4-({4-[2-(Benzyloxy)ethoxy]cyclohexyl}carbonyl)morpholine

Using morpholine (2.45 mL, 28.0 mmol) and ethyl 4-hydroxycyclohexane carboxylate (1.61 mL, 10.0 mmol), an alcohol intermediate was obtained by the same method as in Example 5. This intermediate was reacted with 2-(benzyloxy)ethyl 4-methylbenzenesulfonate (4.0 g, 13.0 mmol) without isolation by the same method as in Reference Example 2 (2a) to give the desired title compound (1.96 g, yield 56%).

$^1$H-NMR (CDCl$_3$) δ: 1.20-1.52 (3H, m), 1.75-2.06 (3H, m), 2.11-2.50 (2H, m), 3.25-3.74 (14H, m), 4.57-4.60 (2H, m), 7.25-7.37 (5H, m).
MS (FAB) m/z: 348 (M+H)$^+$.

(13b) 2-{[4-(Morpholin-4-ylcarbonyl)cyclohexyl]oxy}ethanol

Using 4-({4-[2-(benzyloxy)ethoxy]cyclohexyl}carbonyl)morpholine (1.96 g, 5.65 mmol) synthesized in Reference Example 13 (13a), the desired title compound (1.45 g, yield 99%) was obtained by the same method as in Reference Example 5 (5b).

$^1$H-NMR (CDCl$_3$) δ: 1.20-1.53 (3H, m), 1.56-1.61 (1H, m), 1.77-2.05 (4H, m), 2.11-2.21 (1H, m), 2.39-2.51 (1H, m), 3.47-3.54 (3H, m), 3.58-3.76 (10H, m).
MS (FAB) m/z: 258 (M+H)$^+$.

Reference Example 14

4-(2-Hydroxyethoxy)-N,N-dimethylcyclohexanecarboxamide

[Chemical formula 33]

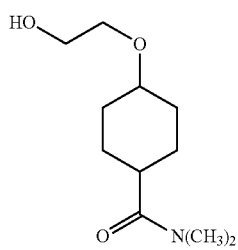

(14a) 4-[2-(Benzyloxy)ethoxy]-N,N-dimethylcyclohexanecarboxamide

Using ethyl 4-hydroxycyclohexanecarboxamide (1.61 mL, 10.0 mmol) and dimethylamine hydrochloride (2.28 g, 28.0 mmol), the desired title compound (1.43 g, yield 47%) was obtained by the same method as in Reference Example 13 (13a).

$^1$H-NMR (CDCl$_3$) δ: 1.21-1.32 (1H, m), 1.37-1.64 (3H, m), 1.79-1.81 (1H, m), 1.87-2.06 (2H, m), 2.10-2.18 (1H, m), 2.42-2.55 (1H, m), 2.93 (3H, s), 3.04 (3H, s), 3.26-3.68 (5H, m), 4.58-4.59 (2H, m), 7.27-7.37 (5H, m).

MS (FAB) m/z: 306 (M+H)$^+$.

(14b) 4-(2-Hydroxyethoxy))-N,N-dimethylcyclohexanecarboxamide

Using 4-[2-(benzyloxy)ethoxy]-N,N-dimethylcyclohexanecarboxamide (1.42 g, 4.64 mmol) produced in Reference Example 14 (14a), the desired title compound (996 mg, yield 99%) was obtained by the same method as in Reference Example 5 (5b).

$^1$H-NMR (CDCl$_3$) δ: 1.21-1.63 (4H, m), 1.80-2.16 (5H, m), 2.44-2.57 (1H, m), 2.92 (3H, s), 3.06 (3H, s), 3.28-3.60 (3H, m), 3.71-3.72 (2H, m).

MS (FAB) m/z: 216 (M+H)$^-$.

Reference Example 15

4-(2-Hydroxyethoxy)-N,N-dimethyltetrahydro-2H-pyran-4-carboxamide

[Chemical formula 34]

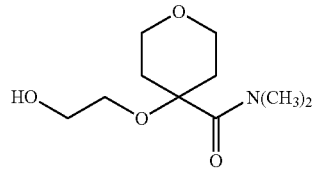

(15a) 1,4,9-Trioxaspiro[5.5]undecane-5-one

Into dichloromethane (40 mL), 1,4,8-trioxaspiro[4.5]decane (2.75 g, 19.1 mmol) was dissolved, to which trimethylcyanide (4.8 mL, 38.2 mmol) and zinc iodide (609 mg, 1.91 mmol) were added, followed by stirring at room temperature for 30 minutes. The resulting reaction liquid was concentrated under reduced pressure. To the residue thus obtained, a 1M aqueous solution of sodium hydroxide (40 mL) was added, followed by heating at 110° C. for three hours. The reaction liquid was cooled to room temperature and made acidic with concentrated hydrochloric acid, and concentrated under reduced pressure. To the residue thus obtained, dichloromethane was added, followed by stirring. A solid was filtered off and the filtrate was concentrated under reduced pressure to give the desired title compound (2.71 g, yield 82%).

$^1$H-NMR (CDCl$_3$) δ: 1.79-1.87 (2H, m), 2.18-2.29 (2H, m), 3.69-3.78 (2H, m), 3.80-3.88 (2H, m), 3.89-3.96 (2H, m), 4.44-4.51 (2H, m).

MS (FAB) m/z: 173 (M+H)$^+$.

(15b) 4-(2-Hydroxyethoxy)-N,N-dimethyltetrahydro-2H-pyran-4-carboxamide

Using 1,4,9-trioxaspiro[5.5]undecane-5-one produced in Reference Example 15 (15a) and dimethylamine hydrochloride (659 mg, 8.14 mmol), the desired title compound (630 mg, yield 99%) was obtained by the same method as in Example 5.

$^1$H-NMR (CDCl$_3$) δ: 1.86-1.97 (3H, m), 2.11-2.23 (2H, m), 2.97 (3H, s), 3.31 (3H, s), 3.41 (2H, t, J=4.6 Hz), 3.74-3.81 (6H, m).

MS (FAB) m/z: 218 (M+H)$^+$.

Reference Example 16

4-{[4-(4,4,5,5-Tetramethyl-1,3,2-dioxaborolan-2-yl)phenyl]acetyl}morpholine

[Chemical formula 35]

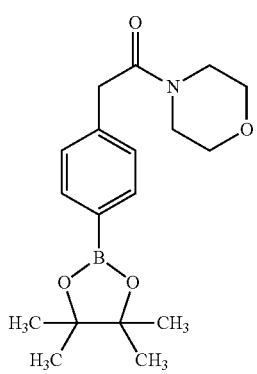

Using 4-(4,4,5,5-tetramethyl-1,3,2-dioxaborolan-2-yl)phenylacetic acid (786 mg, 3.0 mmol) and morpholine (1.3 mL, 15.0 mmol), the desired title compound (346 mg, yield 35%) was obtained by the same method as the amidation step in Example 4 (4b).

$^1$H-NMR (CDCl$_3$) δ: 1.25-1.41 (14H, m), 1.47-1.64 (2H, m), 3.33 (2H, t, J=5.5 Hz), 3.56 (2H, t, J=5.5 Hz), 3.75 (2H, s), 7.26 (2H, d, J=8.0 Hz), 7.76 (2H, d, J=8.0 Hz).

MS (FAB) m/z: 332 (M+H)$^+$.

Reference Example 17

2-{[1-(Methanesulfonyl)piperidin-4-yl]oxy}ethanol

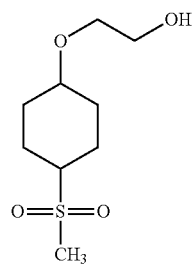

[Chemical formula 36]

(17a) Benzyl 4-[2-(tetrahydro-2H-pyran-2-yloxy)ethoxy]piperidine-1-carboxylate Using benzyl 4-hydroxy-1-piperidinecarboxylate (1.50 g, 6.35 mmol) and 2-(2-bromoethoxy)tetrahydro-2H-pyran (1.92 mL, 12.7 mmol), the desired title compound (1.2 g, yield 52%) was obtained by the same method as in Reference Example 2 (2a).

$^1$H-NMR (CDCl$_3$, 400MHz) δ: 1.41-1.66 (6H, m), 1.66-1.91 (4H, m), 3.14-3.28 (2H, m), 3.44-3.67 (5H, m), 3.72-3.93 (4H, m), 4.61-4.67 (1H, m), 5.12 (2H, s), 7.27-7.43 (5H, m).

(17b) 4-[2-(Tetrahydro-2H-pyran-2-yloxy)ethoxy]piperidine

Using benzyl 4-[2-(tetrahydro-2H-pyran-2-yloxy)ethoxy]piperidine-1-carboxylate (1.50 g, 3.15 mmol) synthesized in (17a), the desired title compound (578 mg, yield 80%) was obtained by the same method as in Reference Example 5 (5b).

$^1$H-NMR (CDCl$_3$, 400MHz) δ: 1.37-1.66 (7H, m), 1.68-1.98 (4H, m), 2.55-2.66 (2H, m), 3.05-3.13 (2H, m), 3.35-3.47 (1H, m), 3.47-3.57 (1H, m), 3.57-3.74 (3H, m), 3.79-3.96 (2H, m), 4.60-4.73 (1H, m).

(17c) 1-(Methylsulfonyl)-4-[2-(tetrahydro-2H-pyran-2-yloxy)ethoxy]piperidine Using 4-[2-(tetrahydro-2H-pyran-2-yloxy)ethoxy]piperidine (561 mg, 2.54 mmol) synthesized in (17b) and methanesulfonyl chloride (375 µL, 3.06 mmol), the desired title compound (618 mg, yield 83%) was obtained by the same method as in Reference Example 2 (2c).

(17d) 2-{[1-(Methanesulfonyl)piperidin-4-yl]oxy}ethanol

Using 1-(methylsulfonyl)-4-[2-(tetrahydro-2H-pyran-2-yloxy)ethoxy]piperidine (610 mg, 1.98 mmol) synthesized in (17c), the desired title compound (357 mg, yield 81%) was obtained by the same method as in Reference Example 2 (2b).

$^1$H-NMR (CDCl$_3$, 400MHz) δ: 1.74-1.86 (2H, m), 1.90-1.99 (3H, m), 2.79 (3H, s), 3.14-3.22 (2H, m), 3.34-3.42 (2H, m), 3.53-3.61 (3H, m), 3.71-3.78 (2H, m).

Reference Example 18

Trans-4-(2-hydroxyethoxy)tetrahydrofuran-3-ol

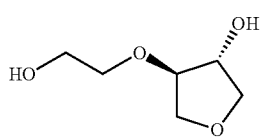

[Chemical formula 37]

The stereo chemistry of the structure only shows relative configuration

(18a) Trans-4-[2-(benzyloxy)ethoxy]tetrahydrofuran-3-ol

Into dichloromethane (5.0 mL), 2-benzyloxyethanol (7.07 g, 46.5 mmol) and 3,4-epoxytetrahydrofuran (1.0 g, 11.6 mmol) were dissolved, to which a boron trifluoride-diethyl ether complex (0.08 g, 0.58 mmol) was added at room temperature, followed by stirring for three hours. To the resulting reaction liquid, a saturated aqueous solution of sodium bicarbonate was added, followed by extraction with dichloromethane. The resulting organic layer was dried over anhydrous sodium sulfate and concentrated under reduced pressure. The residue thus obtained was purified by silica gel column chromatography (hexane:ethyl acetate, 100:0-0:100, V/V) to give the desired title compound (2.28 g, yield 82%).

$^1$H-NMR (CDCl$_3$) δ: 3.61-3.65 (2H, m), 3.69-3.77 (4H, m), 3.93-3.96 (1H, m), 3.97 (1H, dd, J=10.1, 4.6 Hz), 4.07 (1H, dd, J=10.1, 4.6 Hz), 4.30-4.34 (1H, m), 4.57 (2H, s), 7.27-7.38 (5H, m).

MS (EI$^+$) m/z: 239 (M+H)$^+$

(18b) Trans-4-(2-hydroxyethoxy)tetrahydrofuran-3-ol

Trans-4-[2-(benzyloxy)ethoxy]tetrahydrofuran-3-ol (2.20 g, 9.23 mmol) synthesized in (18a), ethyl vinyl ether (3.33 g, 46.2 mmol), and pyridinium paratoluene sulfonate (231 mg, 0.92 mmol) were dissolved in dichloromethane (22 ml), followed by stirring at room temperature for one hour. Triethylamine (187 mg, 1.84 mmol) was then added, and the resulting mixture was directly purified by silica gel column chromatography (hexane:ethyl acetate, 100:0-0:100, V/V) to give trans-3-[2-(benzyloxy)ethoxy]-4-(ethoxymethoxy)tetrahydrofuran (2.88 g, yield 100%). This compound (1.55 g, 5.00 mmol) was dissolved in methanol (30 ml), to which 20% palladium hydroxide-carbon (155 mg) was added, followed by stirring at room temperature for one hour under a hydrogen atmosphere. The resulting solution was concentrated under reduced pressure to give the desired title compound (725 mg, yield 98%).

¹H-NMR (CDCl₃) δ: 3.59-3.68 (2H, m), 3.72-3.76 (3H, m), 3.76-3.81 (1H, m), 3.93-3.97 (1H, m), 3.98 (1H, dd, J=10.1, 4.3 Hz), 4.07 (1H, dd, J=10.1, 4.3 Hz), 4.32-4.36 (1H, m).

MS (EI¹) m/z: 149 (M+H)⁺

Hereinbelow, the structural formulae and physicochemical data of compounds produced in Examples in accordance with the production methods of the aforementioned Examples 1 to 16 will be given.

"Ex No." refers to the number of Example, "STRUCTURE" refers to the structural formula of the compound of the Example, "METHOD" refers to, among the aforementioned general production methods, one used in the Example, and "DATA" refers to the physicochemical data of the compound produced in the Example.

TABLE 1

| Ex No. | STRUCTURE | METHOD | DATA |
|---|---|---|---|
| 17 | 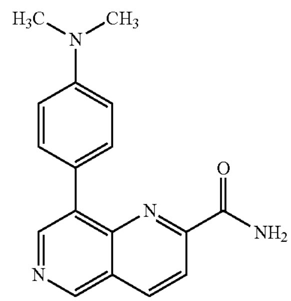 [SMILES: CN(C)c1ccc(-c2cncc3ccc(C(N)=O)nc23)cc1] | C | ¹H-NMR (DMSO-D₆) δ: 3.00 (6H, s), 6.90 (2H, d, J = 9.2 Hz), 7.62 (1H, br s), 7.73 (2H, d, J = 9.2 Hz), 8.01 (1H, br s), 8.28 (1H, d, J = 8.6 Hz), 8.80 (1H, d, J = 8.6 Hz), 8.82 (1H, s), 9.39 (1H, s). MS (EI) m/z: 292 (M)⁺ |
| 18 | 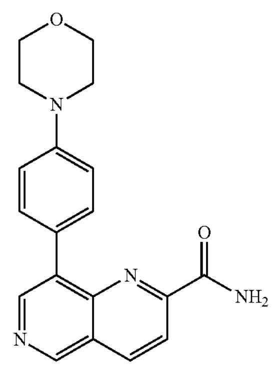 [SMILES: NC(=O)c1ccc2cncc(-c3ccc(N4CCOCC4)cc3)c2n1] | A | ¹H-NMR (DMSO-D₆) δ: 3.22-3.25 (4H, m), 3.77-3.80 (4H, m), 7.13 (2H, d, J = 8.6 Hz), 7.61 (1H, br s), 7.76 (2H, d, J = 8.6 Hz), 8.02 (1H, br s), 8.29 (1H, d, J = 8.6 Hz), 8.82 (1H, d, J = 8.6 Hz), 8.84 (1H, s), 9.43 (1H, s). MS (FAB) m/z: 335 (M + H)⁺ |
| 19 | 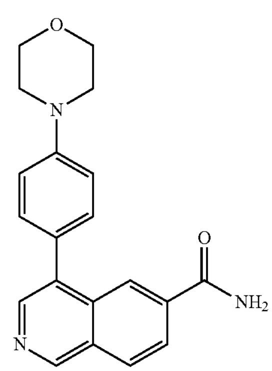 [SMILES: NC(=O)c1ccc2cncc(-c3ccc(N4CCOCC4)cc3)c2c1] | C | ¹H-NMR (DMSO-D₆) δ: 3.22-3.26 (4H, m), 3.76-3.81 (4H, m), 7.16 (2H, d, J = 8.3 Hz), 7.46 (2H, d, J = 8.3 Hz), 7.62 (1H, br s), 8.10 (1H, d, J = 8.5 Hz), 8.24 (1H, br s), 8.27 (1H, d, J = 8.5 Hz), 8.43 (1H, s), 8.47 (1H, s), 9.35 (1H, s). MS (EI) m/z: 333 (M)⁺ |
| 20 | 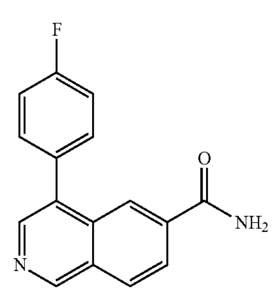 [SMILES: NC(=O)c1ccc2cncc(-c3ccc(F)cc3)c2c1] | C | ¹H-NMR (CDCl₃) δ: 5.70 (1H, br), 6.12 (1H, br), 7.21-7.28 (2H, m), 7.43-7.52 (2H, m), 8.03 (1H, d, J = 8.5 Hz), 8.15 (1H, d, J = 8.5 Hz), 8.30 (1H, s), 8.55 (1H, s), 9.33 (1H, s). MS (EI) m/z: 266 (M)⁺ |

TABLE 1-continued

| Ex No. | STRUCTURE | METHOD | DATA |
| --- | --- | --- | --- |
| 21 | 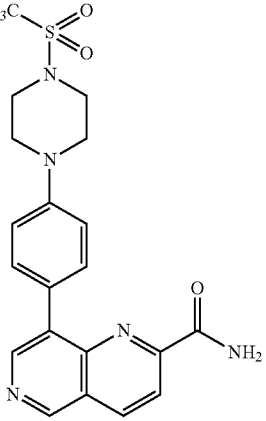 | A | 11H-NMR (CDCl3) : 2.86 (3H, s), 3.44 (8H, s), 5.58 (1H, br s), 7.11 (2H, d, J = 8.8 Hz), 7.72 (2H, d, J = 8.8 Hz), 7.80 (1H, br s), 8.46 (1H, d, J = 8.3 Hz), 8.54 (1H, d, J = 8.3 Hz), 8.87 (1H, s), 9.32 (1H, s).<br>MS (ESI) m/z: 412 (M + H)+ |

TABLE 2

| Ex No. | STRUCTURE | METHOD | DATA |
| --- | --- | --- | --- |
| 22 | 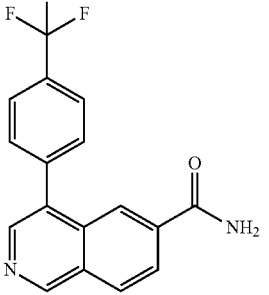 | C | $^1$H-NMR (DMSO-D$_6$) δ: 7.64 (1H, br s), 7.83 (2H, d, J = 8.0 Hz), 7.96 (2H, d, J = 8.0 Hz), 8.16 (1H, d, J = 8.6 Hz), 8.27 (1H, br s), 8.30 (1H, s), 8.34 (1H, d, J = 8.6 Hz), 8.56 (1H, s), 9.47 (1H, s).<br>MS (EI) m/z: 316 (M)+ |
| 23 | 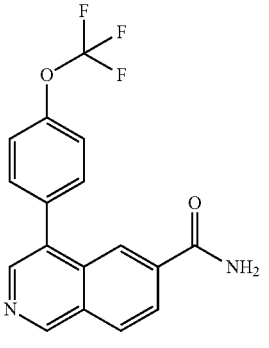 [SMILES: NC(=O)c1ccc2cncc(-c3ccc(OC(F)(F)F)cc3)c2c1] | C | $^1$H-NMR (DMSO-D$_6$) δ: 7.60 (2H, d, J = 8.3 Hz), 7.64 (1H, br s), 7.74 (2H, d, J = 8.3 Hz), 8.15 (1H, d, J = 8.3 Hz), 8.28 (1H, br s), 8.32 (1H, s), 8.32 (1H, d, J = 8.3 Hz), 8.54 (1H, s), 9.45 (1H, s).<br>MS (EI) m/z: 332 (M)+ |
| 24 | 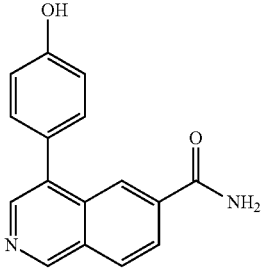 [SMILES: NC(=O)c1ccc2cncc(-c3ccc(O)cc3)c2c1] | C | $^1$H-NMR (DMSO-D$_6$) δ: 6.97 (2H, d, J = 8.5 Hz), 7.38 (2H, d, J = 8.5 Hz), 7.60 (1H, br s), 8.10 (1H, d, J = 8.5 Hz), 8.22 (1H, br s), 8.26 (1H, d, J = 8.5 Hz), 8.39 (1H, s), 8.45 (1H, s), 9.35 (1H, s), 9.73 (1H, s).<br>MS (EI) m/z: 264 (M)+ |

TABLE 2-continued

| 25 | 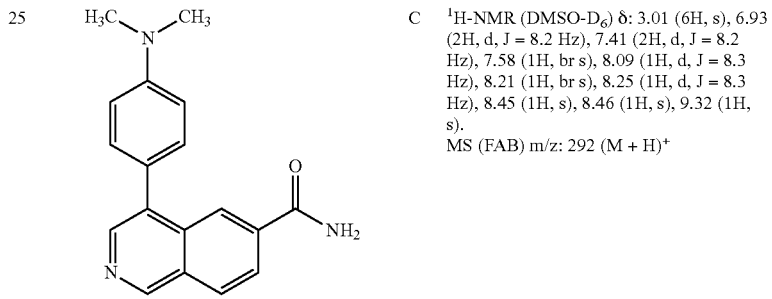 | C | $^1$H-NMR (DMSO-D$_6$) δ: 3.01 (6H, s), 6.93 (2H, d, J = 8.2 Hz), 7.41 (2H, d, J = 8.2 Hz), 7.58 (1H, br s), 8.09 (1H, d, J = 8.3 Hz), 8.21 (1H, br s), 8.25 (1H, d, J = 8.3 Hz), 8.45 (1H, s), 8.46 (1H, s), 9.32 (1H, s). MS (FAB) m/z: 292 (M + H)$^+$ |
| --- | --- | --- | --- |
| 26 | 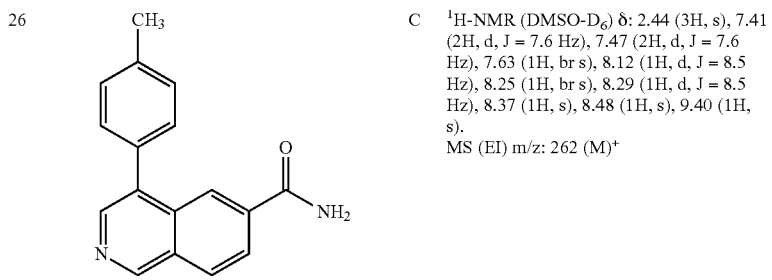 | C | $^1$H-NMR (DMSO-D$_6$) δ: 2.44 (3H, s), 7.41 (2H, d, J = 7.6 Hz), 7.47 (2H, d, J = 7.6 Hz), 7.63 (1H, br s), 8.12 (1H, d, J = 8.5 Hz), 8.25 (1H, br s), 8.29 (1H, d, J = 8.5 Hz), 8.37 (1H, s), 8.48 (1H, s), 9.40 (1H, s). MS (EI) m/z: 262 (M)$^+$ |
| 27 | 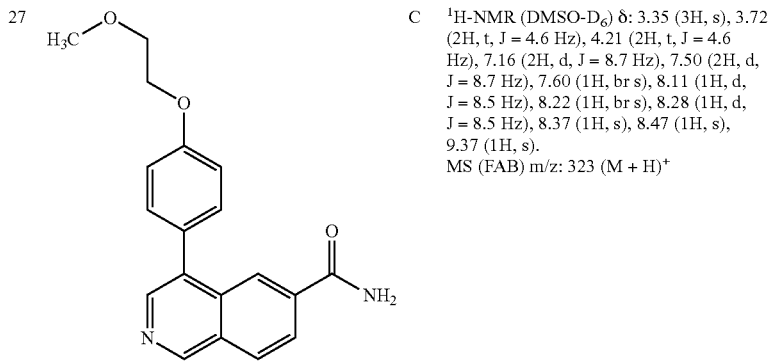 | C | $^1$H-NMR (DMSO-D$_6$) δ: 3.35 (3H, s), 3.72 (2H, t, J = 4.6 Hz), 4.21 (2H, t, J = 4.6 Hz), 7.16 (2H, d, J = 8.7 Hz), 7.50 (2H, d, J = 8.7 Hz), 7.60 (1H, br s), 8.11 (1H, d, J = 8.5 Hz), 8.22 (1H, br s), 8.28 (1H, d, J = 8.5 Hz), 8.37 (1H, s), 8.47 (1H, s), 9.37 (1H, s). MS (FAB) m/z: 323 (M + H)$^+$ |

TABLE 3

| 28 | 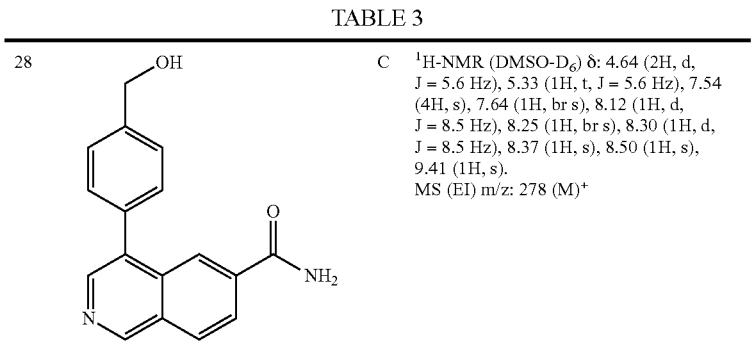 | C | $^1$H-NMR (DMSO-D$_6$) δ: 4.64 (2H, d, J = 5.6 Hz), 5.33 (1H, t, J = 5.6 Hz), 7.54 (4H, s), 7.64 (1H, br s), 8.12 (1H, d, J = 8.5 Hz), 8.25 (1H, br s), 8.30 (1H, d, J = 8.5 Hz), 8.37 (1H, s), 8.50 (1H, s), 9.41 (1H, s). MS (EI) m/z: 278 (M)$^+$ |
| --- | --- | --- | --- |

TABLE 3-continued
| 29 | 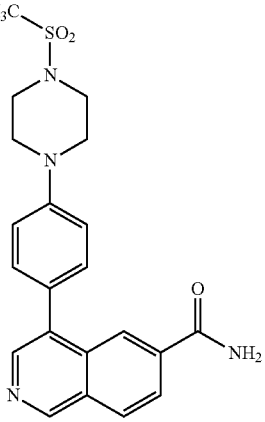 | C | ¹H-NMR (CDCl₃) δ: 2.87 (3H, s), 3.37-3.52 (8H, m), 5.69 (1H, br), 6.14 (1H, br), 7.10 (2H, d, J = 8.6 Hz), 7.45 (2H, d, J = 8.6 Hz), 7.99 (1H, d, J = 8.6 Hz), 8.12 (1H, d, J = 8.6 Hz), 8.41 (1H, s), 8.55 (1H, s), 9.29 (1H, s). MS (EI) m/z: 411 (M + H)⁺ |
| --- | --- | --- | --- |
| 30 | 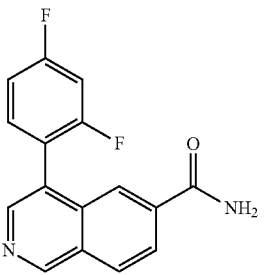 [SMILES: NC(=O)c1ccc2cncc(-c3ccc(F)cc3F)c2c1] | C | ¹H-NMR (DMSO-D₆) δ: 7.34 (1H, td, J = 8.3, 2.5 Hz), 7.53 (1H, td, J = 9.9, 2.5 Hz), 7.61-7.66 (2H, m), 8.10 (1H, br s), 8.16 (1H, d, J = 8.6 Hz), 8.29 (1H, br s), 8.32 (2H, d, J = 8.6 Hz), 8.52 (1H, s), 9.48 (1H, s). MS (EI) m/z: 284 (M)⁺ |
| 31 | 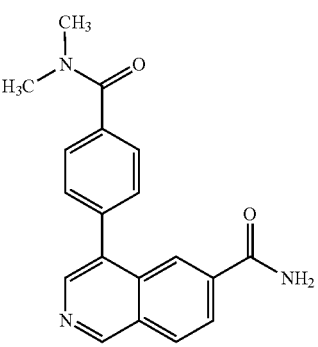 [SMILES: CN(C)C(=O)c1ccc(-c2cncc3ccc(C(N)=O)cc23)cc1] | C | ¹H-NMR (DMSO-D₆) δ: 2.99 (6H, s), 7.58 (2H, d, J = 8.2 Hz), 7.59 (1H, br s), 7.62 (2H, d, J = 8.2 Hz), 8.10 (1H, d, J = 8.6 Hz), 8.22 (1H, br s), 8.28 (1H, d, J = 8.6 Hz), 8.33 (1H, s), 8.50 (1H, s), 9.40 (1H, s). MS (FAB) m/z: 320 (M + H)⁺ |
| 32 | 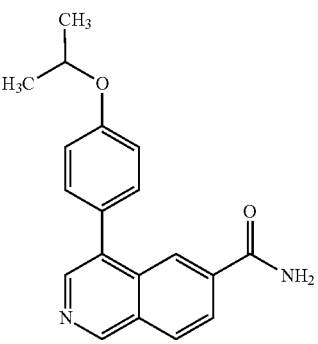 [SMILES: CC(C)Oc1ccc(-c2cncc3ccc(C(N)=O)cc23)cc1] | C | ¹H-NMR (DMSO-D₆) δ: 1.31 (6H, d, J = 6.3 Hz), 4.65-4.74 (1H, m), 7.08 (2H, d, J = 8.6 Hz), 7.44 (2H, d, J = 8.6 Hz), 7.60 (1H, br s), 8.07 (1H, d, J = 8.6 Hz), 8.21 (1H, s), 8.24 (1H, d, J = 8.6 Hz), 8.35 (1H, s), 8.43 (1H, s), 9.33 (1H, s). MS (FAB) m/z: 306 (M)⁺ |

TABLE 3-continued

| 33 | 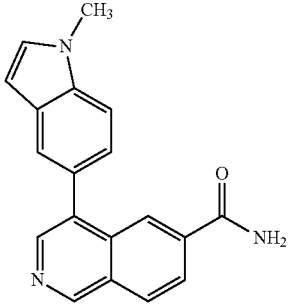 [SMILES: Cn1ccc2cc(-c3cncc4ccc(C(N)=O)cc34)ccc21] | C | ¹H-NMR (DMSO-D₆) δ: 3.89 (3H, s), 6.54 (1H, d, J = 2.9 Hz), 7.33 (1H, d, J = 8.5 Hz), 7.45 (1H, d, J = 2.9 Hz), 7.56 (1H, br s), 7.64 (1H, d, J = 8.5 Hz), 7.73 (1H, s), 8.10 (1H, d, J = 8.4 Hz), 8.18 (1H, br s), 8.28 (1H, d, J = 8.4 Hz), 8.43 (1H, s), 8.52 (1H, s), 9.37 (1H, s). MS (EI) m/z: 301 (M)⁺ |

TABLE 4

| 34 | 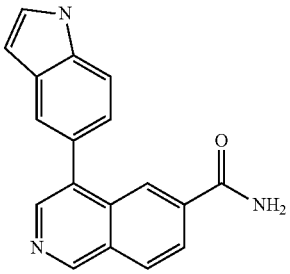 [SMILES: NC(=O)c1ccc2cncc(-c3ccc4[nH]ccc4c3)c2c1] | C | ¹H-NMR (DMSO-D₆) δ: 6.54-6.56 (1H, m), 7.26 (1H, d, J = 8.3 Hz), 7.46-7.48 (1H, m), 7.56 (1H, br s), 7.59 (1H, d, J = 8.3 Hz), 7.72 (1H, s), 8.10 (1H, d, J = 8.5 Hz), 8.19 (1H, br s), 8.27 (1H, d, J = 8.5 Hz), 8.44 (1H, s), 8.52 (1H, s), 9.37 (1H, s), 11.31 (1H, br s). MS (FAB) m/z: 288 (M + H)⁺ |
| 35 | 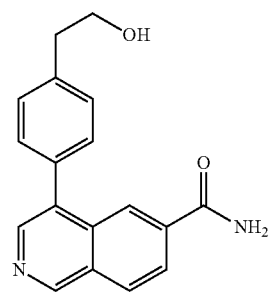 [SMILES: NC(=O)c1ccc2cncc(-c3ccc(CCO)cc3)c2c1] | C | ¹H-NMR (DMSO-D₆) δ: 2.86 (2H, t, J = 6.9 Hz), 3.69-3.75 (2H, m), 4.75 (1H, t, J = 4.8 Hz), 7.45 (2H, d, J = 8.0 Hz), 7.50 (2H, d, J = 8.0 Hz), 7.64 (1H, br s), 8.12 (1H, d, J = 8.7 Hz), 8.26 (1H, br s), 8.29 (1H, d, J = 8.7 Hz), 8.39 (1H, s), 8.49 (1H, s), 9.40 (1H, s). MS (FAB) m/z: 293 (M + H)⁺ |
| 36 | 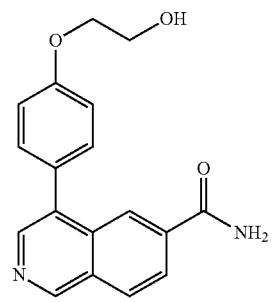 [SMILES: NC(=O)c1ccc2cncc(-c3ccc(OCCO)cc3)c2c1] | C | ¹H-NMR (DMSO-D₆) δ: 3.78 (2H, dt, J = 5.5, 5.0 Hz), 4.11 (2H, t, J = 5.0 Hz), 4.91 (1H, t, J = 5.5 Hz), 7.16 (2H, d, J = 8.5 Hz), 7.50 (2H, d, J = 8.5 Hz), 7.60 (1H, br s), 8.11 (1H, d, J = 8.5 Hz), 8.23 (1H, br s), 8.28 (1H, d, J = 8.5 Hz), 8.38 (1H, s), 8.47 (1H, s), 9.37 (1H, s). MS (EI) m/z: 308 (M)⁺ |
| 37 | 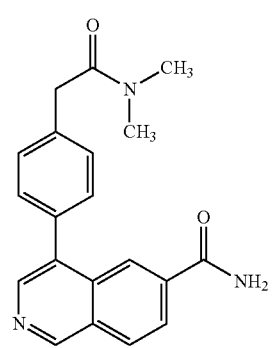 [SMILES: CN(C)C(=O)Cc1ccc(-c2cncc3ccc(C(N)=O)cc23)cc1] | C | ¹H-NMR (DMSO-D₆) δ: 2.86 (3H, s), 3.07 (3H, s), 3.80 (2H, s), 7.42 (2H, d, J = 8.2 Hz), 7.51 (2H, d, J = 8.2 Hz), 7.63 (1H, br s), 8.10 (1H, d, J = 8.6 Hz), 8.25 (1H, br s), 8.28 (1H, d, J = 8.6 Hz), 8.37 (1H, s), 8.48 (1H, s), 9.39 (1H, s). MS (FAB) m/z: 334 (M + H)⁺ |

TABLE 4-continued

| 38 | [structure: 1-acetyl-4-(4-phenyl)piperidine linked to isoquinoline-6-carboxamide] | C | ¹H-NMR (DMSO-D₆) δ: 1.48-1.60 (1H, m), 1.64-1.75 (1H, m), 1.85-1.95 (2H, m), 2.06 (3H, s), 2.59-2.68 (1H, m), 2.86-2.94 (1H, m), 3.13-3.22 (1H, m), 3.93-4.00 (1H, m), 4.55-4.61 (1H, m), 7.48 (2H, d, J = 8.0 Hz), 7.53 (2H, d, J = 8.0 Hz), 7.64 (1H, br s), 8.12 (1H, d, J = 8.7 Hz), 8.26 (1H, br s), 8.29 (1H, d, J = 8.7 Hz), 8.38 (1H, s), 8.50 (1H, s), 9.40 (1H, s). MS (FAB) m/z: 374 (M + H)⁺ |
|---|---|---|---|
| 39 | [structure: cyclopropylmethoxy-phenyl-isoquinoline-6-carboxamide] | C | ¹H-NMR (DMSO-D₆) δ: 0.32-0.41 (2H, m), 0.56-0.65 (2H, m), 1.21-1.34 (1H, m), 3.89-3.95 (2H, d, J = 6.8 Hz), 7.13 (2H, d, J = 7.9 Hz), 7.48 (2H, d, J = 7.9 Hz), 7.60 (1H, br s), 8.10 (1H, d, J = 8.5 Hz), 8.22 (1H, br s), 8.27 (1H, d, J = 8.5 Hz), 8.37 (1H, s), 8.46 (1H, s), 9.37 (1H, s). MS (FAB) m/z: 319 (M + H)⁺ |

TABLE 5

| 40 | [structure: N,N-dimethyl-3-(4-phenyl)propanamide linked to isoquinoline-6-carboxamide] | C | ¹H-NMR (DMSO-D₆) δ: 2.72 (2H, t, J = 7.8 Hz), 2.85 (3H, s), 2.93 (2H, t, J = 7.8 Hz), 2.99 (3H, s), 7.44-7.53 (4H, m), 7.62 (1H, br s), 8.11 (1H, d, J = 8.5 Hz), 8.24 (1H, br s), 8.29 (1H, d, J = 8.5 Hz), 8.38 (1H, s), 8.48 (1H, s), 9.40 (1H, s). MS (FAB) m/z: 348 (M + H)⁺ |
|---|---|---|---|
| 41 | [structure: 4-acetylphenyl-isoquinoline-6-carboxamide] | C | ¹H-NMR (DMSO-D₆) δ: 2.75 (3H, s), 7.68 (1H, br s), 7.81 (2H, d, J = 8.0 Hz), 8.18-8.26 (3H, m), 8.31 (1H, br s), 8.36-8.42 (2H, m), 8.61 (1H, s), 9.52 (1H, s). MS (FAB) m/z: 291 (M + H)⁺ |

TABLE 5-continued
| | | | |
|---|---|---|---|
| 42 | 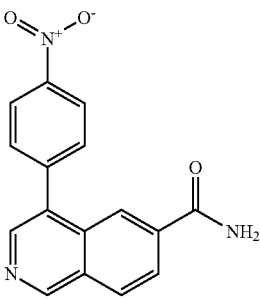 [SMILES: NC(=O)c1ccc2cncc(-c3ccc([N+](=O)[O-])cc3)c2c1] | C | ¹H-NMR (DMSO-D₆) δ: 7.63 (1H, br s), 7.89 (2H, d, J = 8.5 Hz), 8.16 (2H, d, J = 8.5 Hz), 8.24 (1H, br s), 8.28 (1H, s), 8.34 (1H, d, J = 8.5 Hz), 8.43 (2H, d, J = 8.5 Hz), 8.58 (1H, s), 9.48 (1H, s). MS (FAB) m/z: 294 (M + H)⁺ |
| 43 | 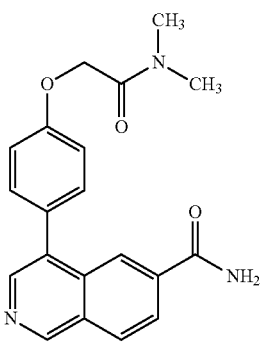 [SMILES: CN(C)C(=O)COc1ccc(-c2cncc3ccc(C(N)=O)cc23)cc1] | C | ¹H-NMR (DMSO-D₆) δ: 2.88 (3H, s), 3.05 (3H, s), 4.93 (2H, s), 7.13 (2H, d, J = 8.3 Hz), 7.50 (2H, d, J = 8.3 Hz), 7.60 (1H, br s), 8.11 (1H, d, J = 8.5 Hz), 8.23 (1H, br s), 8.28 (1H, d, J = 8.5 Hz), 8.39 (1H, s), 8.47 (1H, s), 9.37 (1H, s). MS (FAB) m/z 350 (M + H)⁺ |
| 44 | 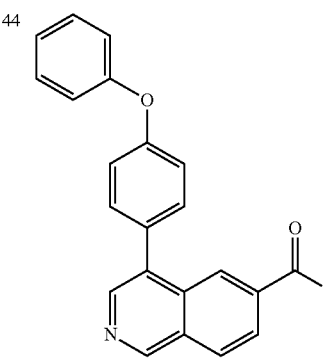 | C | ¹H-NMR (DMSO-D₆) δ: 7.13-7.25 (5H, m), 7.41-7.50 (2H, m), 7.55-7.64 (3H, m), 8.12 (1H, d, J = 8.5 Hz), 8.24 (1H, br s), 8.29 (1H, d, J = 8.5 Hz), 8.38 (1H, br s), 8.51 (1H, s), 9.40 (1H, s). MS (FAB) m/z: 341 (M + H)⁺ |
| 45 | 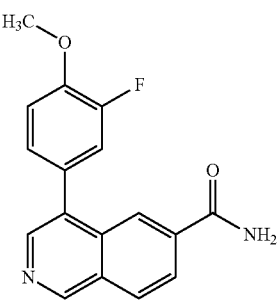 | C | ¹H-NMR (DMSO-D₆) δ: 3.95 (3H, s), 7.34-7.41 (2H, m), 7.45-7.53 (1H, m), 7.62 (1H, br s), 8.10-8.15 (1H, m), 8.26 (1H, br s), 8.29 (1H, d, J = 8.5 Hz), 8.36 (1H, s), 8.50 (1H, s), 9.40 (1H, s). MS (FAB) m/z: 297 (M + H)⁺ |

TABLE 6

| 46 | 4-chloro-3-fluorophenyl substituent | C | ¹H-NMR (DMSO-D₆) δ: 7.44-7.49 (1H, m), 7.63 (1H, br s), 7.69-7.74 (1H, m), 7.81 (1H, t, J = 8.0 Hz), 8.13-8.19 (1H, m), 8.27 (1H, br s), 8.30-8.36 (2H, m), 8.54 (1H, s), 9.45 (1H, s). MS (FAB) m/z: 301 (M + H)⁺ |
|---|---|---|---|
| 47 | 4-(methoxycarbonyl)phenyl substituent | C | ¹H-NMR (DMSO-D₆) δ: 3.91 (3H, s), 7.61 (1H, s), 7.74 (2H, d, J = 8.0 Hz), 8.13-8.16 (3H, m), 8.23 (1H, br s), 8.30-8.32 (2H, m), 8.54 (1H, s), 9.45 (1H, s). MS (FAB) m/z: 307 (M + H)⁺ |
| 48 | 4-(methylsulfonyl)phenyl substituent | C | ¹H-NMR (DMSO-D₆) δ: 3.36 (3H, s), 7.65 (1H, br s), 7.88 (2H, d J = 8.0 Hz), 8.08-8.14 (3H, m), 8.27 (1H, br s), 8.30 (1H, s), 8.33 (1H, d, J = 8.5 Hz), 8.55 (1H, s), 9.47 (1H, s). MS (FAB) m/z: 327 (M + H)⁺ |
| 49 | 4-(2,3-dihydroxypropoxy)phenyl substituent | C | ¹H-NMR (DMSO-D₆) δ: 3.49 (2H, t, J = 5.6 Hz), 3.83-3.88 (1H, m), 3.95-4.01 (1H, m), 4.07-4.14 (1H, m), 4.71 (1H, t, J = 5.6 Hz), 5.00 (1H, d, J = 4.9 Hz), 7.15 (2H, d, J = 8.5 Hz), 7.50 (2H, d, J = 8.5 Hz), 7.61 (1H, br s), 8.11 (1H, d, J = 8.4 Hz), 8.23 (1H, br s), 8.28 (1H, d, J = 8.4 Hz), 8.38 (1H, s), 8.47 (1H, s), 9.37 (1H, s). MS (FAB) m/z: 339 (M + H)⁺ |
| 50 | 4-chloro-2-fluorophenyl substituent | C | ¹H-NMR (DMSO-D₆) δ: 7.51-7.56 (1H, m), 7.60 (1H, t, J = 8.4 Hz), 7.63 (1H, br s), 7.69-7.74 (1H, m), 8.08 (1H, s), 8.15-8.19 (1H, m), 8.28 (1H, br s), 8.31 (1H, d, J = 8.5 Hz), 8.52 (1H, s), 9.47 (1H, s). MS (FAB) m/z: 301 (M + H)⁺ |

TABLE 6-continued

| 51 | 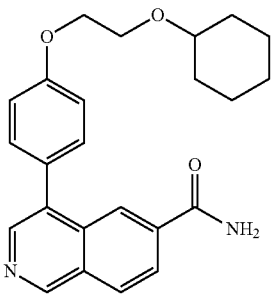 [SMILES: NC(=O)c1ccc2cncc(-c3ccc(OCCOC4CCCCC4)cc3)c2c1] | C | $^1$H-NMR (DMSO-D$_6$) δ: 1.20-1.32 (5H, m), 1.46-1.54 (1H, m), 1.65-1.74 (2H, m), 1.84-1.94 (2H, m), 3.35-3.41 (1H, m), 3.79 (2H, t, J = 4.8 Hz), 4.18 (2H, t, J = 4.8 Hz), 7.16 (2H, d, J = 8.7 Hz), 7.50 (2H, d, J = 8.7 Hz), 7.61 (1H, br s), 8.11 (1H, d, J = 8.5 Hz), 8.23 (1H, br s), 8.28 (1H, d, J = 8.5 Hz), 8.38 (1H, s), 8.47 (1H, s), 9.37 (1H, s). MS (FAB) m/z: 391 (M + H)$^+$ |
|---|---|---|---|

TABLE 7

| 52 | 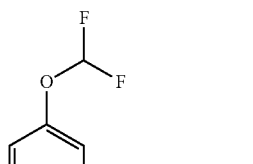 | C | $^1$H-NMR (DMSO-D$_6$) δ: 7.38 (1H, t, J = 74.0 Hz), 7.39 (2H, d, J = 7.9 Hz), 7.62 (1H, br s), 7.64 (2H, d, J = 7.9 Hz), 8.12 (1H, d, J = 8.7 Hz), 8.25 (1H, br s), 8.30 (1H, d, J = 8.7 Hz), 8.32 (1H, s), 8.49 (1H, s), 9.41 (1H, s). MS (EI) m/z: 314 (M)$^+$ |
|---|---|---|---|
| 53 | 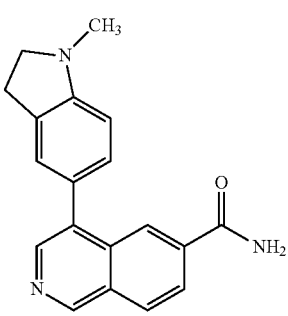 [SMILES: CN1CCc2cc(-c3cncc4ccc(C(N)=O)cc34)ccc21] | C | $^1$H-NMR (DMSO-D$_6$) δ: 2.80 (3H, s), 2.99 (2H, t, J = 8.3 Hz), 3.34 (2H, t, J = 8.3 Hz), 6.70 (1H, d, J = 7.8 Hz), 7.21 (1H, d, J = 7.8 Hz), 7.24 (1H, s), 7.61 (1H, br s), 8.08 (1H, d, J = 8.7 Hz), 8.23 (1H, br s), 8.24 (1H, d, J = 8.7 Hz), 8.43 (1H, s), 8.44 (1H, s), 9.31 (1H, s). MS (FAB) m/z: 304 (M + H)$^+$ |
| 54 | 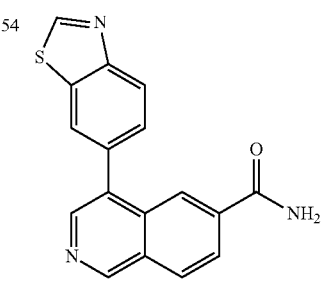 | C | $^1$H-NMR (DMSO-D$_6$) δ: 7.61 (1H, br s), 7.74 (1H, d, J = 8.7 Hz), 8.15 (1H, d, J = 8.7 Hz), 8.25 (1H, br s), 8.29 (1H, d, J = 8.7 Hz), 8.33 (1H, d, J = 8.7 Hz), 8.35 (1H, s), 8.43 (1H, s), 8.59 (1H, s), 9.46 (1H, s), 9.52 (1H, s). MS (EI) m/z: 305 (M)$^+$ |

TABLE 7-continued

| | | | |
|---|---|---|---|
| 55 | [structure] | C | ¹H-NMR (DMSO-D$_6$) δ: 3.47-3.52 (2H, m), 3.54-3.62 (6H, m), 3.85 (2H, s), 7.44 (2H, d, J = 8.1 Hz), 7.52 (2H, d, J = 8.1 Hz), 7.61 (1H, br s), 8.11 (1H, d, J = 8.5 Hz), 8.23 (1H, br s), 8.28 (1H, d, J = 8.5 Hz), 8.36 (1H, s), 8.49 (1H, s), 9.39 (1H, s). MS (FAB) m/z: 376 (M + H)⁺ |
| 56 | [structure] HCl | C | ¹H-NMR (DMSO-D$_6$) δ: 1.35-1.53 (2H, m), 1.85-1.94 (2H, m), 2.81 (3H, d, J = 4.4 Hz), 3.32-3.40 (2H, m), 3.56-3.66 (1H, m), 3.79-3.87 (4H, m), 4.20-4.25 (2H, m), 7.20 (2H, d, J = 8.8 Hz), 7.55 (2H, d, J = 8.8 Hz), 8.19 (1H, d, J = 8.5 Hz), 8.39 (1H, s), 8.45 (1H, d, J = 8.5 Hz), 8.57 (1H, s), 8.81 (1H, m), 9.60 (1H, s). MS (FAB) m/z: 407 (M + H)⁺ |
| 57 | [structure] | C | ¹H-NMR (DMSO-D$_6$) δ: 1.29 (6H, t, J = 7.1 Hz), 4.12-4.20 (4H, m), 4.55 (2H, d, J = 10.1 Hz), 7.26 (2H, d, J = 8.5 Hz), 7.53 (2H, d, J = 8.5 Hz), 7.63 (1H, br s), 8.11 (1H, d, J = 8.3 Hz), 8.25 (1H, br s), 8.29 (1H, d, J = 8.3 Hz), 8.36 (1H, s), 8.48 (1H, s), 9.39 (1H, s). MS (FAB) m/z: 415 (M + H)⁺ |

TABLE 8

| | | | |
|---|---|---|---|
| 58 | [structure] | A | ¹H-NMR(DMSO-D$_6$) δ: 1.39-1.50 (2H, m), 1.86-1.96 (2H, m), 3.40-3.65 (7H, m), 3.80-(4H, m), 4.14-4.22 (2H, m), 4.93 (1H, br s), 7.14 (2H, d, J = 8.5 Hz), 7.83 (2H, d, J = 8.5 Hz), 8.32 (1H, d, J = 8.3 Hz), 8.34 (1H, br s), 8.86 (1H, d, J = 8.3 Hz), 8.89 (1H, s) 9.47 (1H, s). MS (FAB) m/z: 438 (M + H)⁺ |

TABLE 8-continued

| 59 | 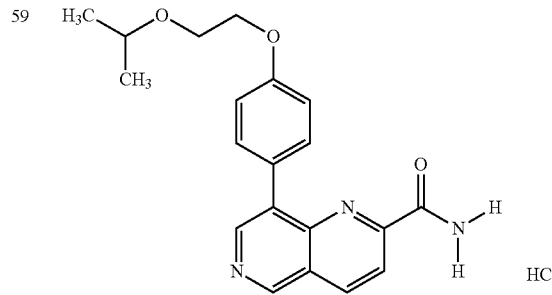 HCl | A | ¹H-NMR (DMSO-D₆) δ: 1.15 (6H, d J = 9.0 Hz), 3.63-3.69 (1H, m), 3.75 (2H, t, J = 4.8 Hz), 4.17 (2H, t, J = 4.8 Hz), 7.15 (2H, d, J = 8.8 Hz), 7.62 (1H, br s), 7.80 (2H, d, J = 8.8 Hz), 8.04 (1H, br s), 8.33 (1H, d, J = 8.5 Hz), 8.85-8.92 (2H, m), 9.53 (1H, s). MS (FAB) m/z: 352 (M + H)⁺ |
|---|---|---|---|
| 60 | 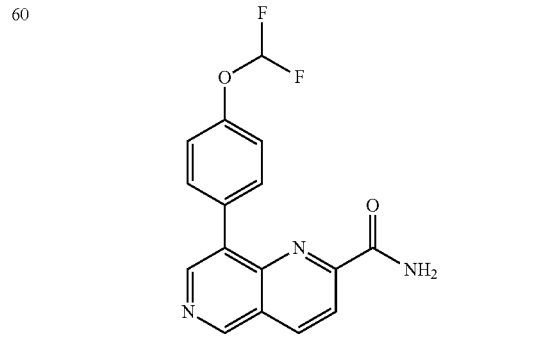 | A | ¹H-NMR (DMSO-D₆) δ: 7.37 (2H, d, J = 8.3 Hz), 7.37 (1H, t, J = 73.8 Hz), 7.63 (1H, br s), 7.93 (2H, d, J = 8.3 Hz), 8.02 (1H, br s), 8.32 (1H, d, J = 8.3 Hz), 8.86 (1H, d, J = 8.3 Hz), 8.89 (1H, s), 9.52 (1H, s). MS (FAB) m/z: 316 (M + H)⁺ |
| 61 | 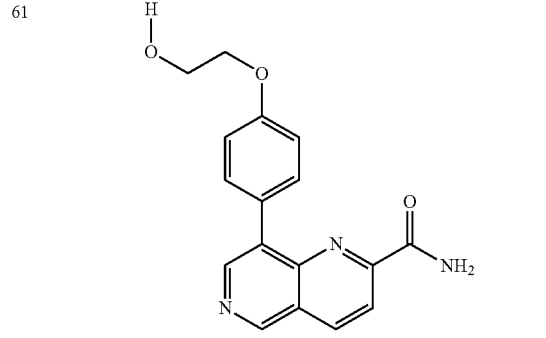 | A | ¹H-NMR (DMSO-D₆) δ: 3.74-3.80 (2H, m), 4.09 (2H, t, J = 5.0 Hz), 4.92 (1H, t, J = 5.4 Hz), 7.13 (2H, d, J = 8.8 Hz), 7.61 (1H, br s), 7.79 (2H, d, J = 8.8 Hz), 8.02 (1H, br s), 8.30 (1H, d, J = 8.5 Hz), 8.83 (1H, d, J = 8.5 Hz), 8.85 (1H, s), 9.46 (1H, s). MS (FAB) m/z: 310 (M + H)⁺ |
| 62 | 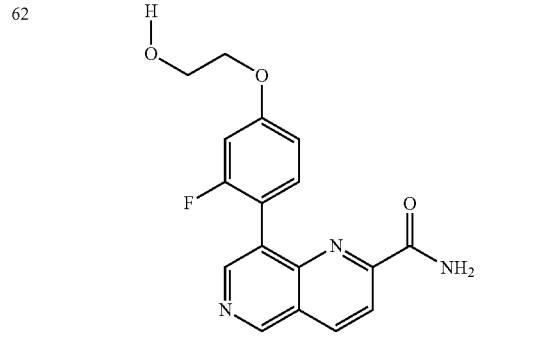 | A | ¹H-NMR (DMSO-D₆) δ: 3.74-3.80 (2H, m, J = 5.5, 4.9 Hz), 4.11 (2H, t, J = 4.9 Hz), 4.94 (1H, t, J = 5.5 Hz), 6.98 (1H, dd, J = 8.5, 2.4 Hz), 7.04 (1H, dd, J = 12.2, 2.4 Hz), 7.49 (1H, br s), 7.58 (1H, t, J = 8.5 Hz), 7.98 (1H, br s), 8.31 (1H, d, J = 8.5 Hz), 8.82 (1H, s), 8.85 (1H, d, J = 8.5 Hz), 9.54 (1H, s). MS (FAB) m/z: 328 (M + H)⁺ |
| 63 | 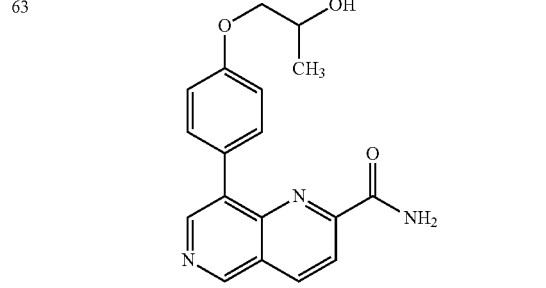 | A | ¹H-NMR (DMSO-D₆) δ: 1.19 (3H, d, J = 6.4 Hz), 3.87-3.95 (2H, m), 3.97-4.05 (1H, m), 4.94 (1H, d, J = 4.1 Hz), 7.13 (2H, d, J = 8.7 Hz), 7.62 (1H, br s), 7.79 (2H, d, J = 8.7 Hz), 8.02 (1H, br s), 8.30 (1H, d, J = 8.5 Hz), 8.83 (1H, d, J = 8.5 Hz), 8.85 (1H, s), 9.46 (1H, s). MS (FAB) m/z: 324 (M + H)⁺ |

TABLE 9

| 64 | [structure] | B | ¹H-NMR (DMSO-D$_6$) δ: 1.27 (3H, d, J = 6.4 Hz), 3.49-3.54 (1H, m), 3.59-3.64 (1H, m), 4.50-4.57 (1H, m), 4.90-4.95 (1H, m), 7.13 (2H, d, J = 8.9 Hz), 7.63 (1H, br s), 7.78 (2H, d, J = 8.9 Hz), 8.02 (1H, br s), 8.30 (1H, d, J = 8.5 Hz), 8.83 (1H, d, J = 8.5 Hz), 8.85 (1H, s), 9.46 (1H, s). MS (FAB) m/z: 324 (M + H)⁺ |
| --- | --- | --- | --- |
| 65 | [structure] | A | ¹H-NMR (DMSO-D$_6$) δ: 3.27 (3H, s), 3.49 (2H, t, J = 4.8 Hz), 3.62 (2H, t, J = 4.8 Hz), 3.79 (2H, t, J = 4.6 Hz), 4.19 (2H, t, J = 4.6 Hz), 7.14 (2H, d, J = 8.8 Hz), 7.61 (1H, br s), 7.79 (2H, d, J = 8.8 Hz), 8.01 (1H, br s), 8.30 (1H, d, J = 8.5 Hz), 8.83 (1H, d, J = 8.5 Hz), 8.85 (1H, s), 9.46 (1H, s). MS (FAB) m/z: 368 (M + H)⁺ |
| 66 | [structure] | A | ¹H-NMR (DMSO-D$_6$) δ: 2.49-2.53 (4H, m), 2.72-2.78 (2H, m), 3.57-3.63 (4H, m), 4.16-4.23 (2H, m), 7.14 (2H, d, J = 8.8 Hz), 7.60 (1H, br s), 7.79 (2H, d, J = 8.8 Hz), 8.02 (1H, br s), 8.30 (1H, d, J = 8.5 Hz), 8.83 (1H, d, J = 8.5 Hz), 8.85 (1H, s), 9.46 (1H, s). MS (FAB) m/z: 379 (M + H)⁺ |
| 67 | [structure] | A | ¹H-NMR (DMSO-D$_6$) δ: 3.50-3.56 (4H, m), 3.75-3.81 (2H, m), 4.19-4.21 (2H, m), 4.64-4.65 (1H, m), 7.14 (2H, d, J = 8.8 Hz), 7.61 (1H, br s), 7.79 (2H, d, J = 8.8 Hz), 8.01 (1H, br s), 8.30 (1H, d, J = 8.5 Hz), 8.83 (1H, d, J = 8.5 Hz), 8.85 (1H, s), 9.46 (1H, s). MS (FAB) m/z: 354 (M + H)⁺ |
| 68 | [structure] | A | ¹H-NMR (DMSO-D$_6$) δ: 1.48-1.58 (1H, m), 1.88-1.98 (1H, m), 2.41-2.49 (1H, m), 3.36-3.50 (3H, m), 3.56-3.65 (1H, m), 3.67-3.75 (2H, m), 3.76-3.81 (2H, m), 4.17-4.23 (2H, m), 7.14 (2H, d, J = 8.8 Hz), 7.61 (1H, br s), 7.79 (2H, d, J = 8.8 Hz), 8.01 (1H, br s), 8.30 (1H, d, J = 8.3 Hz), 8.83 (1H, d, J = 8.3 Hz), 8.85 (1H, s), 9.46 (1H, s). MS (FAB) m/z: 394 (M + H)⁺ |

TABLE 9-continued

| 69 | 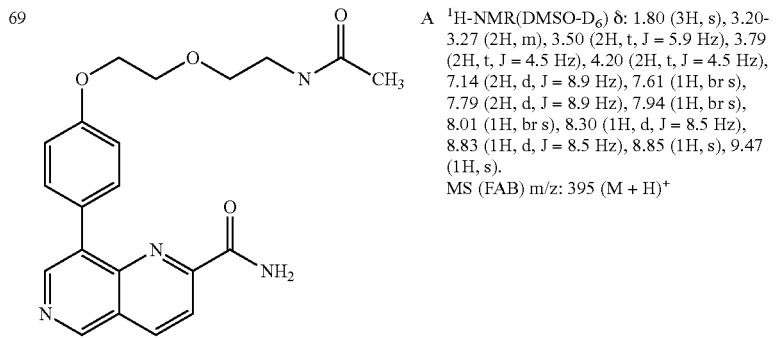 | A | $^1$H-NMR(DMSO-D$_6$) δ: 1.80 (3H, s), 3.20-3.27 (2H, m), 3.50 (2H, t, J = 5.9 Hz), 3.79 (2H, t, J = 4.5 Hz), 4.20 (2H, t, J = 4.5 Hz), 7.14 (2H, d, J = 8.9 Hz), 7.61 (1H, br s), 7.79 (2H, d, J = 8.9 Hz), 7.94 (1H, br s), 8.01 (1H, br s), 8.30 (1H, d, J = 8.5 Hz), 8.83 (1H, d, J = 8.5 Hz), 8.85 (1H, s), 9.47 (1H, s).<br>MS (FAB) m/z: 395 (M + H)$^+$ |

TABLE 10

| 70 | 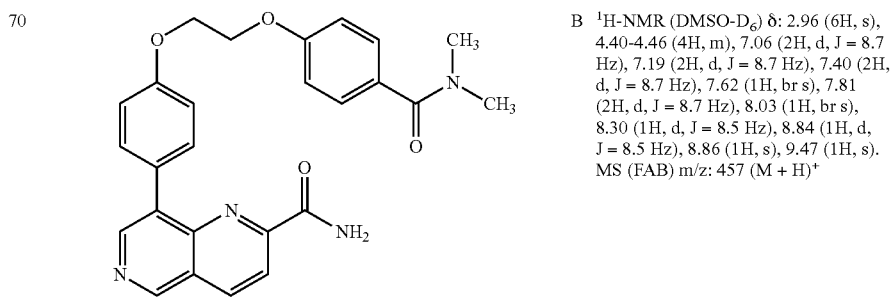 | B | $^1$H-NMR (DMSO-D$_6$) δ: 2.96 (6H, s), 4.40-4.46 (4H, m), 7.06 (2H, d, J = 8.7 Hz), 7.19 (2H, d, J = 8.7 Hz), 7.40 (2H, d, J = 8.7 Hz), 7.62 (1H, br s), 7.81 (2H, d, J = 8.7 Hz), 8.03 (1H, br s), 8.30 (1H, d, J = 8.5 Hz), 8.84 (1H, d, J = 8.5 Hz), 8.86 (1H, s), 9.47 (1H, s).<br>MS (FAB) m/z: 457 (M + H)$^+$ |
| 71 (less polar) | 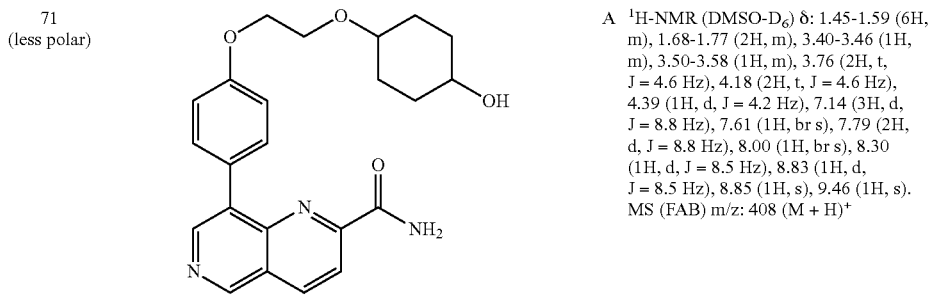 | A | $^1$H-NMR (DMSO-D$_6$) δ: 1.45-1.59 (6H, m), 1.68-1.77 (2H, m), 3.40-3.46 (1H, m), 3.50-3.58 (1H, m), 3.76 (2H, t, J = 4.6 Hz), 4.18 (2H, t, J = 4.6 Hz), 4.39 (1H, d, J = 4.2 Hz), 7.14 (3H, d, J = 8.8 Hz), 7.61 (1H, br s), 7.79 (2H, d, J = 8.8 Hz), 8.00 (1H, br s), 8.30 (1H, d, J = 8.5 Hz), 8.83 (1H, d, J = 8.5 Hz), 8.85 (1H, s), 9.46 (1H, s).<br>MS (FAB) m/z: 408 (M + H)$^+$ |
| 72 (morepolar) | 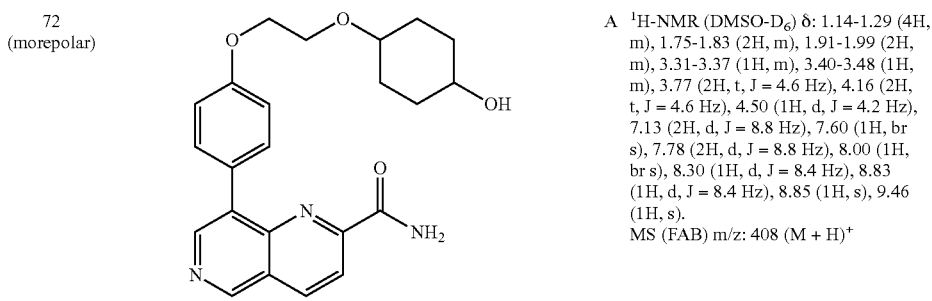 | A | $^1$H-NMR (DMSO-D$_6$) δ: 1.14-1.29 (4H, m), 1.75-1.83 (2H, m), 1.91-1.99 (2H, m), 3.31-3.37 (1H, m), 3.40-3.48 (1H, m), 3.77 (2H, t, J = 4.6 Hz), 4.16 (2H, t, J = 4.6 Hz), 4.50 (1H, d, J = 4.2 Hz), 7.13 (2H, d, J = 8.8 Hz), 7.60 (1H, br s), 7.78 (2H, d, J = 8.8 Hz), 8.00 (1H, br s), 8.30 (1H, d, J = 8.4 Hz), 8.83 (1H, d, J = 8.4 Hz), 8.85 (1H, s), 9.46 (1H, s).<br>MS (FAB) m/z: 408 (M + H)$^+$ |

TABLE 10-continued

| 73 | 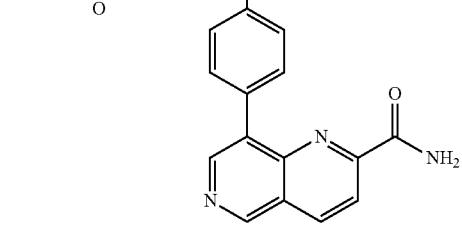 | B | $^1$H-NMR (DMSO-D$_6$) δ: 2.85 (6H, s), 4.26-4.32 (2H, m), 4.33-4.37 (2H, m), 7.16 (2H, d, J= 8.8 Hz), 7.60 (1H, br s), 7.80 (2H, d, J = 8.8 Hz), 8.01 (1H, br s), 8.30 (1H, d, J = 8.5 Hz), 8.83 (1H, d, J = 8.5 Hz), 8.85 (1H, s), 9.47 (1H, s).<br>MS (FAB) m/z: 381 (M + H)$^+$ |
|---|---|---|---|
| 74 | 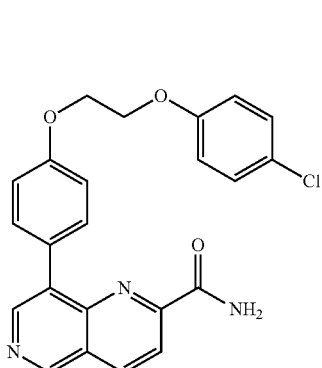 | B | $^1$H-NMR (DMSO-D$_6$) δ: 4.36-4.43 (4H, m), 7.06 (2H, d, J = 9.2 Hz), 7.18 (2H, d, J = 8.9 Hz), 7.36 (2H, d, J = 9.2 Hz), 7.62 (1H, br s), 7.81 (2H, d, J = 8.9 Hz), 8.03 (1H, br s), 8.30 (1H, d, J = 8.5 Hz), 8.84 (1H, d, J = 8.5 Hz), 8.86 (1H, s), 9.47 (1H, s).<br>MS (FAB) m/z: 420 (M + H)$^+$ |
| 75 | 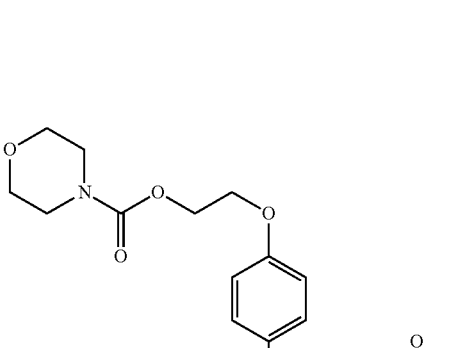 | B | $^1$H-NMR (DMSO-D$_6$) δ: 3.33-3.39 (4H, m), 3.48-3.60 (4H, m), 4.27-4.33 (2H, m), 4.36-4.44 (2H, m), 7.16 (2H, d, J = 8.5 Hz), 7.60 (1H, br s), 7.80 (2H, d, J = 8.5 Hz), 8.01 (1H, br s), 8.30 (1H, d, J = 8.5 Hz), 8.83 (1H, d, J = 8.5 Hz), 8.85 (1H, s), 9.47 (1H, s).<br>MS (FAB) m/z: 423 (M + H)$^+$ |

TABLE 11

| 76 |  | A | $^1$H-NMR (DMSO-D$_6$) δ: 3.76-3.83 (2H, m), 4.17 (2H, t, J = 4.9 Hz), 4.95 (1H, br s), 7.35 (1H, t, J = 8.8 Hz), 7.59-7.70 (2H, m), 7.77 (1H, dd, J = 12.9, 2.0 Hz), 7.99 (1H, br s), 8.30 (1H, d, J = 8.5 Hz), 8.84 (1H, d, J = 8.5 Hz), 8.88 (1H, s), 9.49 (1H, s).<br>MS (FAB) m/z: 328 (M + H)$^+$ |
|---|---|---|---|

TABLE 11-continued

| | | | |
|---|---|---|---|
| 77 | [structure] | B | $^1$H-NMR (DMSO-D$_6$) δ: 2.82 (3H, s), 2.94 (3H, s), 3.80-3.87 (2H, m), 4.18-4.27 (4H, m), 7.14 (2H, d, J = 8.5 Hz), 7.61 (1H, br s), 7.79 (2H, d, J = 8.5 Hz), 8.00 (1H, br s), 8.30 (1H, d, J = 8.5 Hz), 8.83 (1H, d, J = 8.5 Hz), 8.85 (1H, s), 9.46 (1H, s).<br>MS (FAB) m/z: 395 (M + H)$^+$ |
| 78 | [structure] | A | $^1$H-NMR (DMSO-D$_6$) δ: 1.39-1.48 (2H, m), 1.84-1.94 (2H, m), 3.34-3.39 (2H, m), 3.57-3.66 (1H, m), 3.78-3.88 (4H, m), 4.28 (2H, t, J = 4.6 Hz), 7.37 (1H, t, J = 8.8 Hz), 7.63 (1H, d, J = 8.8 Hz), 7.66 (1H, br s), 7.77 (1H, dd, J = 12.7, 2.2 Hz), 8.00 (1H, br s), 8.30 (1H, d, J = 8.5 Hz), 8.84 (1H, d, J = 8.5 Hz), 8.88 (1H, s), 9.49 (1H, s).<br>MS (FAB) m/z: 412 (M + H)$^+$ |
| 79 | [structure] | A | $^1$H-NMR (DMSO-D$_6$) δ: 1.19 (3H, s), 1.46-1.56 (2H, m), 1.63-1.71 (2H, m), 3.50-3.57 (2H, m), 3.57-3.66 (2H, m), 3.68-3.74 (2H, m), 4.25-4.31 (2H, m), 7.38 (1H, t, J = 8.8 Hz), 7.60-7.69 (2H, m), 7.77 (1H, dd, J = 12.8, 2.1 Hz), 8.00 (1H, br s), 8.31 (1H, d, J = 8.5 Hz), 8.84 (1H, d, J = 8.5 Hz), 8.88 (1H, s), 9.49 (1H, s).<br>MS (FAB) m/z: 426 (M + H)$^+$ |
| 80 | [structure] | A | $^1$H-NMR (DMSO-D$_6$) δ: 3.79-3.82 (2H, m), 4.19 (2H t J = 5.0 Hz) 4.86-4.97 (1H m), 7.35 (1H d J = 8.5 Hz) 7.61 (1H br s) 7.79 (1H, dd, J = 8.5, 2.1 Hz), 7.93 (1H, d, J = 2.1 Hz), 8.02 (1H, br s), 8.31 (1H, d, J = 8.5 Hz), 8.84 (1H, d, J = 8.5 Hz), 8.89 (1H, s), 9.49 (1H, s).<br>MS (FAB) m/z: 344 (M + H)$^+$ |

TABLE 11-continued

| | | | |
|---|---|---|---|
| 81 | 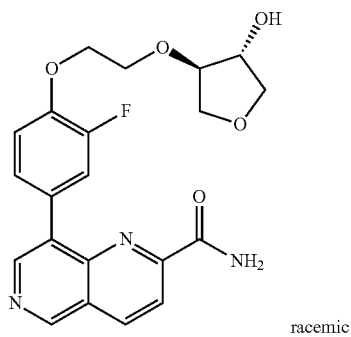 [SMILES: NC(=O)c1ccc2cncc(-c3ccc(OCCO[C@@H]4COC[C@H]4O)c(F)c3)c2n1] racemic | B | ¹H-NMR (DMSO-D$_6$) δ: 3.47-3.54 (1H, m), 3.64-3.69 (1H, m), 3.76-3.89 (4H, m), 3.89-3.94 (1H, m), 4.14-4.19 (1H, m), 4.24-4.31 (2H, m), 5.16 (1H, d, J = 3.7 Hz), 7.36 (1H, t, J = 8.7 Hz), 7.60-7.64 (1H, m), 7.66 (1H, br s), 7.78 (1H, dd, J = 12.8, 2.3 Hz), 7.99 (1H, br s), 8.30 (1H, d, J = 8.3 Hz), 8.84 (1H, d, J = 8.3 Hz), 8.88 (1H, s), 9.49 (1H, s). MS (EI) m/z: 414 (M + H)⁺. |

TABLE 12

| | | | |
|---|---|---|---|
| 82 | 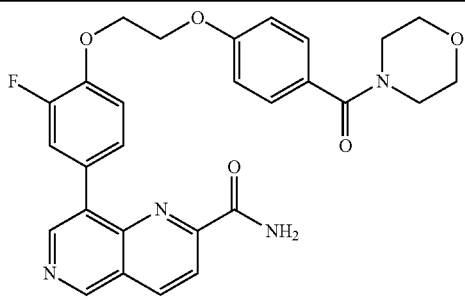 | B | ¹H-NMR (DMSO-D$_6$) δ: 3.44-3.55 (4H, m), 3.55-3.63 (4H, m), 4.43-4.46 (2H, m), 4.51-4.54 (2H, m), 7.08 (2H, d, J = 8.6 Hz), 7.40 (2H, d, J = 8.6 Hz), 7.43 (1H, t, J = 8.7 Hz), 7.65 (1H, d, J = 8.7 Hz), 7.67 (1H, br s), 7.79 (1H, dd, J = 12.6, 2.3 Hz), 8.01 (1H, br s), 8.31 (1H, d, J = 8.6 Hz), 8.84 (1H, d, J = 8.6 Hz), 8.89 (1H, s), 9.50 (1H, s). MS (FAB) m/z: 517 (M + H)⁺ |
| 83 | 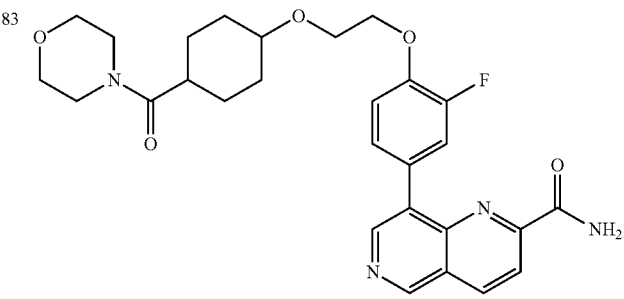 | B | ¹H-NMR (DMSO-D$_6$) δ: 1.20-2.10 (8H, m), 2.55-2.64 (1H, m), 3.37-3.67 (9H, m), 3.69-3.86 (2H, m), 4.21-4.31 (2H, m), 7.32-7.41 (1H, m), 7.61 (1H, d, J = 8.5 Hz), 7.65 (1H, br s), 7.72-7.79 (1H, m), 7.97 (1H, br s), 8.29 (1H, d, J = 8.5 Hz), 8.83 (1H, d, J = 8.5 Hz), 8.87 (1H, s), 9.47 (1H, s). MS (FAB) m/z: 523 (M + H)⁺ |
| 84 | 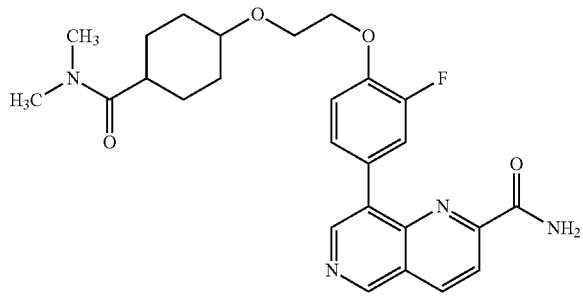 [SMILES: CN(C)C(=O)C1CCC(OCCOc2ccc(-c3cncc4ccc(C(N)=O)nc34)cc2F)CC1] | B | ¹H-NMR (DMSO-D$_6$) δ: 1.21-2.11 (8H, m), 2.54-2.67 (1H, m), 2.79 (3H, s), 3.00 (3H, s), 3.61-3.85 (3H, m), 4.23-4.33 (2H, m), 7.33-7.42 (1H, m), 7.59-7.64 (1H, m), 7.66 (1H, br s), 7.72-7.81 (1H, m), 7.98 (1H, br s), 8.30 (1H, d, J = 8.5 Hz), 8.84 (1H, d, J = 8.5 Hz), 8.88 (1H, s), 9.49 (1H, s). MS (FAB) m/z: 481 (M + H)⁺ |

TABLE 12-continued

| | | | |
|---|---|---|---|
| 85 | 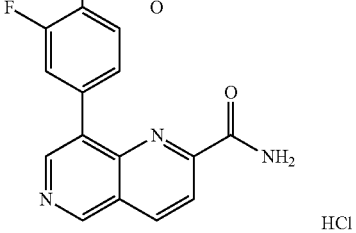 HCl | A | $^1$H-NMR (DMSO-D$_6$) δ: 3.03 (3H, s), 3.31 (3H, s), 7.63-7.82 (3H, m), 7.97-8.03 (2H, m), 8.33 (1H, d, J = 8.5 Hz), 8.88 (1H, d, J = 8.5 Hz), 8.96 (1H, s), 9.58 (1H, s). MS (FAB) m/z: 405 (M + H)$^+$ |
| 86 | 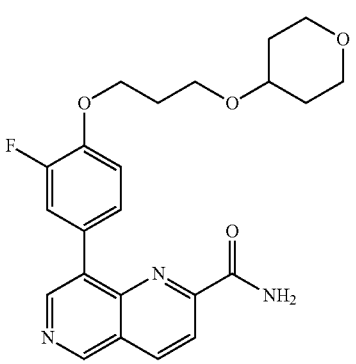 [SMILES: NC(=O)c1ccc2cncc(-c3ccc(OCCCOC4CCOCC4)c(F)c3)c2n1] | B | $^1$H-NMR (DMSO-D$_6$) δ: 1.34-1.43 (2H, m), 1.80-1.87 (2H, m), 1.97-2.04 (2H, m), 3.28-3.32 (2H, m), 3.45-3.52 (1H, m), 3.58-3.63 (2H, m), 3.74-3.81 (2H, m), 4.18-4.23 (2H, m), 7.34 (1H, t, J = 8.6 Hz), 7.62 (1H, d, J = 8.6 Hz), 7.65 (1H, br s), 7.76 (1H, d, J = 12.8 Hz), 8.00 (1H, br s), 8.29 (1H, d, J = 8.7 Hz), 8.83 (1H, d, J = 8.7 Hz), 8.87 (1H, s), 9.48 (1H, s). MS (FAB) m/z: 426 (M + H)$^+$ |
| 87 | 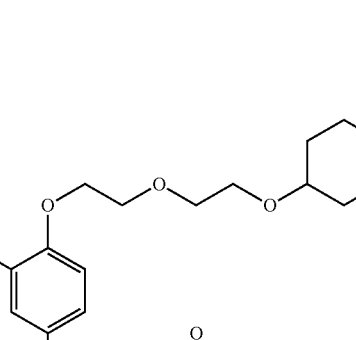 | B | $^1$H-NMR (DMSO-D$_6$) δ:1.31-1.40 (2H, m), 1.78-1.85 (2H, m), 3.25-3.31 (2H, m), 3.44-3.51 (1H, m), 3.55-3.64 (4H, m), 3.73-3.79 (2H, m), 3.80-3.84 (2H, m), 4.25-4.29 (2H, m), 7.35 (1H, t, J = 8.7 Hz), 7.59-7.63 (1H, m), 7.65 (1H, br s), 7.76 (1H, dd, J = 12.8, 2.3 Hz), 8.00 (1H, br s), 8.29 (1H, d, J = 8.5 Hz), 8.83 (1H, d, J = 8.5 Hz), 8.86 (1H, s), 9.48 (1H, s). MS (FAB) m/z: 456 (M + H)$^+$ |

TABLE 13

| | | | |
|---|---|---|---|
| 88 | | B | $^1$H-NMR (DMSO-D$_6$) δ: 3.40-3.45 (4H, m), 3.51-3.59 (4H, m), 3.80-3.93 (2H, m), 4.25 (2H, s), 4.28-4.34 (2H, m), 7.35 (1H, t, J = 8.8 Hz), 7.59-7.64 (1H, m), 7.65 (1H, br s), 7.77 (1H, dd, J = 12.8, 2.1 Hz), 7.99 (1H, br s), 8.29 (1H, d, J = 8.5 Hz), 8.83 (1H, d, J = 8.5 Hz), 8.87 (1H, s), 9.48 (1H, s). MS (FAB) m/z: 455 (M + H)$^+$ |

TABLE 13-continued

| 89 | 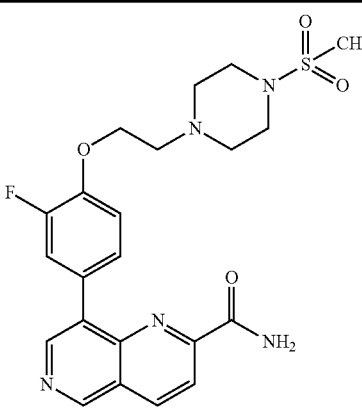 | B | $^1$H-NMR(DMSO-D$_6$) δ: 2.62-2.67 (4H, m), 2.85 (2H, t, J = 5.6 Hz), 2.88 (3H, s), 3.11-3.15 (4H, m), 4.28 (2H, t, J = 5.6 Hz), 7.38 (1H, t, J = 8.8 Hz), 7.61-7.68 (2H, m), 7.75-7.80 (1H, dd, J = 12.5, 1.8 Hz), 8.01 (1H, br s), 8.30 (1H, d, J = 8.4 Hz), 8.84 (1H, d, J = 8.4 Hz), 8.88 (1H, s), 9.49 (1H, s). MS (FAB) m/z: 474 (M + H)$^+$ |
| 90 | 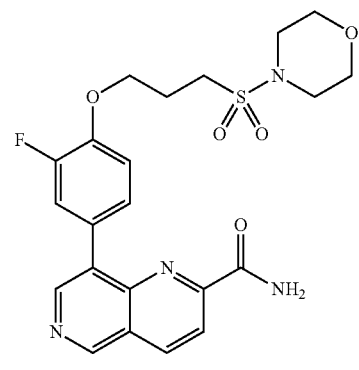 [SMILES: NC(=O)c1ccc2cncc(-c3ccc(OCCCS(=O)(=O)N4CCOCC4)c(F)c3)c2n1] | A | $^1$H-NMR (DMSO-D$_6$) δ: 2.16-2.25 (2H, m), 3.17-3.21 (4H, m), 3.27-3.31 (2H, m), 3.62-3.69 (4H, m), 4.28 (2H, t, J = 6.2 Hz), 7.35 (1H, t, J = 8.8 Hz), 7.61-7.69 (2H, m), 7.79 (1H, dd, J = 12.7, 2.0 Hz), 8.01 (1H, br s), 8.30 (1H, d, J = 8.5 Hz), 8.84 (1H, d, J = 8.3 Hz), 8.89 (1H, s), 9.49 (1H, s). MS (FAB) m/z: 475 (M + H)$^+$ |
| 91 | 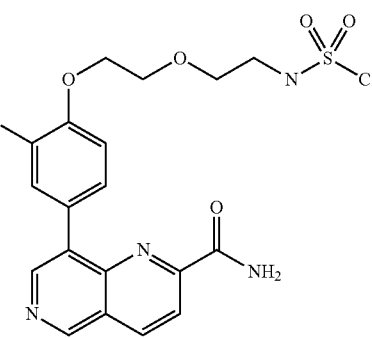 | A | $^1$H-NMR (DMSO-D$_6$) δ: 2.93 (3H, s), 3.13-3.19 (2H, q, J = 5.7 Hz), 3.58 (2H, t, J = 5.7 Hz), 3.83 (2H, t, J = 4.5 Hz), 4.29 (2H, t, J = 4.5 Hz), 7.09 (1H, t, J = 5.7 Hz), 7.35 (1H, t, J = 8.8 Hz), 7.59-7.70 (2H, m), 7.78 (1H, dd, J = 12.7, 2.0 Hz), 8.00 (1H, br s), 8.30 (1H, d, J = 8.5 Hz), 8.84 (1H, d, J = 8.5 Hz), 8.88 (1H, s) 9.49 (1H s). MS (FAB) m/z: 449 (M + H)$^+$ |
| 92 | 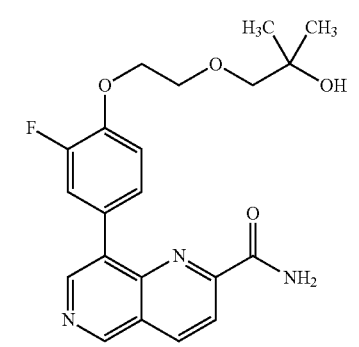 [SMILES: CC(C)(O)COCCOc1ccc(-c2cncc3ccc(C(N)=O)nc23)cc1F] | B | $^1$H-NMR(DMSO-D$_6$) δ: 1.09 (6H s) 3.32 (2H, s), 3.82-3.87 (2H, m), 4.27-4.35 (2H, m), 7.38 (1H, t, J = 8.7 Hz), 7.63 (1H, d, J = 8.7 Hz), 7.66 (1H, br s), 7.77 (1H, dd, J = 12.7, 1.2 Hz), 8.00 (1H, br s), 8.30 (1H, d, J = 8.5 Hz), 8.84 (1H, d, J = 8.5 Hz), 8.88 (1H, s) 9.49 (1H, s). MS (FAB) m/z: 400 (M + H)$^+$ |

TABLE 13-continued

| 93 | 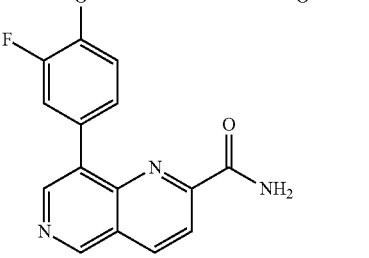 | B | ¹H-NMR (CDCl₃) δ: 1.82-2.01 (4H, m), 2.78 (3H, s), 3.20-3.28 (2H, m), 3.33-3.41 (2H, m), 3.68-3.75 (1H, m), 3.89-3.94 (2H, m), 4.28-4.33 (2H, m), 5.69 (1H, br s), 5.69 (1H, s), 7.17 (1H, t, J = 8.5 Hz), 7.42-7.46 (1H, m), 7.57 (1H, dd, J = 12.2, 2.2 Hz), 7.73 (1H, br s), 8.48 (1H, d, J = 8.5 Hz), 8.56 (1H, d, J = 8.5 Hz), 8.86 (1H, s), 9.36 (1H, s).<br>MS (EI) m/z: 489 (M + H)⁺ |
|---|---|---|---|

TABLE 14

| 94 | 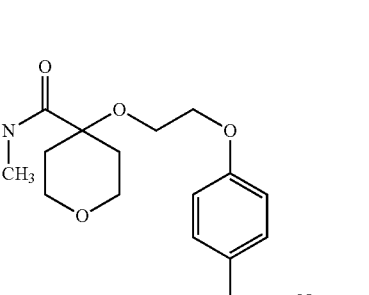 | B | ¹H-NMR (DMSO-D₆) δ: 0.37-0.50 (4H, m), 3.28-3.33 (1H, m), 3.57-3.64 (4H, m), 3.81 (2H, t, J = 4.6 Hz), 4.28 (2H, t, J = 4.6 Hz), 7.36 (1H, t, J = 8.9 Hz), 7.60-7.65 (1H, m), 7.66 (1H, s), 7.75-7.81 (1H, dd, J = 12.8, 1.8 Hz), 8.01 (1H, s), 8.30 (1H, d, J = 8.7 Hz), 8.84 (1H, d, J = 8.7 Hz), 8.88 (1H, s), 9.49 (1H, s).<br>MS (FAB) m/z: 412 (M + H)⁺ |
|---|---|---|---|
| 95 | 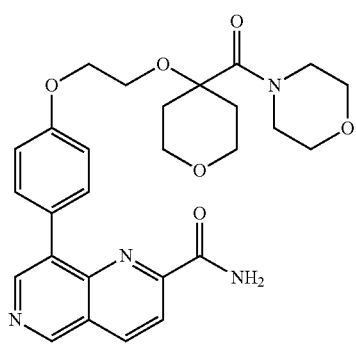 [SMILES: NC(=O)c1ccc2cncc(-c3ccc(OCCOC4(C(=O)N5CCOCC5)CCOCC4)cc3)c2n1] | B | ¹H-NMR (DMSO-D₆) δ: 1.84-2.04 (4H, m), 2.89 (3H, s), 3.32 (3H, s), 3.57-3.74 (6H, m), 4.22-4.35 (2H, m), 7.14 (2H, d, J = 8.5 Hz), 7.60 (1H, br s), 7.80 (2H, d, J = 8.5 Hz), 8.03 (1H, br s), 8.30 (1H, d, J = 8.5 Hz), 8.83 (1H, d, J = 8.5 Hz), 8.85 (1H, s), 9.47 (1H, s).<br>MS (FAB) m/z: 465 (M + H)⁺ |
| 96 | | B | ¹H-NMR (DMSO-D₆) δ: 1.81-1.91 (2H, m), 1.91-2.02 (2H, m), 3.41-3.73 (12H, m), 3.89-4.03 (2H, m), 4.21-4.30 (2H, m), 7.15 (2H, d, J = 8.5 Hz), 7.60 (1H, br s), 7.81 (2H, d, J = 8.5 Hz), 8.01 (1H, br s), 8.30 (1H, d, J = 8.5 Hz), 8.83 (1H, d, J = 8.5 Hz), 8.83 (1H, s), 9.47 (1H, s).<br>MS (FAB) m/z: 507 (M + H)⁺ |

TABLE 14-continued

| 97 | 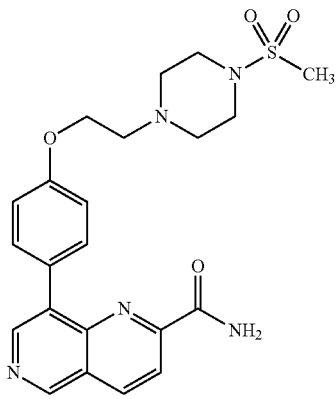 [SMILES: CS(=O)(=O)N1CCN(CCOc2ccc(-c3cncc4ccc(C(N)=O)nc34)cc2)CC1] | B | $^1$H-NMR (DMSO-D$_6$) δ: 2.60-2.66 (4H, m), 2.82 (2H, t, J = 5.6 Hz), 3.10-3.16 (4H, m), 4.20 (2H, t, J = 5.6 Hz), 7.14 (2H, d, J = 8.8 Hz), 7.60 (1H, br s), 7.79 (2H, d, J = 8.8 Hz), 8.01 (1H, br s), 8.30 (1H, d, J = 8.3 Hz), 8.83 (1H, d, J = 8.3 Hz), 8.85 (1H, s), 9.46 (1H, s).<br>MS (FAB) m/z: 456 (M + H)$^+$ |
|---|---|---|---|
| 98 | 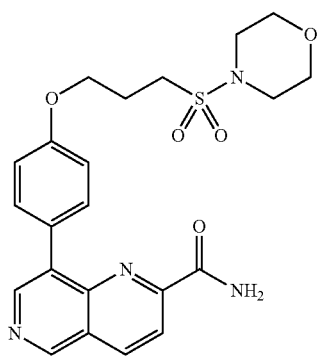 [SMILES: NC(=O)c1ccc2cncc(-c3ccc(OCCCS(=O)(=O)N4CCOCC4)cc3)c2n1] | B | $^1$H-NMR (DMSO-D$_6$) δ: 2.15-2.24 (2H, m), 3.17-3.22 (4H, m), 3.26-3.31 (2H, m), 3.63-3.68 (4H, m), 4.20 (2H, t, J = 6.1 Hz), 7.15 (2H, d, J = 8.5 Hz), 7.61 (1H, br s), 7.81 (2H, d, J = 8.5 Hz), 8.02 (1H, br s), 8.30 (1H, d, J = 8.3 Hz), 8.83 (1H, d, J = 8.3 Hz), 8.85 (1H, s), 9.47 (1H, s).<br>MS (FAB) m/z: 457 (M + H)$^+$ |
| 99 | 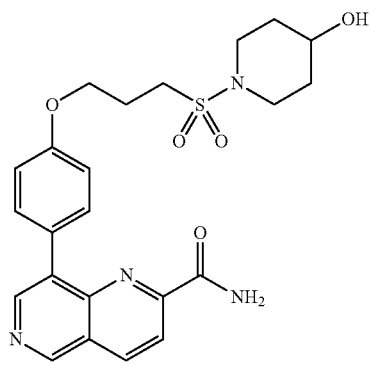 [SMILES: NC(=O)c1ccc2cncc(-c3ccc(OCCCS(=O)(=O)N4CCC(O)CC4)cc3)c2n1] | B | $^1$H-NMR (DMSO-D$_6$) δ: 1.39-1.50 (2H, m), 1.73-1.82 (2H, m), 2.12-2.21 (2H, m), 2.99-3.07 (2H, m), 3.20-3.26 (2H, m), 3.40-3.49 (2H, m), 3.60-3.69 (1H, m), 4.15-4.22 (2H, m), 4.77-4.80 (1H, m), 7.14 (2H, d, J = 7.7 Hz), 7.60 (1H, br s), 7.80 (2H, d, J = 7.7 Hz), 8.01 (1H, br s), 8.30 (1H, d, J = 8.5 Hz), 8.83 (1H, d, J = 8.5 Hz), 8.85 (1H, s), 9.47 (1H, s).<br>MS (FAB) m/z: 471 (M + H)$^+$ |

TABLE 15

| 100 | 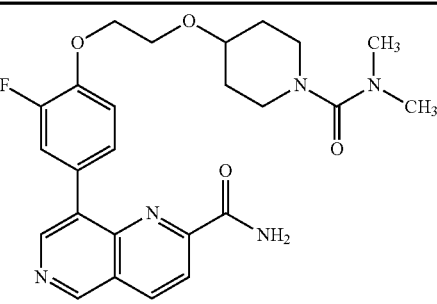 | B | $^1$H-NMR(CDCl$_3$) δ: 1.56-1.72 (2H1, m), 1.89-1.98 (2H, m), 2.82 (6H, s), 2.94-3.03 (2H, m), 3.47-3.55 (2H, m), 3.58-3.67 (1H, m), 3.92 (2H, t, J = 4.9 Hz), 4.31 (2H, t, J = 4.9 Hz), 5.89 (1H, br s), 7.19 (1H, t, J = 8.4 Hz), 7.41-7.46 (1H, m), 7.55 (1H, dd, J = 12.2, 2.2 Hz) 7.74 (1H br s) 8.47 (1H d J = 8.4 Hz), 8.55 (1H, d, J = 8.4 Hz), 8.86 (1H, s), 9.35 (1H, s).<br>MS (EI) m/z: 482 (M + H)$^+$ |
|---|---|---|---|

TABLE 15-continued

| | | | |
|---|---|---|---|
| 101 | [structure] | B | ¹H-NMR (CDCl₃) δ: 1.71-1.81 (2H, m), 1.91-2.00 (2H, m), 2.81 (6H, s), 3.11-3.19 (2H, m), 3.45-3.53 (2H, m), 3.62-3.68 (1H, m), 3.91 (2H, t, J = 4.8 Hz), 4.30 (2H, t, J = 4.8 Hz), 5.74 (1H, br s), 7.17 (1H, t, J = 8.5 Hz), 7.42-7.46 (1H, m), 7.56 (1H, dd, J = 12.3, 2.1 Hz), 7.75 (1H, br s), 8.48 (1H, d, J = 8.4 Hz), 8.55 (1H, d, J = 8.4 Hz), 8.86 (1H, s), 9.35 (1H, s).<br>MS (EI) m/z: 518 (M + H)⁺ |
| 102 | [structure] | C | ¹H-NMR (DMSO-D₆) δ: 3.50-3.58 (4H, m), 3.81 (2H, m), 4.22 (2H, m), 4.63-4.65 (1H, m), 7.17 (2H, d, J = 8.5 Hz, 7.50 (2H, d, J = 8.5 Hz), 7.61 (1H, br s), 8.11 (1H, d, J = 8.5 Hz), 8.23 (1H, br s), 8.28 (1H, d, J = 8.5 Hz), 8.37 (1H, s), 8.47 (1H, s), 9.37 (1H, s).<br>MS (FAB) m/z 353 (M + H)⁺ |
| 103 | [structure] | C | ¹H-NMR (DMSO-D₆) δ: 2.13-2.24 (2H, m), 3.19-3.20 (4H, m), 3.29 (2H, m), 3.65-3.66 (4H, m), 4.20-4.23 (2H, m), 7.17 (2H, d, J = 8.8 Hz), 7.52 (2H, d, J = 8.8 Hz), 7.62 (1H, br s), 8.11 (1H, d, J = 8.5 Hz), 8.23 (1H, br s), 8.28 (1H, d, J = 8.5 Hz), 8.37 (1H, s), 8.48 (1H, s), 9.38 (1H, s).<br>MS (FAB) m/z 456 (M + H)⁺ |
| 104 | [structure] HCl | B | ¹H-NMR (DMSO-D₆) δ: 4.46 (4H, s), 7.11 (2H, d, J = 8.7 Hz), 7.21 (2H, d, J = 8.7 Hz), 7.65 (1H, br s), 7.84 (2H, d, J = 8.7 Hz), 7.92 (2H, d, J = 8.7 Hz), 8.07 (1H, br s), 8.36 (1H, d, J = 8.7 Hz), 8.91 (1H, s), 8.91 (1H, d, J = 8.7 Hz), 9.60 (1H, s).<br>MS (FAB) m/z: 430 (M + H)⁺ |
| 105 | [structure] | B | ¹H-NMR (DMSO-D₆) δ: 3.83 (3H, s), 4.44-4.48 (4H, m), 7.14 (2H, d, J = 8.7 Hz), 7.19 (2H, d, J = 8.7 Hz), 7.61 (1H, br s), 7.81 (2H, d, J = 8.7 Hz), 7.94 (2H, d, J = 8.7 Hz), 8.01 (1H, br s), 8.30 (1H, d, J = 8.7 Hz), 8.84 (1H, d, J = 8.7 Hz), 8.86 (1H, s), 9.47 (1H, s).<br>MS (FAB) m/z: 444 (M + H)⁺ |

TABLE 16

| 106 | [structure] | B | ¹H-NMR (DMSO-D₆) δ: 4.46 (2H, t, J = 4.5 Hz), 4.73 (2H, t, J = 4.5 Hz), 6.99 (1H, d, J = 8.6 Hz), 7.18 (2H, d, J = 8.6 Hz), 7.61 (1H, br s), 7.80 (2H, d, J = 8.6 Hz), 8.01 (1H, br s), 8.18 (1H, dd, J = 8.6, 2.3 Hz), 8.30 (1H, d, J = 8.6 Hz), 8.76 (1H, d, J = 2.3 Hz), 8.84 (1H, d, J = 8.6 Hz), 8.86 (1H, s), 9.47 (1H, s). MS (FAB) m/z: 431 (M + H)⁺ |
|---|---|---|---|
| 107 | [structure] HCl | B | ¹H-NMR (DMSO-D₆) δ: 4.45-4.51 (4H, m), 7.12 (2H, d, J = 8.5 Hz), 7.26 (2H, d, J = 8.5 Hz), 7.58 (2H, d, J = 8.5 Hz), 7.76 (1H, br s), 7.92 (2H, d, J = 8.5 Hz), 8.27 (1H, d, J = 8.5 Hz), 8.37 (1H, br s), 8.46 (1H, s), 8.50 (1H, d, J = 8.5 Hz), 8.61 (1H, s), 9.68 (1H, s). MS (FAB) m/z 429 (M + H)⁺ |
| 108 | [structure] | B | ¹H-NMR (DMSO-D₆) δ: 3.82 (3H, s), 4.46-4.49 (4H, m), 7.15 (2H, d, J = 8.6 Hz), 7.21 (2H, d, J = 8.6 Hz), 7.52 (2H, d, J = 8.6 Hz), 7.62 (1H, br s), 7.94 (2H, d, J = 8.6 Hz), 8.11 (1H, d, J = 8.6 Hz), 8.24 (1H, br s), 8.28 (1H, d, J = 8.6 Hz), 8.38 (1H, s), 8.48 (1H, s), 9.38 (1H, s). MS (FAB) m/z: 443 (M + H)⁺ |
| 109 | [structure] | C | ¹H-NMR (DMSO-D₆) δ: 2.80 (3H, d, J = 4.1 Hz), 7.62 (2H, d, J = 7.7 Hz), 7.66 (3H, d, J = 7.7 Hz), 8.10 (1H, d, J = 8.3 Hz), 8.26 (1H, s), 8.31 (1H, d, J = 8.3 Hz), 8.51 (1H, s), 8.68-8.74 (1H, m), 9.43 (1H, s). MS (FAB) m/z: 297 (M + H)⁺ |
| 110 | [structure] | C | ¹H-NMR(DMSO-D₆) δ: 1.12 (3H, t, J = 7.2 Hz), 3.27-3.32 (2H, m), 7.62 (2H, d, J = 8.3 Hz), 7.67 (2H, d, J = 8.3 Hz), 8.12 (1H, d, J = 8.6 Hz), 8.27 (1H, s), 8.32 (1H, d, J = 8.6 Hz), 8.51 (1H, s), 8.73-8.78 (1H, m), 9.43 (1H, s). MS (FAB) m/z: 311 (M + H)⁺ |

TABLE 16-continued

| No. | Structure | Method | Data |
|---|---|---|---|
| 111 | (structure: 8-[4-(2-{[4-(carboxy)cyclohexyl]oxy}ethoxy)phenyl]-1,6-naphthyridine-2-carboxamide, HCl) | B | $^1$H-NMR (DMSO-D$_6$) δ:1.16-1.27 (2H, m), 1.31-1.42 (2H, m), 1.87-1.94 (2H, m), 1.99-2.06 (2H, m), 2.14-2.22 (1H, m), 3.29-3.37 (1H, m), 3.78-3.82 (2H, m), 4.15-4.19 (2H, m), 7.15 (2H, d, J = 8.9 Hz), 7.64 (1H, br s), 7.81 (2H, d, J = 8.9 Hz), 8.07 (1H, br s), 8.35 (1H, d, J = 8.3 Hz), 8.89 (1H, s), 8.90 (1H, d, J = 8.3 Hz), 9.58 (1H, s). MS (FAB) m/z: 436 (M + H)$^+$ |
| 112 | (structure: 8-[4-(2-{[4-(carboxy)phenyl]oxy}ethoxy)phenyl]-1,6-naphthyridine-2-carboxamide, Na salt) | B | $^1$H-NMR (DMSO-D$_6$) δ: 4.28-4.31 (2H, m), 4.33-4.37 (2H, m), 6.79 (2H, d, J = 8.7 Hz), 7.12 (2H, d, J = 8.7 Hz), 7.55 (1H, br s), 7.73 (4H, d, J = 8.7 Hz), 7.97 (1H, br s), 8.23 (1H, d, J = 8.5 Hz), 8.77 (1H, d, J = 8.5 Hz), 8.79 (1H, s), 9.40 (1H, s). MS (FAB) m/z: 452 (M + H)$^+$ |

TABLE 17

| No. | Structure | Method | Data |
|---|---|---|---|
| 113 | (structure: 4-(3,4-difluorophenyl)isoquinoline-6-carboxamide) | C | $^1$H-NMR (DMSO-D$_6$) δ: 7.40-7.48 (1H, m), 7.60-7.80 (3H, m), 8.15 (1H, d, J = 8.6 Hz), 8.27 (1H, br s), 8.29-8.33 (2H, m), 8.52 (1H, s), 9.44 (1H, s). MS (FAB) m/z: 285 (M + H)$^+$ |
| 114 | (structure: 4-(3-chloro-4-fluorophenyl)isoquinoline-6-carboxamide) | C | $^1$H-NMR (DMSO-D$_6$) δ: 7.58-7.67 (3H, m), 7.82-7.86 (1H, m), 8.15 (1H, d, J = 8.5 Hz), 8.27 (1H, br s), 8.28 (1H, s), 8.31 (1H, d, J = 8.5 Hz) 8.52 (1H s) 9.44 (1H s). MS (FAB) m/z: 301 (M + H)$^+$ |
| 115 | (structure: 4-[4-(2-{[4-(ethoxycarbonyl)phenyl]oxy}ethoxy)phenyl]isoquinoline-6-carboxamide) | B | $^1$H-NMR (DMSO-D$_6$) δ: 1.32 (3H, t, J = 7.2 Hz), 4.29 (2H, q, J = 7.2 Hz), 4.45-4.50 (4H, m), 7.14 (2H, d, J = 8.8 Hz), 7.22 (2H, d, J = 8.8 Hz), 7.52 (2H, d, J = 8.8 Hz), 7.60 (1H, br s), 7.94 (2H, d, J = 8.8 Hz), 8.11 (1H, d, J = 8.5 Hz), 8.23 (1H, br s), 8.28 (1H, d, J = 8.5 Hz), 8.38 (1H, s), 8.48 (1H, s), 9.38 (1H, s). MS (FAB) m/z: 457 (M + H)$^+$ |

TABLE 17-continued

| 116 | 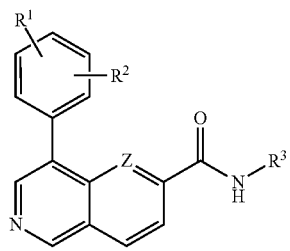 | B | $^1$H-NMR (DMSO-D$_6$) δ: 2.20 (3H, s), 4.45-4.50 (4H, m), 7.13 (1H, d J = 8.6 Hz), 7.21 (2H, d, J = 8.6 Hz), 7.61 (1H, br s), 7.75-7.77 (1H, m), 7.80-7.83 (3H, m), 8.02 (1H, br s), 8.31 (1H, d, J = 8.6 Hz), 8.84 (1H, d, J = 8.6 Hz), 8.86 (1H, s), 9.48 (1H, s). MS (FAB) m/z: 444 (M + H)$^+$ |
| --- | --- | --- | --- |
| 117 | 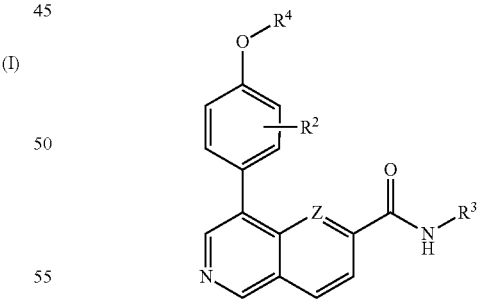 | B | $^1$H-NMR (DMSO-D$_6$) δ: 2.54 (3H, s), 4.44 (4H, s), 6.91-6.95 (2H, m), 7.21 (2H, d, J = 8.8 Hz), 7.65 (1H, br s), 7.84 (2H, d, J = 8.8 Hz), 7.87 (1H, d, J = 8.8 Hz), 8.08 (1H, br s), 8.37 (1H, d, J = 8.6 Hz), 8.92 (1H, s) 8.93 (1H, d, J = 8.6 Hz), 9.62 (1H, s). MS (FAB) m/z: 444 (M + H)+ |
| 118 | | C | $^1$H-NMR(DMSO-D$_6$) δ: 7.62 (2H, d, J = 8.5 Hz), 7.63 (1H, br s), 7.66 (2H, d, J = 8.5 Hz), 8.13 (1H, d, J = 8.6 Hz), 8.25 (1H, br s), 8.31 (1H, d, J = 8.6 Hz), 8.31 (1H, s), 8.51 (1H, s), 9.43 (1H, s). MS (EI) m/z: 282 (M)$^+$ |

The invention claimed is:

1. A compound having the general formula (I) or a pharmacologically acceptable salt thereof:

(I)

wherein each substituent is defined as follows:
R$^1$ and R$^2$ together form a pyrrolyl group,
R$^3$ represents a hydrogen atom or a C1-C6 alkyl group optionally substituted by a hydroxyl group, and
Z represents CH or N.

2. A compound or a pharmacologically acceptable salt thereof according to claim 1, wherein R$^3$ is a hydrogen atom, a methyl group, or an ethyl group.

3. A compound or a pharmacologically acceptable salt thereof having formula (I-a)

(I-a)

wherein each substituent is defined as follows:
R$^2$ represents a group selected from a substituent group α,
R$^3$ represents a hydrogen atom or a C1-C6 alkyl group optionally substituted by a hydroxyl group,
Z represents CH or N, and
R$^4$ represents a group selected from a substituent group δ, wherein
the substituent group α includes:
a hydrogen atom, a hydroxyl group, a halogen group, a nitro group, a C1-C6 alkylsulfonyl group, a halogeno C1-C6 alkyl group, a halogeno C1-C6 alkoxy group, a C1-C6 alkylcarbonyl group, a di C1-C6 alkylamino group, a di C1-C6 alkylaminocarbonyl group, a di C1-C6 alkylaminocarbonyloxy group, a phenoxy group, a C1-C6 alkoxycarbonyl group, a 4-morpholinyl group, a C1-C6 alkylamino group optionally substituted by groups selected from a substituent group β, a piperidinyl group optionally substituted by groups selected from a substituent group β, a piperazinyl group optionally substituted by groups selected from a substituent group β, a tetrahydropyridinyl group optionally substituted by groups selected from a substituent group β, a vinyl group optionally substituted by groups selected from a substituent group β, a C1-C6 alkyl group optionally substituted by groups selected from a substituent group β, a C1-C6 alkoxy group optionally substituted by groups selected from a substituent group β, a halogeno C1-C6 alkoxy group optionally substituted by groups selected from a substituent group β, and a C1-C6 alkoxy C1-C6 alkoxy group optionally substituted by groups selected from a substituent group β, wherein the substituent group β includes:

a hydroxyl group, a formyl group, a 2-tetrahydropyranyloxy group, a 3-tetrahydropyranyloxy group, a C1-C6 alkylcarbonyl group, a C1-C6 alkylsulfonyl group, a 4-morpholinyl group, a 4-morpholinylcarbonyl group, a 4-morpholinylcarbonyloxy group, a 4-morpholinylsulfonyl group, a 4-piperidinyl group, a di C1-C6 alkylaminocarbonyl group, a di C1-C6 alkylaminocarbonyloxy group, a di C1-C6 alkylphosphonate ester group, a 2-tetrahydrofuranyl group, a 3-tetrahydrofuranyl group, a C1-C6 alkylcarbonylamino group, a C1-C6 alkylsulfonylamino group, an alkyl group optionally substituted by groups selected from a substituent group γ, an alkoxy group optionally substituted by groups selected from a substituent group γ, a 4-tetrahydropyranyloxy group optionally substituted by groups selected from a substituent group γ, a C3-C6 cycloalkyl group optionally substituted by groups selected from a substituent group γ, a C3-C6 cycloalkyloxy group optionally substituted by groups selected from a substituent group γ, a 4-piperidinyloxy group optionally substituted by groups selected from a substituent group γ, a 1-piperidinylsulfonyl group optionally substituted by groups selected from a substituent group γ, a piperazinyl group optionally substituted by groups selected from a substituent group γ, a 3-tetrahydrofuranyloxy group optionally substituted by groups selected from a substituent group γ, a phenoxy group optionally substituted by groups selected from a substituent group γ, and a pyridyl group optionally substituted by groups selected from a substituent group γ, wherein the substituent group γ includes:

a hydroxyl group, a carboxyl group, a halogen group, a C1-C6 alkyl group, a C1-C6 alkoxy group, a di C1-C6 alkylaminosulfonyl group, a 4-morpholinylcarbonyl group, a C1-C6 alkylsulfonyl group, a C1-C6 alkoxycarbonyl group, a C1-C6 alkylcarbonylamino group, and a C1-C6 alkylsulfonylamino group, and the substituent group δ includes:

a halogeno C1-C6 alkyl group, a di C1-C6 alkylaminocarbonyl group, a phenyl group, a C1-C6 alkyl group optionally substituted by groups selected from the substituent group β, a halogeno C1-C6 alkyl group optionally substituted by groups selected from the substituent group β, and a C1-C6 alkoxy C1-C6 alkyl group optionally substituted by groups selected from the substituent group β.

4. A compound or a pharmacologically acceptable salt thereof according to claim 3, wherein $R^2$ is a hydrogen atom, a chlorine group, or a fluorine group.

5. A compound or a pharmacologically acceptable salt thereof according to claim 3, wherein $R^3$ is a hydrogen atom, a methyl group, or an ethyl group.

6. A compound or a pharmacologically acceptable salt thereof according to claim 3, wherein $R^4$ is a group selected from the following group of substituents:

a di C1-C6 alkylaminocarbonyl group, a C1-C6 alkyl group optionally substituted by groups selected from the substituent group β, and a C1-C6 alkoxy C1-C6 alkyl group optionally substituted by groups selected from the substituent group β.

7. A compound or a pharmacologically acceptable salt thereof according to claim 3, wherein $R^4$ is a group selected from the following group of substituents:

a C1-C6 alkyl group, a halogeno C1-C6 alkyl group, a 2-hydroxyethyl group, a 2-(tetrahydro-2H-pyran-4-yloxy)ethyl group, and a 2-(2-hydroxyethoxy)ethyl group.

8. A compound or a pharmacologically acceptable salt thereof selected from the following group of compounds:

8-[4-(morpholin-4-yl)phenyl]-1,6-naphthyridine-2-carboxamide,

8-[4-(2-hydroxyethoxy)phenyl]-1,6-naphthyridine-2-carboxamide,

8-{4-[2-(tetrahydro-2H-pyran-4-yloxy)ethoxy]phenyl}-1,6-naphthyridine-2-carboxamide, N-methyl-8-{4-[2-(tetrahydro-2H-pyran-4-yloxy)ethoxy]phenyl}-1,6-naphthyridine-2-carboxamide, N-ethyl-8-{4-[2-(tetrahydro-2H-pyran-4-yloxy)ethoxy]phenyl}-1,6-naphthyridine-2-carboxamide, 8-{4-[2-(2-hydroxyethoxy)ethoxy]phenyl}-1,6-naphthyridine-2-carboxamide, 8-(4-hydroxyphenyl)-1,6-naphthyridine-2-carboxamide, 8-(3-fluoro-4-hydroxyphenyl)-1,6-naphthyridine-2-carboxamide, 4-[4-(4-acetylpiperazin-1-yl)phenyl]isoquinoline-6-carboxamide, 4-[4-(propan-2-yloxy)phenyl]isoquinoline-6-carboxamide, 4-[4-(2-hydroxyethoxy)phenyl]isoquinoline-6-carboxamide, 4-(4-chloro-2-fluorophenyl)isoquinoline-6-carboxamide, 4-(2,4-difluorophenyl)isoquinoline-6-carboxamide, 4-[4-(difluoromethoxy)phenyl]isoquinoline-6-carboxamide, 4-{4-[2-(tetrahydro-2H-pyran-4-yloxy)ethoxy]phenyl}isoquinoline-6-carboxamide, N-methyl-4-{4-[2-(tetrahydro-2H-pyran-4-yloxy)ethoxy]phenyl}isoquinoline-6-carboxamide, 4-{4-[2-(2-hydroxyethoxy)ethoxy]phenyl} isoquinoline-6-carboxamide, 4-(4-chlorophenyl)isoquinoline-6-carboxamide, 4-(4-fluorophenyl)isoquinoline-6-carboxamide, 4-(4-hydroxyphenyl)isoquinoline-6-carboxamide,
4-(1H-indol-5-yl)isoquinoline-6-carboxamide,
4-(1-methyl-1H-indol-5-yl)isoquinoline-6-carboxamide,
N-ethyl-8-{4-[2-(tetrahydro-2H-pyran-4-yloxy)ethoxy]phenyl}-1,6-naphthyridine-2-carboxamide, and
8-{4-[2-(tetrahydro-2H-pyran-4-yloxy)ethoxy]phenyl)-1,6-naphthyridine-2-carboxamide.

9. A compound or a pharmacologically acceptable salt thereof according to claim 8, wherein the pharmacologically acceptable salt is a hydrochloride.

10. A pharmaceutical composition comprising a compound or a pharmacologically acceptable salt thereof according to claim 1 as an active ingredient.

11. A pharmaceutical composition comprising a compound or a pharmacologically acceptable salt thereof according to claim 3 as an active ingredient.

* * * * *